(12) United States Patent
Wardenburg et al.

(10) Patent No.: US 10,472,391 B2
(45) Date of Patent: Nov. 12, 2019

(54) METHODS AND COMPOSITIONS USING ADAM10 INHIBITORS TO TREAT BACTERIAL INFECTIONS

(71) Applicants: The University of Chicago, Chicago, IL (US); SRI International, Menlo Park, CA (US)

(72) Inventors: Juliane Bubeck Wardenburg, Chicago, IL (US); Katherine Weh, Chicago, IL (US); Leyi Gong, Menlo Park, CA (US)

(73) Assignees: THE UNIVERSITY OF CHICAGO, Chicago, IL (US); SRI INTERNATIONAL, Menlo Park, CA (US)

( * ) Notice: Subject to any disclaimer, the term of this patent is extended or adjusted under 35 U.S.C. 154(b) by 0 days.

(21) Appl. No.: 14/781,962

(22) PCT Filed: Apr. 4, 2014

(86) PCT No.: PCT/US2014/032959
§ 371 (c)(1),
(2) Date: Oct. 2, 2015

(87) PCT Pub. No.: WO2014/165746
PCT Pub. Date: Oct. 9, 2014

(65) Prior Publication Data
US 2016/0052964 A1 Feb. 25, 2016

Related U.S. Application Data

(60) Provisional application No. 61/809,064, filed on Apr. 5, 2013.

(51) Int. Cl.
| | |
|---|---|
| *C07K 5/02* | (2006.01) |
| *A61K 45/06* | (2006.01) |
| *A61K 9/00* | (2006.01) |
| *A61K 38/05* | (2006.01) |
| *C07K 14/81* | (2006.01) |
| *A61K 38/00* | (2006.01) |

(52) U.S. Cl.
CPC .......... *C07K 5/0202* (2013.01); *A61K 9/0014* (2013.01); *A61K 38/05* (2013.01); *A61K 45/06* (2013.01); *A61K 38/00* (2013.01); *C07K 14/8146* (2013.01)

(58) Field of Classification Search
CPC ....... A61K 45/06; A61K 38/00; A61K 9/0014
See application file for complete search history.

(56) References Cited

U.S. PATENT DOCUMENTS 6,172,064 B1   1/2001   Andrews et al. .......... 514/237.8
9,150,865 B2  10/2015   Bubeck Wardenburg

FOREIGN PATENT DOCUMENTS

WO    WO 2012/064865     5/2012

OTHER PUBLICATIONS

Bhakdi and Tranum-Jensen, *Microbiol. Rev.*, 55:733-751, 1991.
Brosnahan et al., *Immunol.*, 182:2364-2373, 2009.
Bubeck Wardenburg et al., *Infect. Immun.*, 75:1040-1044, 2007.
Bubeck Wardenburg et al., *Nature Med.*, 13:1405-1407, 2007.
Gonzalez et al.,*Cell Mol. Life Sci.*, 65:493-507, 2008.
Iacovache et al., *Biochim Biophys Acta.*, 1778 (7-8): 1611-23, 2008.
International Search Report and Written Opinion Issued in PCT/US14/32959, dated Aug. 20, 2014.
Jursch et al., *Infect. Dis.*, 62:2249, 1994.
Karginov et al., *Bioorg, Med, Chem.*, 15:5424, 2007.
Kennedy et al., *J. Infect. Dis.*, 202(7):1050-1058, 2010.
Maretzky et al., *Proc. Natl. Acad. Sci. USA*, 102:9182-9187, 2005.
Menzies and Kernodle, *Infect. Immun.*, 62:1843-1847, 1994.
O'Callaghan et al., *Infect. Immun.*, 65:1571-1578, 1997.
Ong and Leung, *Immun. Allergy Clinics of NA*, 30:309-321, 2010.
Patel et al., *Infect. Immun.*,55:3103-3110, 1987.
PUBCHEM SID-14927739 Deposit date: Oct. 25, 2006, p. 1 Fog.
Ragle et al., *Antimicrob. Agents Chemother.*, 54:298, 2010.
Reiss and Saftig, *Semin. Cell Dev. Biol.*, 20:126-137, 2009.
Shapiro and Weis, *Cold Spring Harb. Perspect. Biol.*, 1:a003053, 2009.
Song et al., *Science*, 274:1859-1866, 1996.
Tomita and Kamio, *Biosci. Biotechnol. Biochem.*, 61:565-572, 1997.
Tweten, *Infection and Immunity*, 73 (10): 6199-6209, 2005.
Walker and Bayley, *J. Biol. Chem.*, 270:23065, 1995.
Wilke and Bubeck Wardenburg, *Proc. Natl. Acad. Sci. USA*, 107(30):13473-13478, 2010.

*Primary Examiner* — Rachael E Bredefeld
*Assistant Examiner* — Kaipeen E Yang
(74) *Attorney, Agent, or Firm* — Norton Rose Fulbright US LLP

(57) ABSTRACT

Certain embodiments are directed to compositions and methods of inhibiting a pathogenic bacterial infection involving ADAM10, specifically a method for treating pore-forming toxin-inducted pathology caused by exposure to *staphylococcus* in a subject, comprising administering an effective amount of a ADAM10 inhibitor to a patient. The methods include treating pneumonia or inhibiting disruption to epithelial barrier in a subject, having or at risk of developing staphylococcal infection.

10 Claims, 36 Drawing Sheets

SRI-028595
15920-LG59
391.25 g/mole

| Treatment | IC$_{50}$ (uM) | R$^2$ | % GI254023X IC$_{50}$ | Fold Difference |
|---|---|---|---|---|
| DMSO | | Not determined | | |
| GI254023X | 6.20 | 0.946 | 100 | 1 |
| SRI-028597 | 23.3 | 0.957 | 375 | 0.3 |
| SRI-028603 | 2.57 | 0.985 | 41 | 2.4 |
| SRI-028607 | 7.05 | 0.979 | 114 | 0.9 |
| SRI-028609 | 3.56 | 0.986 | 57 | 1.7 |
| SRI-028610 | 4.84 | 0.845 | 78 | 1.3 |

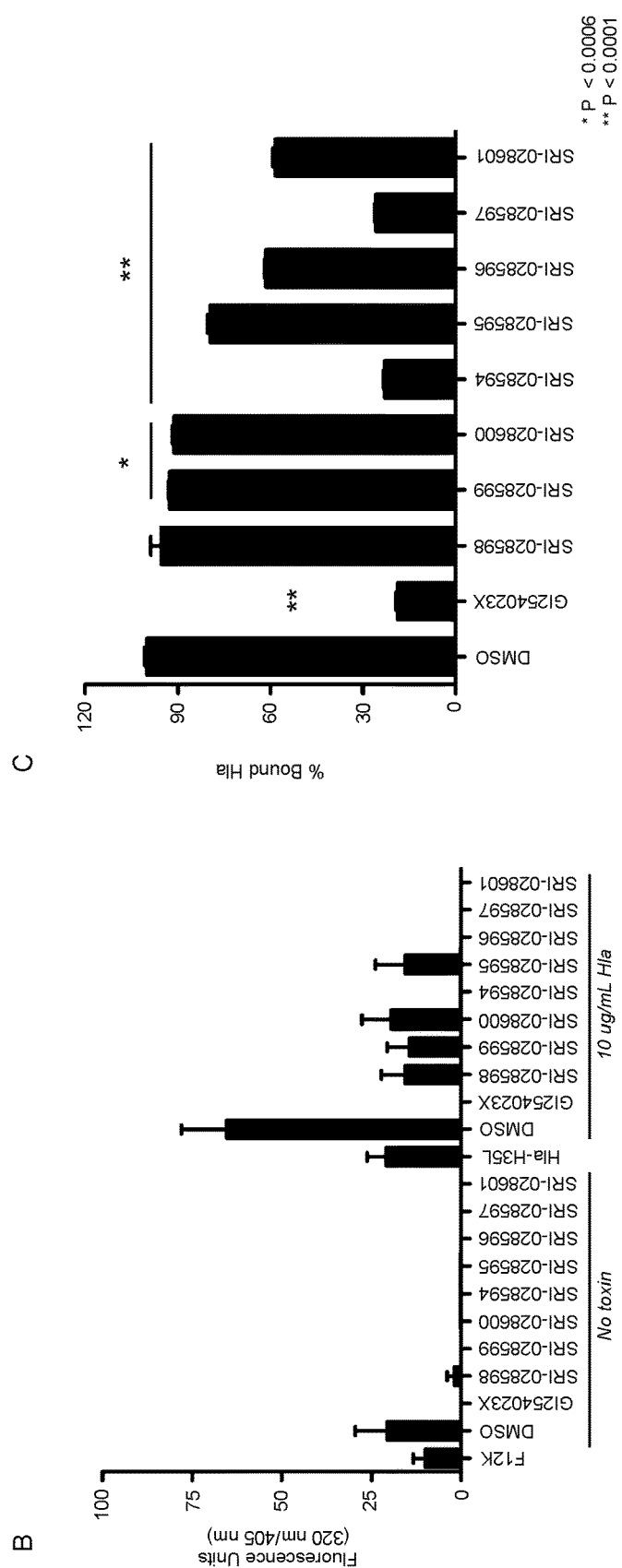
FIG. 7B-C

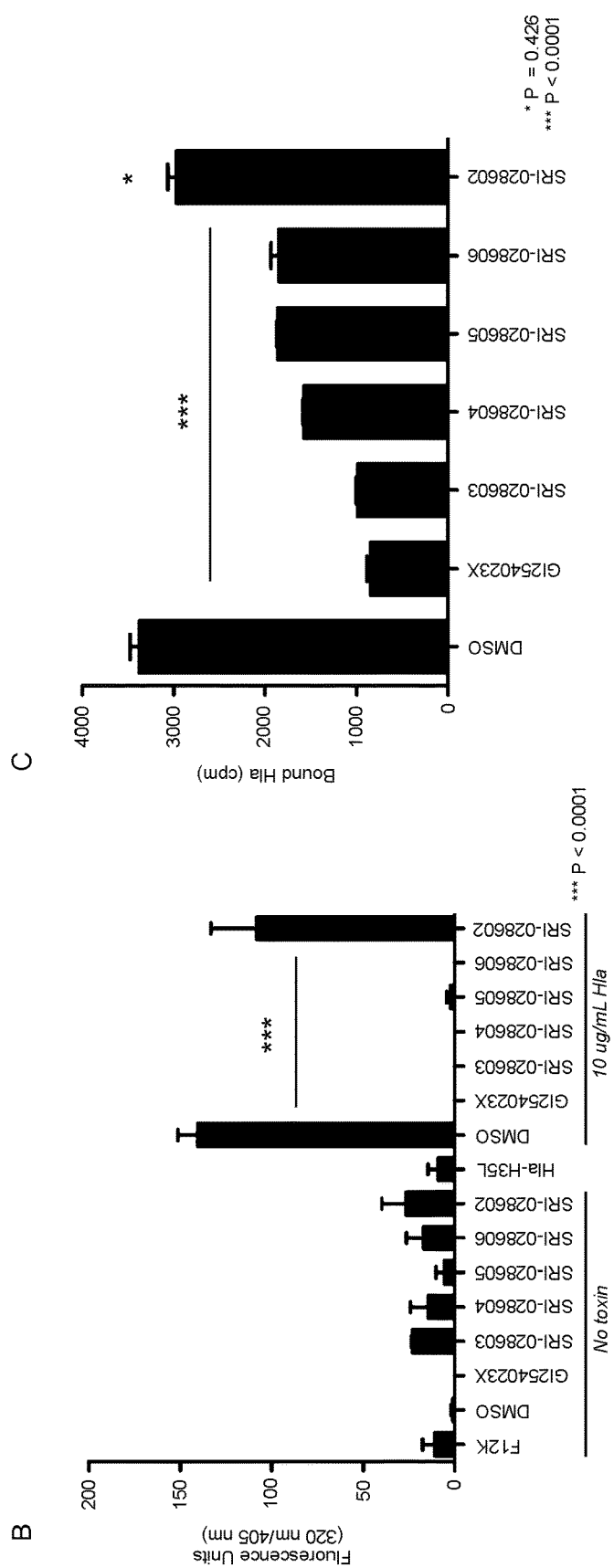
FIG. 8B-C

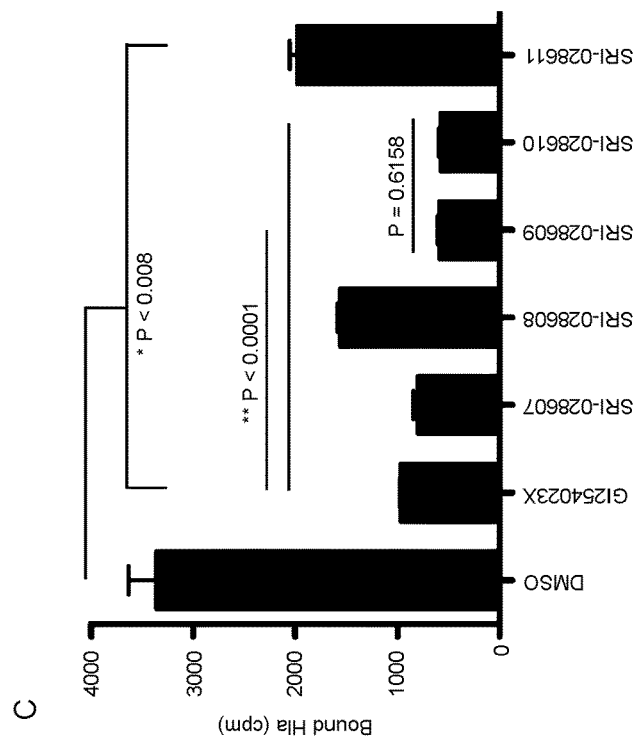
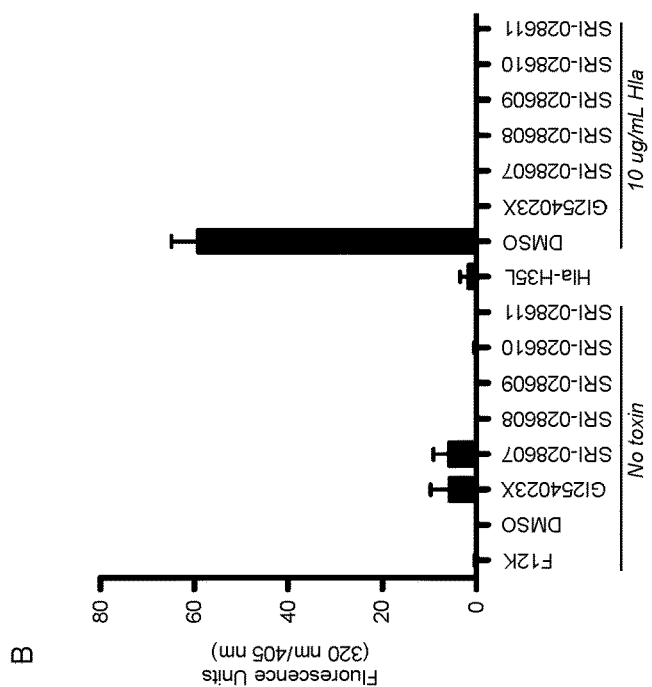
FIG. 9B-C

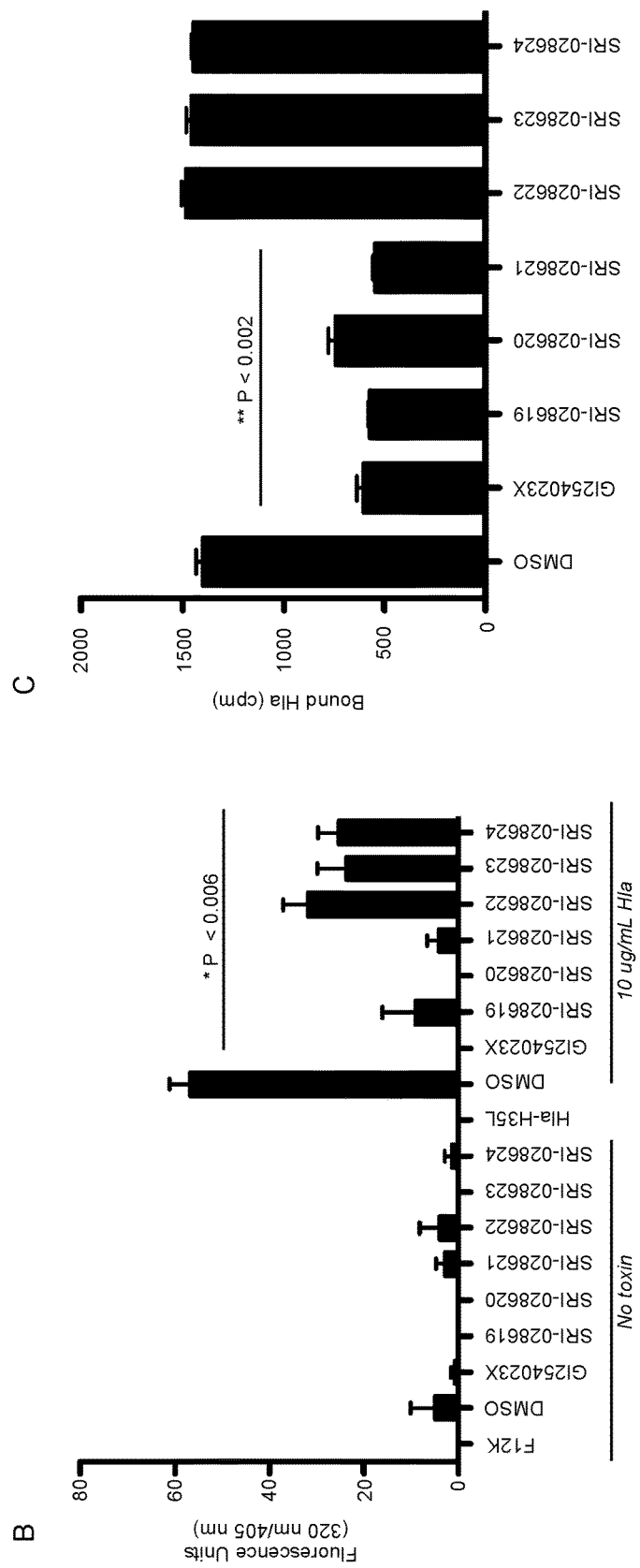
FIG. 10B-C

A

| Treatment | IC$_{50}$ (uM) | R$^2$ | % GI254023X IC$_{50}$ | Fold Difference |
|---|---|---|---|---|
| DMSO | 409.6 | 0.189 | Not determined | |
| GI254023X | 1.8 | 0.891 | 100 | 1 |
| SRI-028597 | 7.8 | 0.839 | 433 | 0.23 |
| SRI-028599 | Ambiguous | | Not determined | |

B

| Treatment | IC$_{50}$ (uM) | R$^2$ | % GI254023X IC$_{50}$ | Fold Difference |
|---|---|---|---|---|
| DMSO | 30.7 | 0.157 | Not determined | |
| GI254023X | 5.1 | 0.887 | 100 | 1 |
| SRI-028603 | 4.4 | 0.956 | 86 | 1.2 |

C

| Treatment | IC$_{50}$ (uM) | R$^2$ | % GI254023X IC$_{50}$ | Fold Difference |
|---|---|---|---|---|
| DMSO | 2.5 | 0.610 | Not determined | |
| GI254025X | 1.7 | 0.989 | 100 | 1 |
| SRI-028607 | 0.9 | 0.928 | 56 | 1.8 |
| SRI-028608 | 1.8 | 0.833 | 105 | 0.9 |
| SRI-028609 | 0.4 | 0.962 | 21 | 4.8 |
| SRI-028610 | 2.6 | 0.885 | 151 | 0.7 |
| SRI-028611 | Ambiguous | | Not determined | |

D

| Treatment | IC$_{50}$ (uM) | R$^2$ | % GI254023X IC$_{50}$ | Fold Difference |
|---|---|---|---|---|
| DMSO | >1000 | 0.139 | Not determined | |
| GI254023X | 4.6 | 0.829 | 100 | 1 |
| SRI-028619 | 8.6 | 0.909 | 186 | 0.5 |
| SRI-028621 | 6.2 | 0.949 | 134 | 0.7 |

| Treatment | IC$_{50}$ (µM) | R$^2$ | % GI254023X IC$_{50}$ | Fold Difference |
|---|---|---|---|---|
| DMSO | 0.14 | 0.184 | Not determined | |
| GI254023X | 1.97 | 0.828 | 100 | 1 |
| SRI-028751 | 4.52 | 0.967 | 230 | 0.43 |
| SRI-028753 | 3.42 | 0.977 | 174 | 0.57 |
| SRI-028754 | 2.39 | 0.659 | 121 | 0.83 |
| SRI-028755 | 13.39 | 0.735 | 679 | 0.15 |

B

| Treatment | IC$_{50}$ (µM) | R$^2$ | % GI254023X IC$_{50}$ | Fold Difference |
|---|---|---|---|---|
| DMSO | | | Not determined | |
| GI254023X | 2.04 | 0.960 | 100 | 1 |
| SRI-028777 | 20.48 | 0.840 | Not determined | |
| SRI-028778 | 35.35 | 0.934 | Not determined | |
| SRI-028854 | 44.29 | 0.957 | Not determined | |
| SRI-028855 | 45.67 | 0.970 | Not determined | |

C

| Treatment | IC50 ± SEM (µM) | % GI254023X IC50 | Fold Difference |
|---|---|---|---|
| SRI-028594 (GI254023X) | 1.42 ± 0.05 | 100 | 1 |
| SRI-028597 | 6.98 ± 1.38 | 491 | 0.2 |
| SRI-028603 | 1.51 ± 0.23 | 106 | 0.9 |
| SRI-028607 | 3.34 ± 0.34 | 235 | 0.4 |
| SRI-028608 | 8.17 ± 0.70 | 575 | 0.2 |
| SRI-028609 | 1.93 ± 0.36 | 135 | 0.7 |
| SRI-028610 | 6.26 ± 0.34 | 440 | 0.2 |
| SRI-028619 | 3.23 ± 0.20 | 227 | 0.4 |
| SRI-028621 | 2.96 ± 0.27 | 208 | 0.5 |
| SRI-028751 | 5.10 ± 0.65 | 359 | 0.3 |
| SRI-028753 | 4.65 ± 0.60 | 327 | 0.3 |

FIG. 13A-C

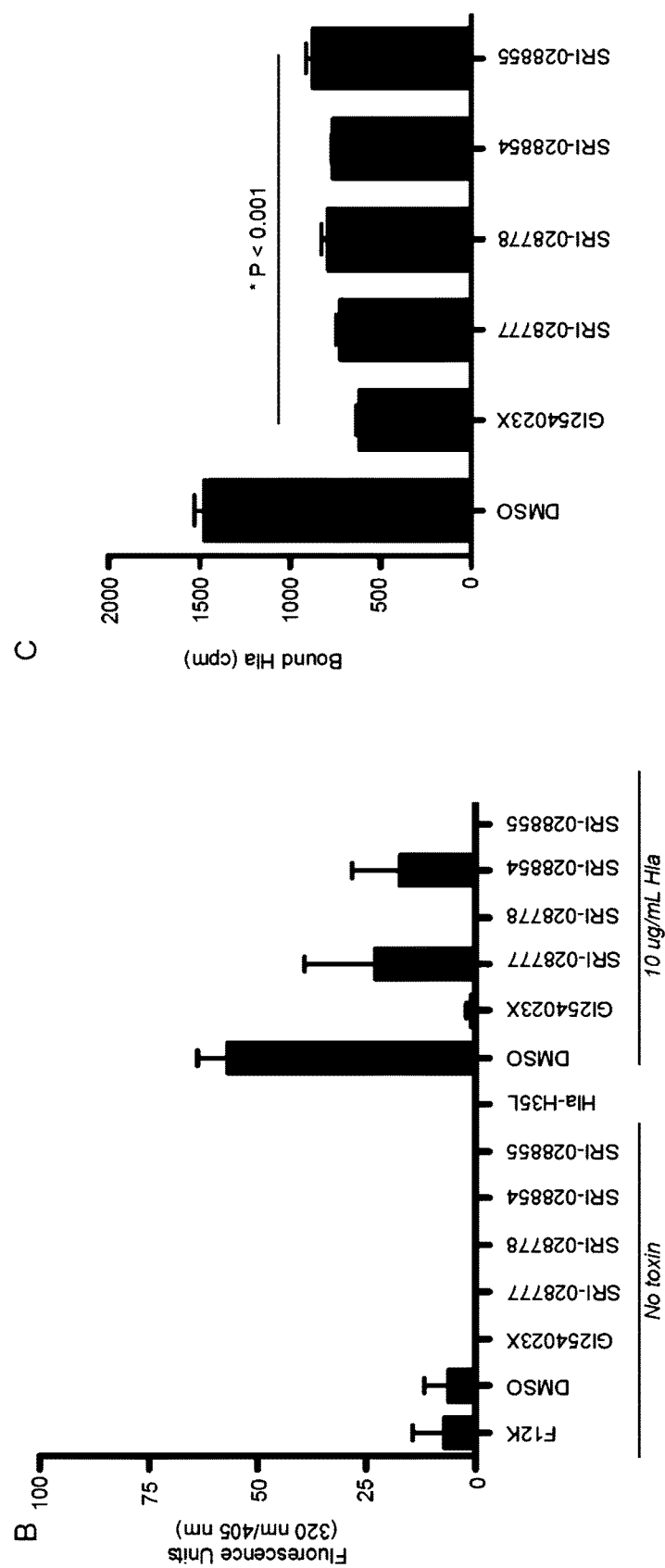
FIG. 14B-C

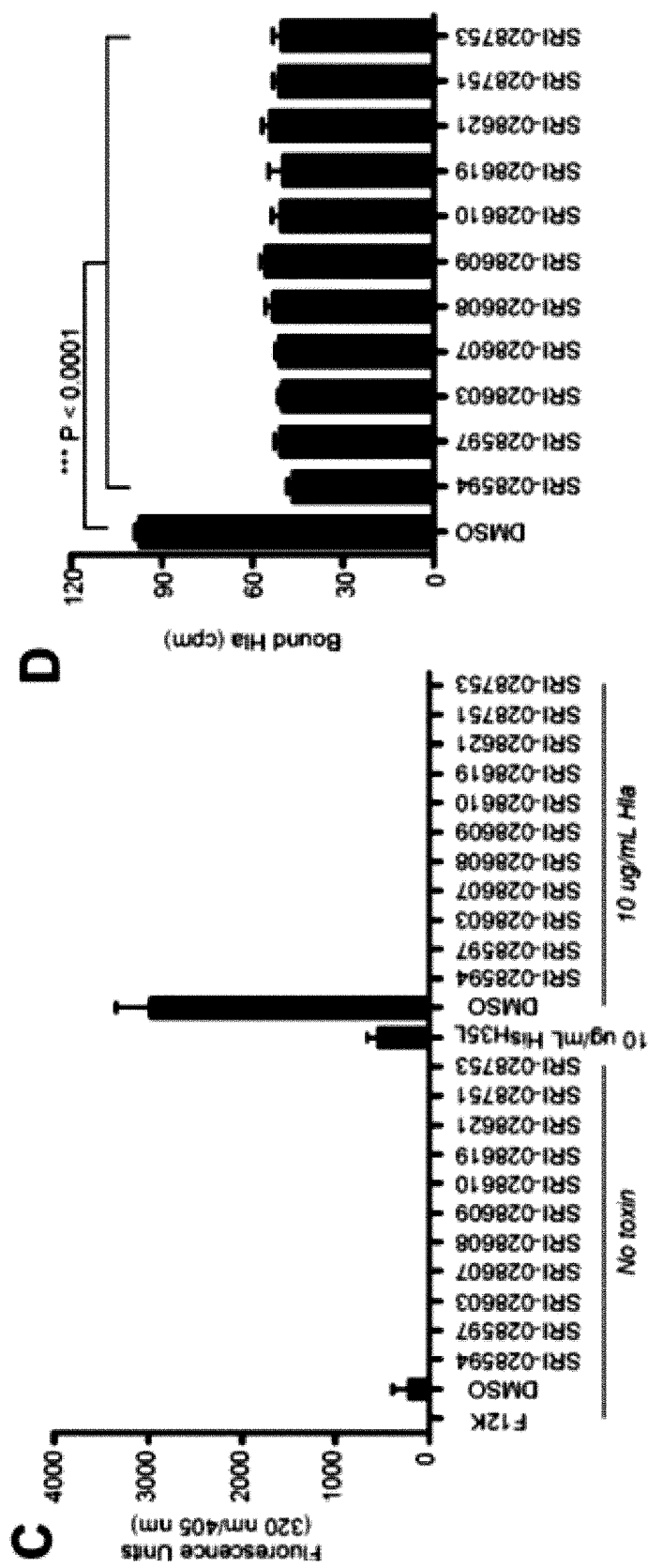
FIG. 15C-D

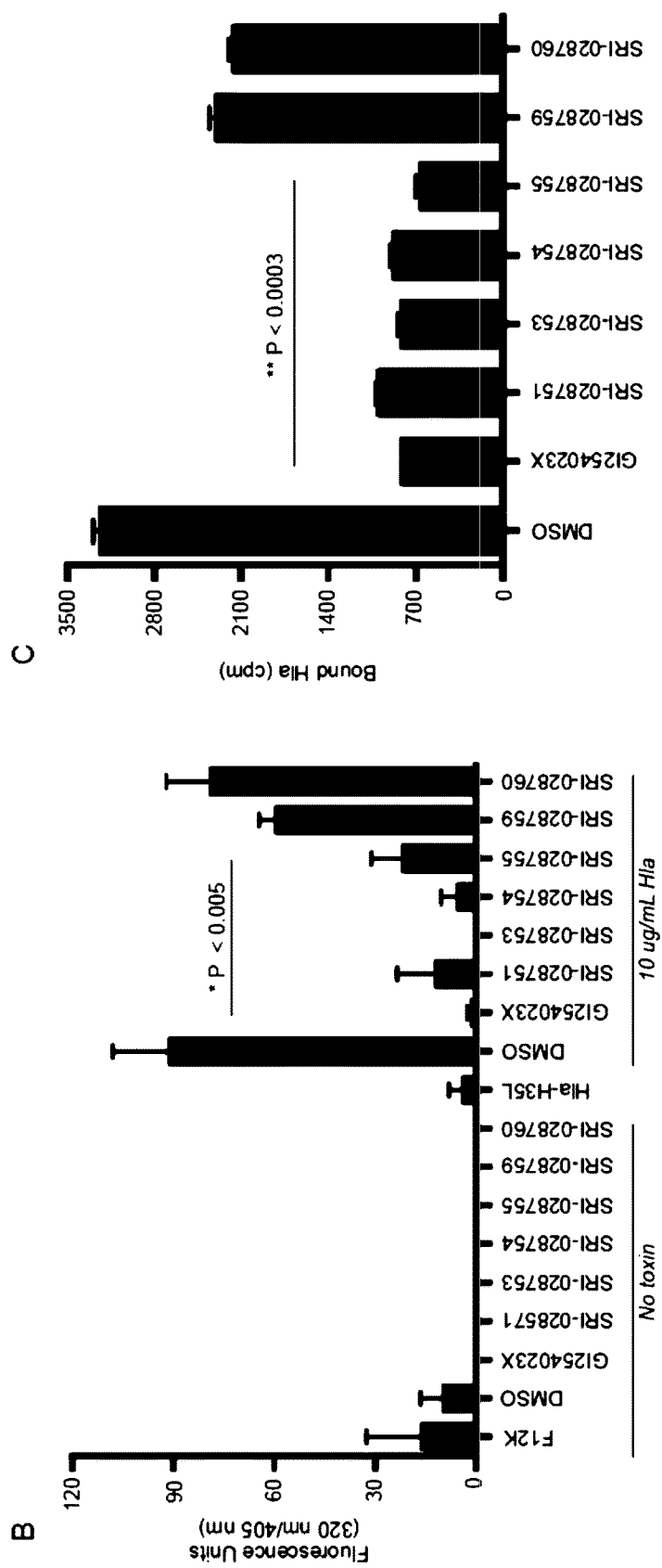
FIG. 17B-C

METHODS AND COMPOSITIONS USING ADAM10 INHIBITORS TO TREAT BACTERIAL INFECTIONS

CROSS-REFERENCE TO RELATED APPLICATIONS

This application is a national phase application under 35 U.S.C. § 371 of International Application No. PCT/US2014/032959, filed on Apr. 4, 2014, which claims the benefit of priority of U.S. Provisional Patent Application No. 61/809,064, filed on Apr. 5, 2013. The entire contents of each of the above-referenced disclosures are specifically incorporated herein by reference without disclaimer.

STATEMENT OF GOVERNMENT RIGHTS

This invention was made with government support under grant numbers AI057153, AI097434, and HHSN272201100022I awarded by the National Institutes of Health. The government has certain rights in this invention.

BACKGROUND OF THE INVENTION

A. Field of the Invention

Embodiments of this invention are directed generally to microbiology and medicine. In certain aspects the invention is directed to treatment of *Staphylococcus* and *Streptococcus* infection.

B. Description of Related Art

The number of both community acquired and hospital acquired infections have increased over recent years with the increased use of intravascular devices. Hospital acquired (nosocomial) infections are a major cause of morbidity and mortality, particularly in the United States, where it affects more than 2 million patients annually. The most frequent infections are urinary tract infections (33% of the infections), followed by pneumonia (15.5%), surgical site infections (14.8%) and primary bloodstream infections (13%) (Emori and Gaynes, 1993).

The major nosocomial pathogens include *Staphylococcus aureus*, coagulase-negative Staphylococci (mostly *Staphylococcus epidermidis*), enterococcus spp., *Escherichia coli*, *Clostridium difficile* and *Pseudomonas aeruginosa*. Although these pathogens cause approximately the same number of infections, the severity of the disorders they can produce combined with the frequency of antibiotic resistant isolates balance this ranking towards *S. aureus* and *S. epidermidis* as being the most significant nosocomial pathogens. Staphylococci can cause a wide variety of diseases in humans and other animals through either toxin production or invasion.

Epithelial barriers are a potent host defense against invasive bacterial infection. Pathogens circumvent this barrier through virulence factors that target specific structural elements of the epithelium, impairing its integrity (Kim et al., 2010). Critical bacterial targets within the epithelium include focal adhesion complexes, apical tight junction proteins, and the cadherin:catenin protein complex that comprises the adherens junction. *Staphylococcus aureus* is a leading cause of bacteremia, pneumonia, skin and soft tissue infection and lethal toxin-mediated syndromes (Lowy, 1998). This organism exhibits a dual interaction with its human host, existing as a harmless skin commensal and deadly invasive pathogen armed with multiple virulence factors. *S. aureus* alpha-hemolysin (Hla) is a pore-forming cytotoxin that contributes to the pathogenesis of pneumonia, dermonecrotic skin infection, and corneal infection (O'Callaghan et al., 1997; Kennedy et al., 2010; Bubeck Wardenburg et al., 2007a, 2007b). Further, Hla potentiates the penetration of *S. aureus* toxic shock syndrome toxin across the vaginal epithelium (Brosnahan et al., 2009).

A significant clinical burden of *S. aureus* skin infection is also apparent in individuals with several immunodeficiency states and atopic dermatitis, a chronic disease in which up to 90% of afflicted patients harbor *S. aureus* in lesional and non-lesional skin (Ong and Leung, 2010). Host defense against *S. aureus* skin infection is multifaceted, relying most importantly on local innate immunologic control through $T_H17$ and IL-1β driven recruitment of neutrophils in addition to the protective actions of β-defensins and the cutaneous barrier. Pathogen virulence in acute staphylococcal infection is likewise multifactorial, relying in part on α-hemolysin (Hla), a pore-forming cytotoxin secreted by almost all strains of *S. aureus* (Bhakdi and Tranum-Jensen, 1991). Hla is required for dermonecrotic changes in skin infection, also contributing positively to abscess size (Kennedy et al., 2010; Patel et al., 1987). Immunization strategies targeting Hla afford protection against dermonecrosis (Kennedy et al., 2010). Indeed, *S. aureus* is the most common bacterial pathogen that complicates atopic dermatitis lesions (Ong and Leung, 2010), demonstrated to express the V8 protease and immunomodulatory virulence factors that have also been described to adversely impact on epithelial barrier function.

There remains a need to develop effective compositions and treatments for staphylococcal and other pathogenic bacterial infections.

SUMMARY OF THE INVENTION

*Staphylococcus aureus* remains a leading cause of infectious disease morbidity and mortality. This human commensal must breach the innate epithelial barrier defense to cause invasive disease. The highly conserved pore-forming cytotoxin α-hemolysin (Hla) injures diverse epithelial cells by interacting with the zinc-dependent metalloprotease ADAM10 as its receptor. Alveolar epithelial exposure to α-hemolysin upregulates cellular ADAM10 enzymatic activity, resulting in E-cadherin cleavage. This cleavage event causes a physiologic disruption of epithelial barrier function, associated with both acute lung injury and penetration of toxic-shock syndrome toxin 1 (TSST-1) into the vaginal mucosal. Thus, a bacterial cytotoxin can usurp the activity of its receptor, leading to a direct and rapid modification of epithelial cell-cell contacts.

Certain embodiments are directed to small molecule inhibitors of ADAM10. In some embodiments, the inhibitor is a compound of the formula:

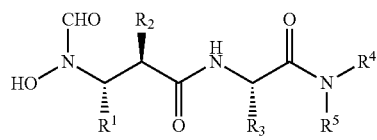

wherein $R^1$ is hydrogen, alkyl, halogen, haloalkyl, alkenyl, or alkynyl; $R^2$ is hydrogen, alkyl, benzyl, aryl, aralkyl, functionalized aralkyl, alkenyl, or alkynyl; $R^3$ is hydrogen, alkyl, benzyl, aryl, alkenyl, or alkynyl; $R^4$ is hydrogen, alkyl, substituted alkyl, cycloalkyl, substituted cycloalkyl, 2-ethoxyethyl, 2-isopropoxyethyl, 1-methoxybutan-2-yl, (tetrahydrofuran-2-yl)methyl, 2-(piperidin-1-yl)ethyl, 2-(N-sulfonylmorpholine)ethyl, 2-(N,N-dimethyl)ethyl, 2-hydroxyethyl, 2-(N-morphonline)ethyl, or a heterocycle; and $R^5$ is hydrogen or methyl, or a salt, prodrug, enantiomer, or diastereomer thereof. In some embodiments, $R^1$ is methyl. In some embodiments, $R^2$ is aralkyl or functionalized aralkyl. In some embodiments, $R^3$ is tert-butyl. In some embodiments, $R^4$ is methyl. In some embodiments, $R^5$ is hydrogen. In some embodiments, the compound is further defined as:

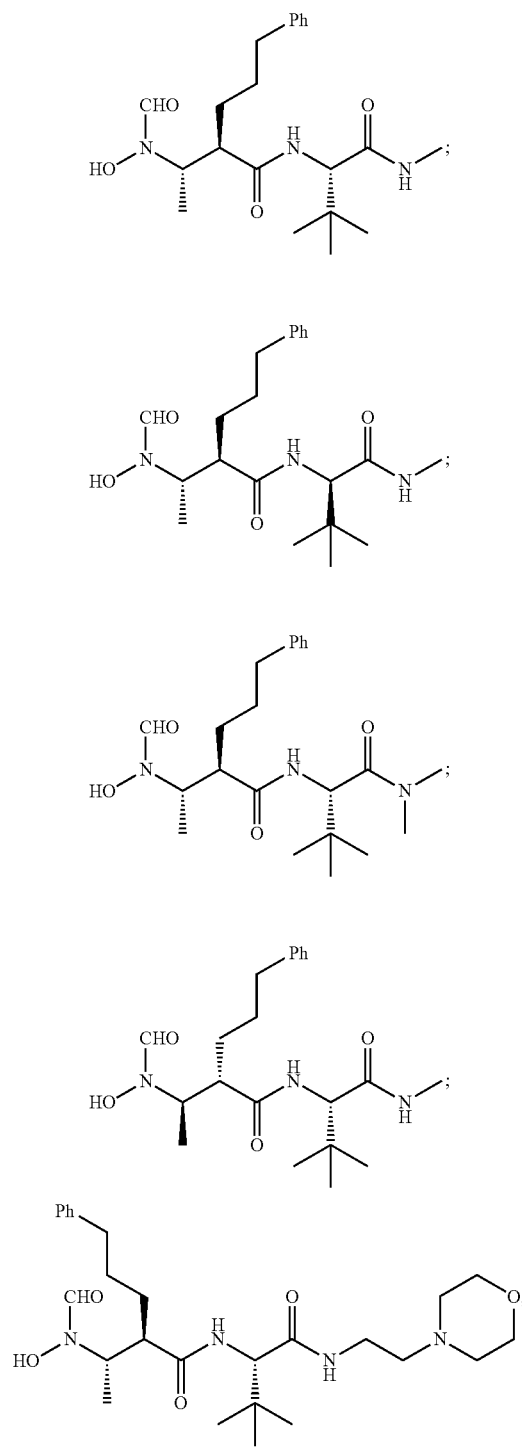

-continued

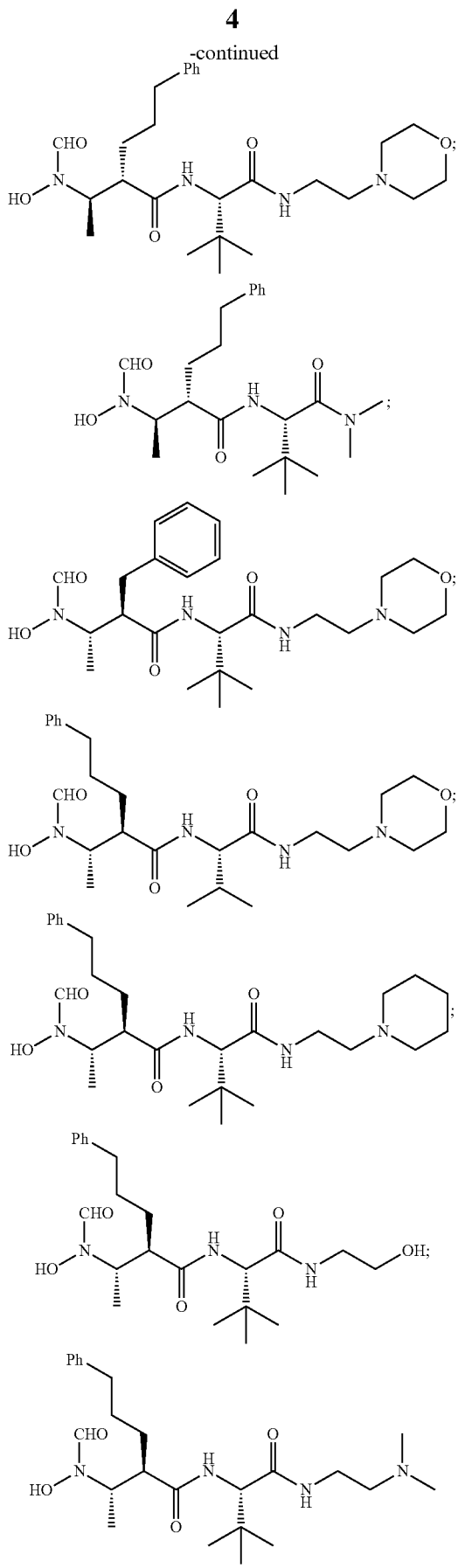

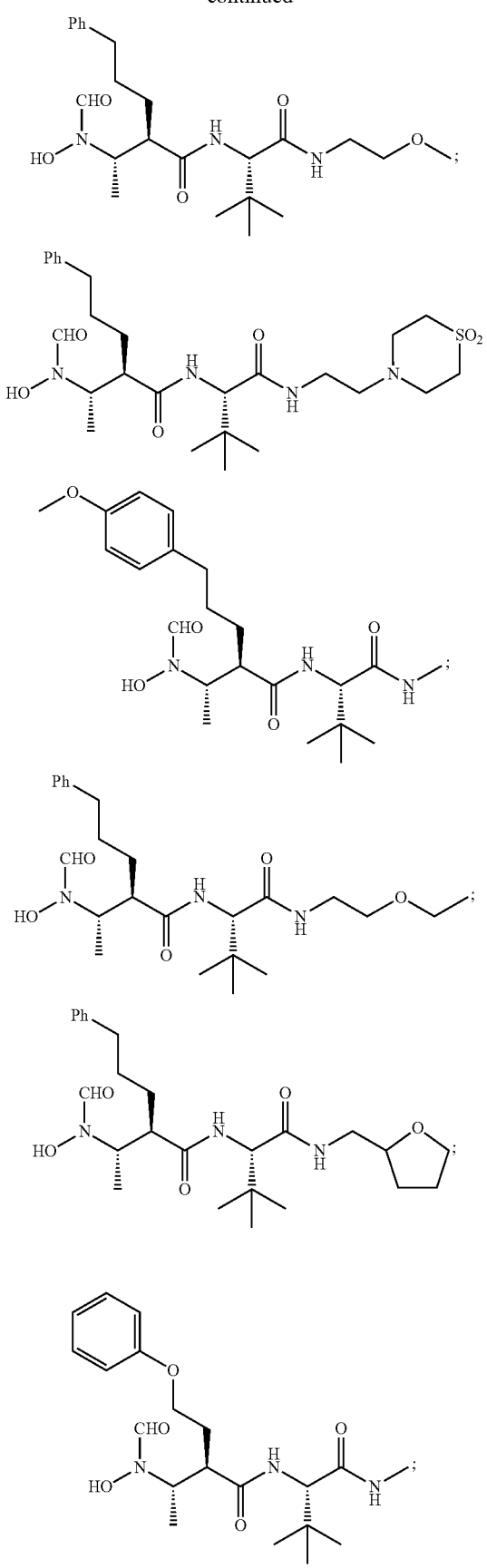
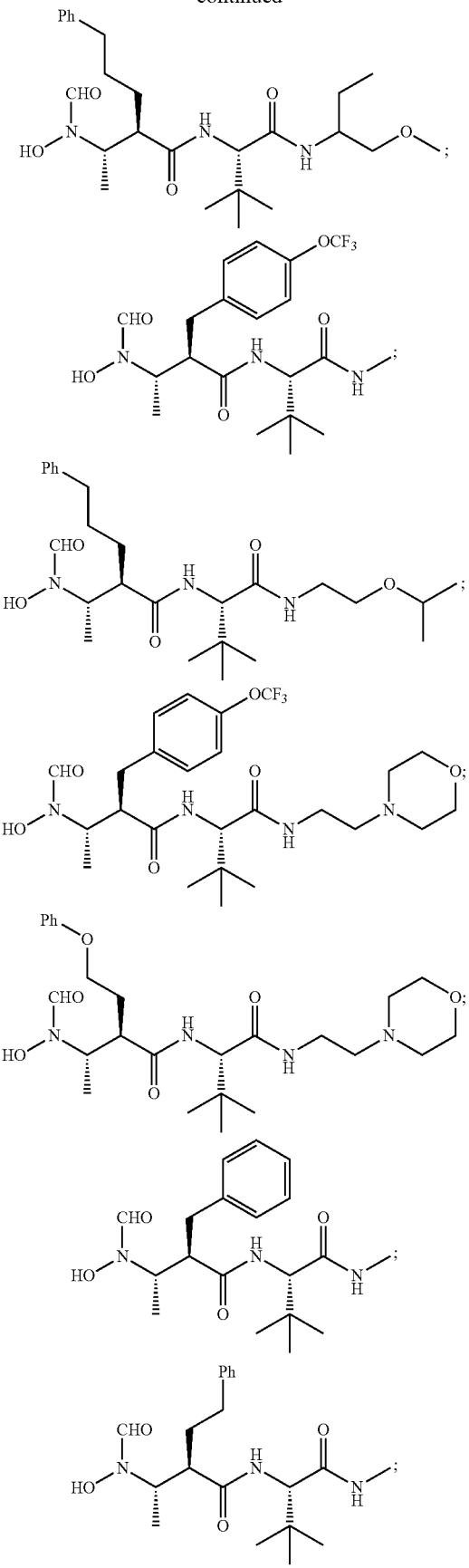

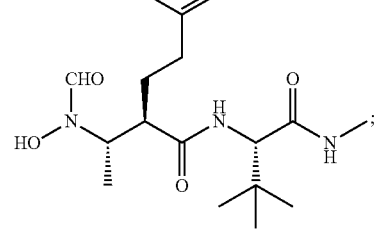
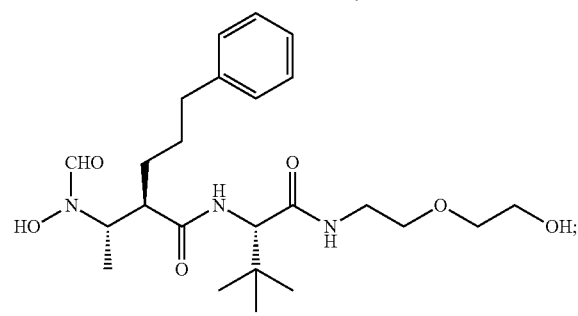
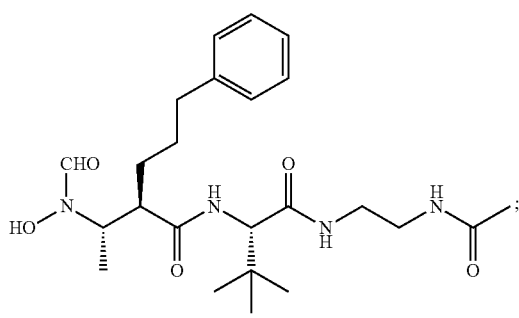
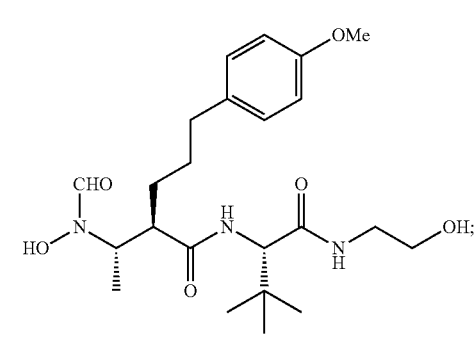
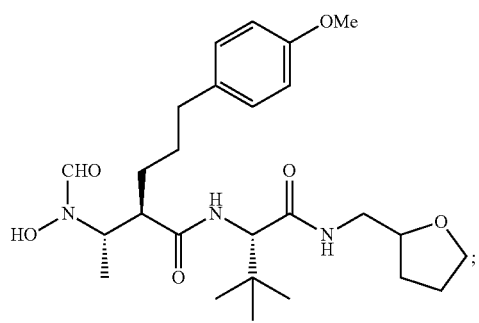
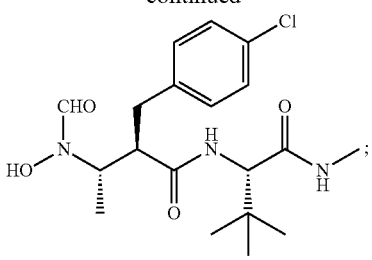
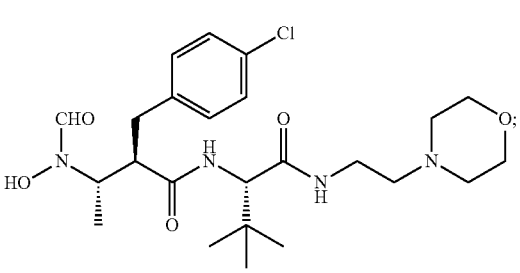
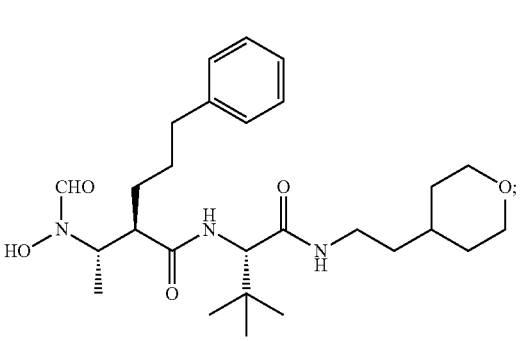
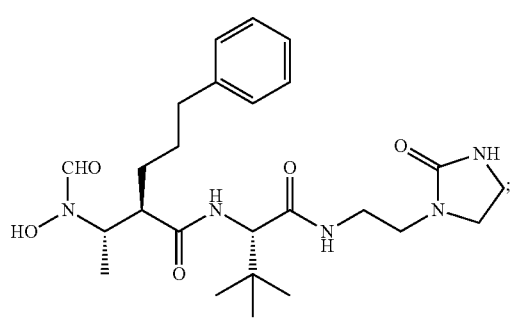
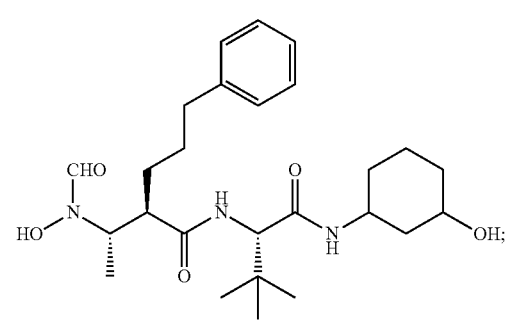

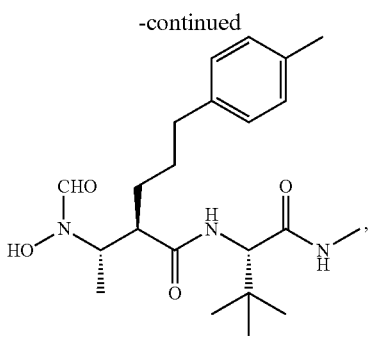

or salt, enantiomer or prodrug thereof.

Certain embodiments are directed to pharmaceutical compositions comprising any of the compounds or ADAM10 inhibitors disclosed herein, or a pharmaceutically acceptable salt, prodrug, enantiomer, or diastereomer thereof, and an excipient.

Certain embodiments are directed to methods of inhibiting Staphylococcal infection comprising administering an effective amount of an ADAM10 inhibitor to a patient. Other embodiments concern methods of inhibiting infection by a bacteria from the genus *Clostridium, Streptococcus, Listeria, Bacillus*, or *Arcanobacterium*.

The methods can include a method of preventing or treating a Staphylococcal infection in a patient, or a method of treating a subject having or at risk of developing a Staphylococcal infection, comprising administering an effective amount of an ADAM10 inhibitor to the subject. In some embodiments, the ADAM10 inhibitor is a compound as disclosed herein.

The methods can also include treating pore-forming toxin-inducted pathology in a subject comprising administering an ADAM10 inhibitor to a subject exposed to a pore-forming toxin. In certain embodiments, the pathology is related to infection by a species of the genus *Clostridium, Streptococcus, Listeria, Bacillus*, or *Arcanobacterium*. In certain embodiments, the pathology is related to infection by a species of the genus *Stapholococcus*. In some embodiments, the ADAM10 inhibitor is a compound as disclosed herein.

In some embodiments, the pore-forming toxin is alpha-hemolysin (Hla). In certain methods, the Hla induced pathology is pulmonary edema, obliteration of alveolar space, skin lesions, sepsis, and toxic shock.

In additional embodiments, the pore-forming toxin is pneumolysin (PLY) or Streptolysin O (SLO). In certain methods, the PLY-induced pathology is pulmonary edema, obliteration of alveolar space, skin lesions, sepsis, and toxic shock.

The methods can also include inhibiting pore-forming toxin-induced cleavage of cadherins in a subject comprising administering an ADAM10 inhibitor to a subject exposed to a pore-forming toxin. In some embodiments, the pore-forming toxin is Hla. In additional embodiments, the pore-forming toxin is PLY or SLO.

The methods can also include ameliorating disruption of an epithelial membrane comprising contacting an epithelial membrane that has been exposed to a pore-forming toxin with an ADAM10 inhibitor. In some embodiments, the pore-forming toxin is Hla. In additional embodiments, the pore-forming toxin is PLY or SLO. In further embodiments, the pore-forming toxin is from a bacteria species of the genus *Clostridium, Streptococcus, Listeria, Bacillus*, or *Arcanobacterium*. In some embodiments, the ADAM10 inhibitor is a compound as disclosed herein.

The methods can also include ameliorating disruption of an endothelial membrane comprising contacting an endothelial membrane that has been exposed to a pore-forming toxin with an ADAM10 inhibitor. In some embodiments, the pore-forming toxin is Hla. In additional embodiments, the pore-forming toxin is PLY or SLO. In some embodiments, the ADAM10 inhibitor is a compound as disclosed herein.

The methods can also include inhibiting, attenuating, treating, or ameliorating toxic-shock syndrome and its related pathology.

The methods can also include ameliorating disruption of an epithelial membrane comprising contacting an epithelial membrane that has been exposed to alpha-hemolysin with an ADAM10 inhibitor. In certain embodiments, the alpha-hemolysin, PLY or SLO is from a pathogenic bacteria. In some embodiments, the ADAM10 inhibitor is a compound as disclosed herein.

Other embodiments include methods of treating pneumonia in a patient who has signs of pneumonia or has been diagnosed with or tested positive for pneumonia comprising administering a composition comprising a metalloprotease inhibitor to the patient. Embodiments include methods of treating pneumonia comprising administering an effective amount of an ADAM10 inhibitor to a patient, wherein the patient has been determined to have or be at risk of developing pneumonia caused by Staphylococcal infection or by *Streptococcus* infection. In some embodiments, the ADAM10 inhibitor is a compound as disclosed herein.

Additional embodiments include methods for treating or preventing atopic dermatitis lesions comprising administering an effective amount of an ADAM10 inhibitor to a patient. In some embodiments, the patient has been determined to have or be at risk for a Staphylococcal infection. In further embodiments, the patient exhibits an abscess, boil, or furuncle. In some embodiments, the ADAM10 inhibitor is a compound as disclosed herein.

Several embodiments concern methods for preventing or treating dermonecrosis in a patient comprising administering an effective amount of an ADAM10 inhibitor to the patient. In some embodiments, the patient has been determined to have or be at risk for a Staphylococcal infection. In further embodiments, the patient has been determined to have or be at risk for dermonecrosis. In further embodiments, the patient exhibits an abscess, boil, or furuncle. In some embodiments, the ADAM10 inhibitor is a compound as disclosed herein.

In further embodiments methods can include treating a subject having or at risk of developing a pharyngitis (e.g., a pharyngitis associated with *Arcanobacterium* infection) comprising administering an effective amount of an ADAM10 inhibitor to the subject. In some embodiments, the ADAM10 inhibitor is a compound as disclosed herein.

In certain embodiments, a method is provided for treating an domestic animal having or at risk of developing an infection with a bacterial pathogen described herein. For example, the method can comprising administering an ADAM10 inhibitor to the animal having or at risk of developing an infection. In some aspects, methods are provided for treating or preventing animal infections by bacteria expressing pore-forming toxins, in particular toxins subject to inhibition by an ADAM10 inhibitors. For example, methods according to the embodiments can comprise treating or preventing an *Arcanobacterium pyogenes* or *Staphylococcus aureus* infection in an animal by administering an ADAM10 inhibitor described herein. In some embodiments, the ADAM10 inhibitor is a compound as disclosed herein.

In certain embodiments a method is provided for treating a cow having or at risk of developing bovine mastitis (e.g., mastitis associated with *S. aureus* infection) comprising administering an effective amount of an ADAM10 inhibitor to the cow. In some embodiments, the ADAM10 inhibitor is a compound as disclosed herein.

In some embodiments, the subject has been determined to have or be at risk for a Staphylococcal infection. In some embodiments, the method further comprises monitoring the patient for a Staphylococcal infection within a week of administering the inhibitor.

In some embodiments, the patient is at risk of *Staphylococcus* infection. In some embodiments, the patient is immune deficient, is immunocompromised, is hospitalized, is undergoing an invasive medical procedure, is infected with influenza virus or is on a respirator. In some embodiments, the patient has pneumonia, sepsis, corneal infection, skin infection, infection of the central nervous system, or toxic shock syndrome. In some embodiments, the subject has been exposed to a pore-forming toxin. In some aspects the patient is not a patient having cancer, HIV or HCV infection.

In some embodiments, the patient is determined to have a Staphylococcal infection. In some embodiments, the method further comprises identifying the patient as having a Staphylococcal infection. In some embodiments, the method further comprises selecting the patient after the patient is diagnosed with a Staphylococcal infection. In some embodiments, the method further comprises testing the patient for a Staphylococcal infection. In some embodiments, the method further comprises obtaining from the patient a biological sample for testing whether the patient has a Staphylococcal infection. In some embodiments, the patient is administered the ADAM10 inhibitor within 1 week of being determined to have a Staphylococcal infection.

In some embodiments, the Staphylococcal infection is a Hla-mediated tissue injury. In some embodiments, the inhibitor inhibits the binding of Hla to ADAM10. In some embodiments, the Staphylococcal infection is a *Staphylococcus aureus* infection. In some embodiments, the *Staphylococcus aureus* infection is a drug resistant *Staphylococcus aureus* infection. In some embodiments, the drug resistant *Staphylococcus aureus* infection is a methicillin-resistant *Staphylococcus aureus* (MRSA) infection. In additional embodiments, the pathogenic bacterial infection is a *Streptococcus pneumoniae* infection.

In some embodiments, the method further comprises administering a second ADAM10 inhibitor or a second anti-microbial treatment. The second inhibitor or treatment can be administered in the same composition or in separate compositions. In some embodiments, the first inhibitor or treatment is administered, and the second inhibitor or treatment is administered. In some embodiments, the second inhibitor or treatment is administered within 3 days of the first inhibitor or treatment. In some embodiments, the second inhibitor or treatment is administered within 24 hours of the first inhibitor or treatment. In some embodiments, the second inhibitor or treatment is administered within 3 hours of the first inhibitor or treatment. In some embodiments, the second anti-microbial treatment is an antibiotic agent, an anti-infective agent, a passive vaccine or an active vaccine.

The compositions may be administered in any appropriate manner. In some embodiments, the composition is administered orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, via localized perfusion, bathing target cells directly, or any combination thereof. In some embodiments, the administration is topical.

Methods may involve administering a composition containing about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mcg), milligrams (mg), or grams of an ADAM10 inhibitor, or any range derivable therein.

Alternatively, embodiments may involve providing or administering to the patient or to cells or tissue of the patient about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mcg), milligrams (mg), or grams of ADAM10 inhibitor, or any range derivable therein, in one dose or collectively in multiple doses. In some embodiments, the composition comprises between about 0.1 ng and about 2.0 g of ADAM10 inhibitor.

Alternatively, the composition may have a concentration of ADAM10 inhibitor that is 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 micrograms/ml or mg/ml, or any range derivable therein.

If a liquid, gel, or semi-solid composition, the volume of the composition that is administered to the patient may be about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 microliters (μl) or milliliters (ml), or any range derivable therein. In certain embodiments, the patient is administered up to about 10 ml of the composition.

The amount of ADAM10 inhibitor that is administered or taken by the patient may be based on the patient's weight (in kilograms). Therefore, in some embodiments, the patient is administered or takes a dose or multiple doses amounting to about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 micrograms/ kilogram (kg) or mg/kg, or any range derivable therein.

The composition may be administered to (or taken by) the patient 1, 2, 3, 4, 5, 6, 7, 8, 9, 10, 11, 12, 13, 14, 15, 16, 17, 18, 19, 20 or more times, or any range derivable therein, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range derivable therein. It is specifically contemplated that the composition may be administered once daily, twice daily, three times daily, four times daily, five times daily, or six times daily (or any range derivable therein) and/or as needed to the patient. Alternatively, the composition may be administered every 2, 4, 6, 8, 12 or 24 hours (or any range derivable therein) to or by the patient. In some embodiments, the patient is administered the composition for a certain period of time or with a certain number of doses after experiencing symptoms of a pathogenic bacterial infection.

A patient is a human patient. It is contemplated that any embodiment involving a patient may also be applied to a subject, which refers to any organism that suffers physiologically as a result from infection by *Staphylococcus*. In certain embodiments, the subject is a mammal, which includes but is not limited to dogs, cats, cows, horses, pigs, monkeys, and sheep. In certain aspects, the patient is not a patient that has been determined to have cancer or that is under treatment for cancer. In some aspects, the subject is defined as a subject that has not been determined to have an HIV or HCV infection.

Certain embodiments are directed to methods where the patient is immune deficient, is immunocompromised, is hospitalized, is undergoing an invasive medical procedure, has a respiratory infection, is infected with influenza virus or is on a respirator. For example, the patient can have a bacterial or viral respiratory infection, such as an infection associated with human respiratory syncytial virus (RSV), influenza virua, parainfluenza virus, rhinovirus or adenovirus.

In still a further aspect the patient has a *Staphylococcus* infection, which includes but is not limited to pneumonia, sepsis, bacteremia, corneal infection, skin infection, infection of the central nervous system, or toxic shock syndrome.

Any embodiments discussed in the context of *Staphylococcus* infection can be implemented with *Streptococcus* infection, as well as infection with *Clostridium, Streptococcus, Listeria, Bacillus,* or *Arcanobacterium*. This includes, but is not limited to, infection by a specific species of these bacteria, such as *Streptococcus intermedius, Streptococcus pyogenes, Clostridium septicum*, and *Listeria monocytogenes*.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The compounds may be administered by any acceptable route. In some embodiments, the compounds are administered orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, via localized perfusion, bathing target cells directly, or any combination thereof. In some embodiments, the administration is topical.

The compositions may be administered one or more times. In some embodiments, the compositions are administered 1, 2, 3, 4, 5, 6, 7, 8, 9, or 10 times or more.

"Effective amount" or "therapeutically effective amount" or "pharmaceutically effective amount" means that amount which, when administered to a subject or patient for treating a disease, is sufficient to effect such treatment for the disease. In some embodiments, the subject is administered at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, or 100 mg/kg (or any range derivable therein).

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (P. H. Stahl & C. G. Wermuth eds., *Verlag Helvetica Chimica Acta,* 2002).

Throughout this application, the term "about" is used to indicate that a value includes the inherent variation of error for the measurement or quantitation method.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. Compositions and methods "consisting essentially of" any of the ingredients or steps disclosed limits the scope of the claim to the specified materials or steps which do not materially affect the basic and novel characteristic of the claimed invention.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2B is a graph depicting inhibition of Hla-induced ADAM10 metalloprotease activity in response to administration of GI254023X and three ADAM10 inhibitors with inverted R1 stereochemistry. FIG. 2C is a graph depicting inhibition of binding of radiolabelled Hla to A549 cells by GI254023X. Three Hla inhibitors with inverted R1 stereochemistry were less effective at inhibiting binding. FIG. 2D includes the three ADAM10 inhibitors with inverted R1 stereochemistry.

FIG. 3B is a graph depicting inhibition of Hla-induced ADAM10 metalloprotease activity in response to administration of GI254023X and an ADAM10 inhibitor with inverted R3 stereochemistry. FIG. 3C is a graph depicting inhibition of binding of radiolabelled Hla to A549 cells by GI254023X. An ADAM10 inhibitor with inverted R3 stereochemistry was less effective at inhibiting binding. FIG. 3D is the ADAM10 inhibitor with inverted R3 stereochemistry.

FIG. 4B is a graph depicting inhibition of Hla-induced ADAM10 metalloprotease activity in response to administration of four ADAM10 inhibitors with carbon chains of varying length at the R2 position. FIG. 4C is a graph depicting inhibition of binding of radiolabelled Hla to A549 cells in response to four ADAM10 inhibitors with carbon chains of varying length at the R2 position. FIG. 4D includes the four ADAM10 inhibitors with carbon chains of varying length at the R2 position.

FIG. 5B is a graph depicting inhibition of Hla-induced ADAM10 metalloprotease activity in response to administration of four ADAM10 inhibitors. FIG. 5C is a graph depicting inhibition of binding of radiolabelled Hla to A549 cells in response to four ADAM10 inhibitors. FIG. 5D includes the four ADAM10 inhibitors.

FIG. 6B is a graph depicting inhibition of Hla-induced ADAM10 metalloprotease activity in response to administration of five ADAM10 inhibitors. FIG. 6C is a graph depicting inhibition of binding of radiolabelled Hla to A549 cells in response to five ADAM10 inhibitors. FIG. 6D is a rabbit erythrocyte hemolysis dose-response assay in response to administration of five ADAM10 inhibitors. FIG. 6E is a table of the activities (IC50, µM) of GI254023X and five ADAM10 inhibitors, and comparison of the inhibitory activities of the five ADAM10 inhibitors to GI254023X.

FIGS. 7A-D FIG. 7A is a graph depicting inhibition of Hla-induced (0, 10, and 20 µg/mL) eukaryotic cell death in response to GI254023X and eight ADAM10 inhibitors. FIG. 7B is a graph depicting inhibition of Hla-induced ADAM10 metalloprotease activity in response to administration of eight ADAM10 inhibitors. FIG. 7C is a graph depicting inhibition of binding of radiolabelled Hla to A549 cells in response to eight ADAM10 inhibitors. FIG. 7D is a graph depicting results of a hemolysis assay with GI254023X and eight ADAM10 inhibitors.

FIGS. 8A-D FIG. 8A is a graph depicting inhibition of Hla-induced (0, 10, and 20 µg/mL) eukaryotic cell death in response to GI254023X and five ADAM10 inhibitors. FIG. 8B is a graph depicting inhibition of Hla-induced ADAM10 metalloprotease activity in response to administration of five ADAM10 inhibitors. FIG. 8C is a graph depicting inhibition of binding of radiolabelled Hla to A549 cells in response to five ADAM10 inhibitors. FIG. 8D is a graph depicting results of a hemolysis assay with GI254023X and five ADAM10 inhibitors.

FIGS. 9A-D FIG. 9A is a graph depicting inhibition of Hla-induced (0, 10, and 20 µg/mL) eukaryotic cell death in response to GI254023X and five ADAM10 inhibitors. FIG. 9B is a graph depicting inhibition of Hla-induced ADAM10 metalloprotease activity in response to administration of five ADAM10 inhibitors. FIG. 9C is a graph depicting inhibition of binding of radiolabelled Hla to A549 cells in response to five ADAM10 inhibitors. FIG. 9D is a graph depicting results of a hemolysis assay with GI254023X and five ADAM10 inhibitors.

FIGS. 10A-D FIG. 10A is a graph depicting inhibition of Hla-induced (0, 10, and 20 µg/mL) eukaryotic cell death in response to GI254023X and six ADAM10 inhibitors. FIG. 10B is a graph depicting inhibition of Hla-induced ADAM10 metalloprotease activity in response to administration of six ADAM10 inhibitors. FIG. 10C is a graph depicting inhibition of binding of radiolabelled Hla to A549 cells in response to six ADAM10 inhibitors. FIG. 10D is a graph depicting results of a hemolysis assay with GI254023X and six ADAM10 inhibitors.

FIGS. 11A-D FIG. 11A is a table comparing $IC_{50}$ values for the listed ADAM10 inhibitors determined from the rabbit erythrocyte hemolysis assay. FIG. 11B is a table comparing $IC_{50}$ values for the listed ADAM10 inhibitors determined from the rabbit erythrocyte hemolysis assay. FIG. 11C is a table comparing $IC_{50}$ values for the listed ADAM10 inhibitors determined from the rabbit erythrocyte hemolysis assay. FIG. 11D is a table comparing $IC_{50}$ values for the listed ADAM10 inhibitors determined from the rabbit erythrocyte hemolysis assay.

FIGS. 13A-C FIG. 13A is a table comparing IC50 values for the listed ADAM10 inhibitors determined from the rabbit erythrocyte hemolysis assay. FIG. 13B is a table comparing IC50 values for the listed ADAM10 inhibitors determined from the rabbit erythrocyte hemolysis assay. FIG. 13C is a table comparing IC50 values for the listed ADAM10 inhibitors determined from the rabbit erythrocyte hemolysis assay. These data were collected in the presence of 0.375 μg/mL Hla and completed in triplicate.

FIGS. 14A-D FIG. 14A is a table of eukaryotic cell death measured by lactate dehydrogenase release. FIG. 14B is a table comparing the effects of Hla and ADAM10 inhibitors on an ADAM10 metalloprotease assay. FIG. 14C is a table that illustrates binding of radiolabelled Hla to A549 cells in the presence of ADAM10 inhibitors. FIG. 14D is a table demonstrating hemolysis of rabbit erythrocytes by Hla in the presence of ADAM10 inhibitors. Titrations of each inhibitor were used to calculate IC50 values listed in Table 6. Data are presented as mean±SEM and asterisks denote significance as determined by the student's T-test. Inhibitors were used at 20 μM unless other wise noted.

FIGS. 15A-D FIG. 15A depicts structures of various inhibitors. FIG. 15B is a table of eukaryotic cell death measured by lactate dehydrogenase release. Data are presented as mean±SEM and asterisks denote significance as determined by the student's T-test. FIG. 15C is a table comparing the results of an ADAM10 metalloprotease assay in the presence of Hla and ADAM10 inhibitors. Data are presented as mean±SEM. FIG. 15D is a table that depicts binding of radiolabelled Hla to A549 cells in the presence of ADAM10 inhibitors. Data are presented as mean±SEM and asterisks denote significance as determined by one-way ANOVA with a Dunnett's Multiple Comparison post-hoc test.

FIG. 16B is a graphical representation of the IC50 values for certain inhibitors compared to the parent compound. Data are presented as mean±SEM and asterisks denote significance as determined by one-way ANOVA with a Dunnett's Multiple Comparison post-hoc test.

FIGS. 17A-D FIG. 17A is a graph depicting eukaryotic cell death measured by lactate dehydrogenase release. FIG. 17B is a table comparing the effects of Hla and ADAM10 inhibitors on an ADAM10 metalloprotease assay. FIG. 17C is a table that illustrates binding of radiolabelled Hla to A549 cells in the presence of ADAM10 inhibitors. FIG. 17D is a table demonstrating hemolysis of rabbit erythrocytes by Hla in the presence of ADAM10 inhibitors. Titrations of each inhibitor were used to calculate IC50 values listed in Table 5. Data are presented as mean±SEM and asterisks denote significance as determined by the student's T-test. Inhibitors were used at 20 μM unless other wise noted at SRI-028594 is equivalent to GI254023X.

DESCRIPTION OF ILLUSTRATIVE EMBODIMENTS

Figure 1:
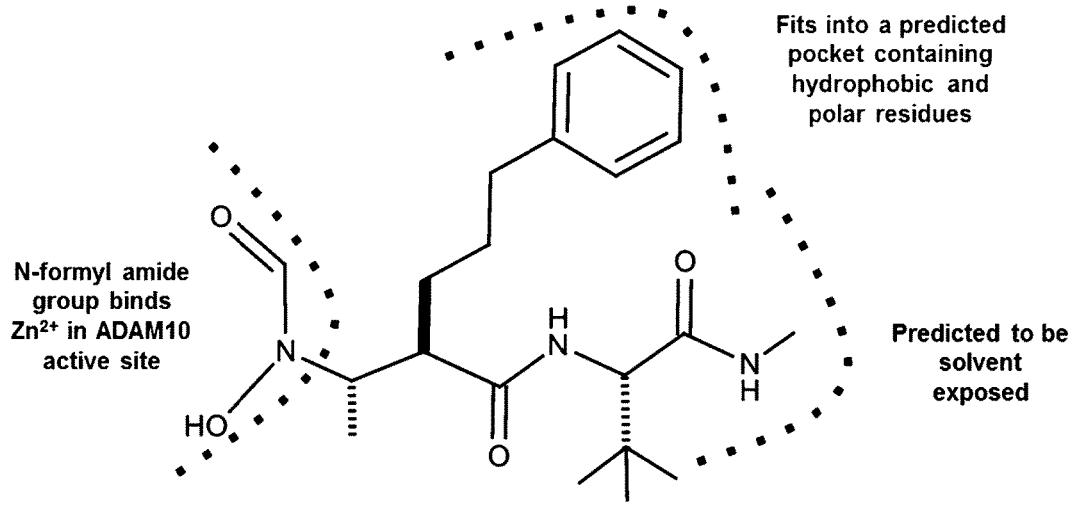
FIG. 1 depicts predicted interactions between GI254023X functional groups and ADAM.
Figure 2A:
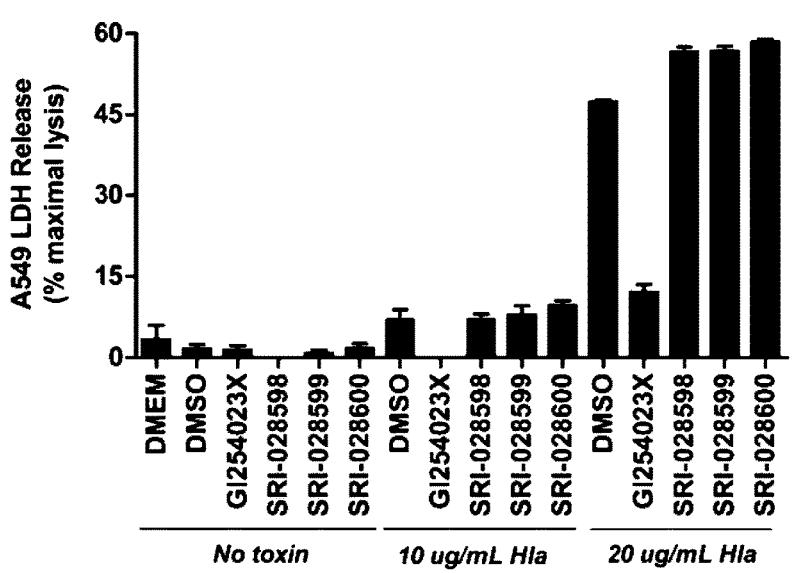
FIGS. 2A-D FIG. 2A is a graph depicting inhibition of Hla-induced (0, 10, and 20 µg/mL) eukaryotic cell death in response to GI254023X and three ADAM10 inhibitors with inverted R1 stereochemistry.
Figure 2B:
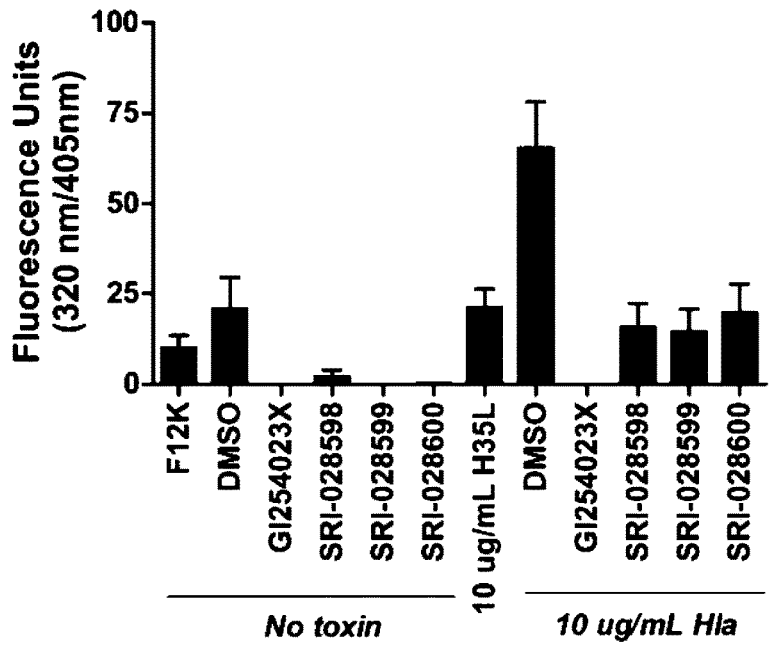
Figure 2C:
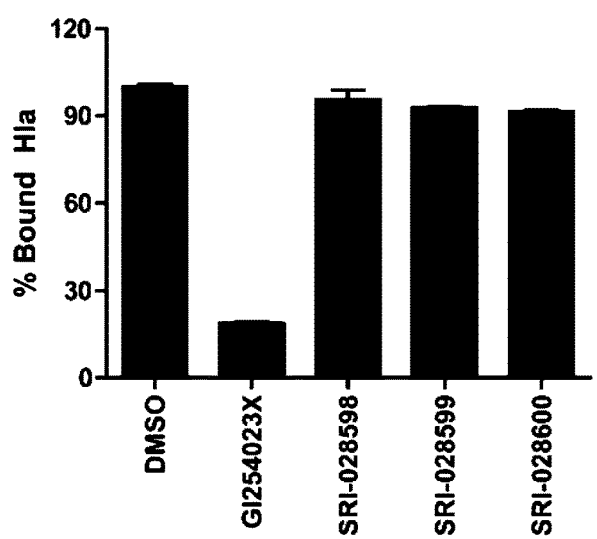
Figure 2D:
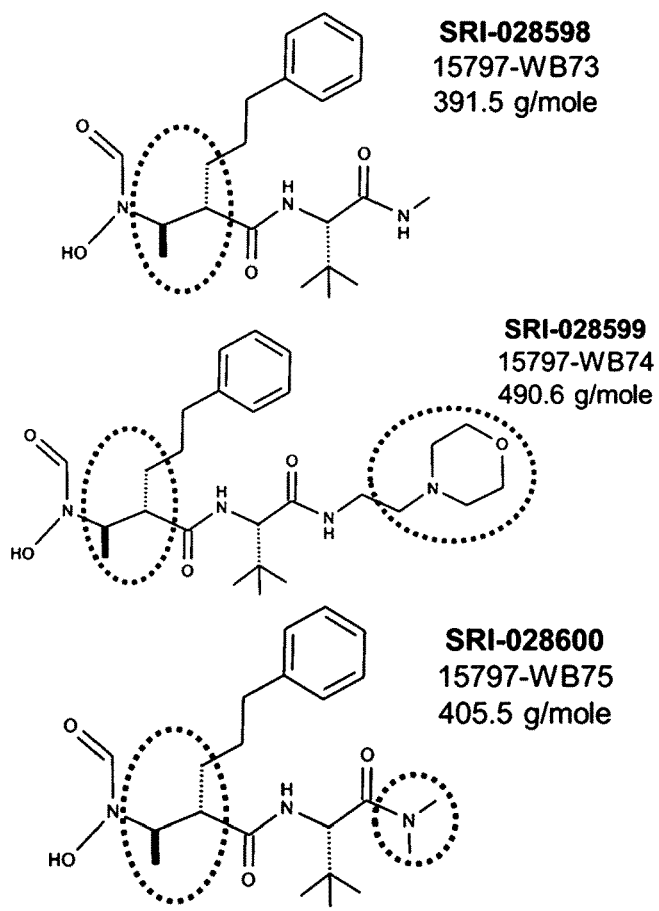
Figure 3A:
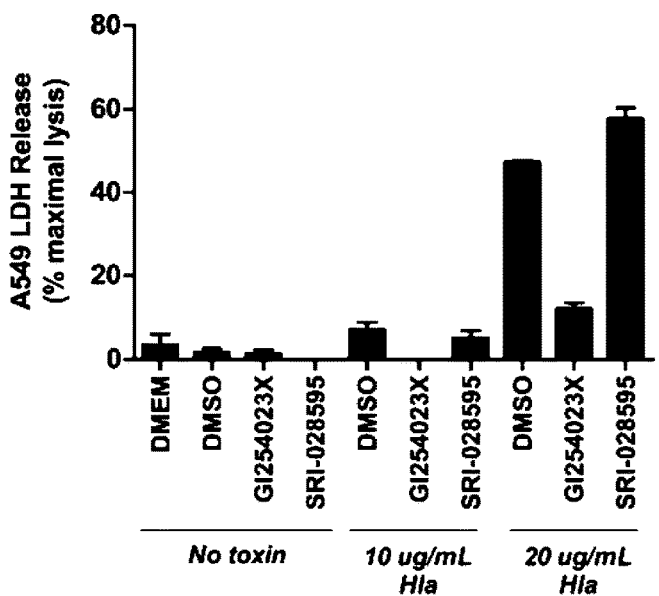
FIGS. 3A-D FIG. 3A is a graph depicting inhibition of Hla-induced (0, 10, and 20 µg/mL) eukaryotic cell death in response to GI254023X and an ADAM10 inhibitor with inverted R3 stereochemistry.
Figure 3B:
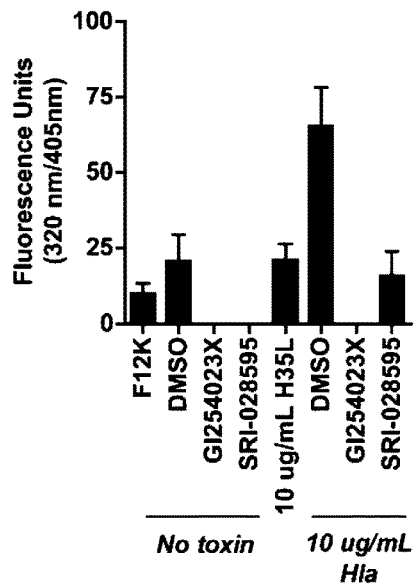
Figure 3C:
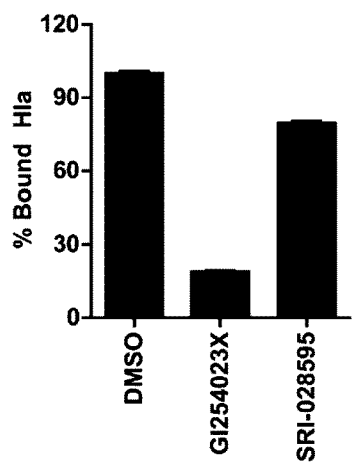
Figure 3D:
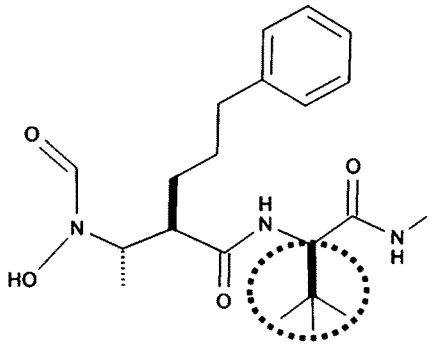
Figure 4A:
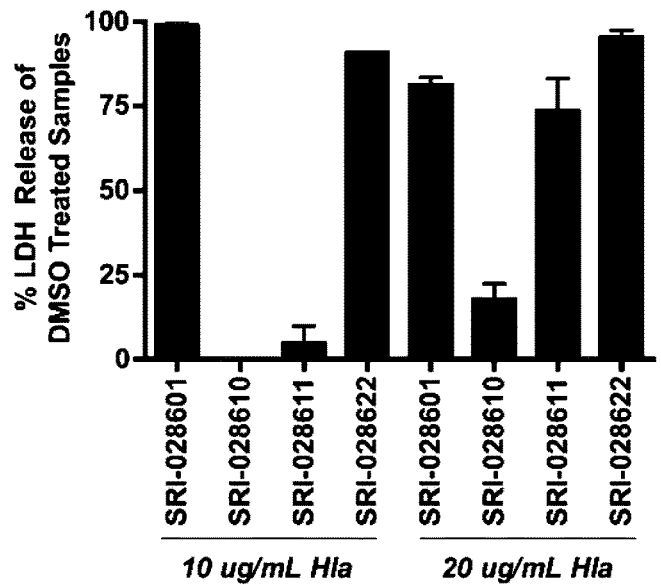
FIGS. 4A-D FIG. 4A is a graph depicting inhibition of Hla-induced (0, 10, and 20 µg/mL) eukaryotic cell death in response to four ADAM10 inhibitors with carbon chains of varying length at the R2 position.
Figure 4B:
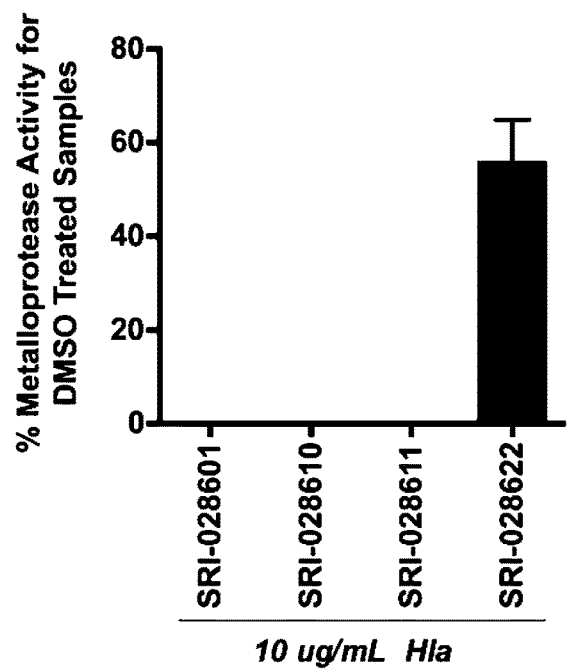
Figure 4C:
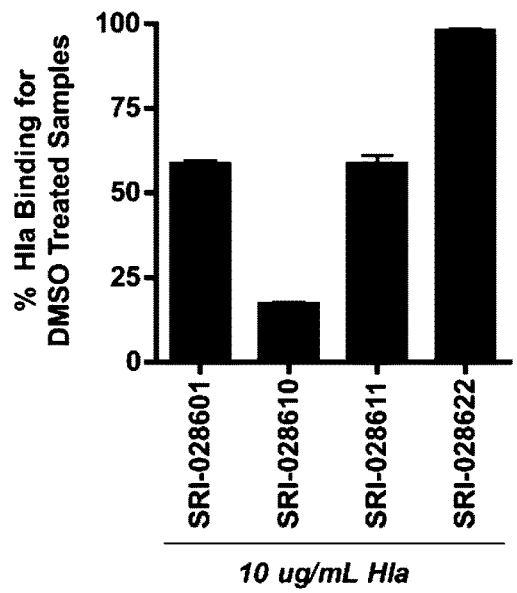
Figure 4D:
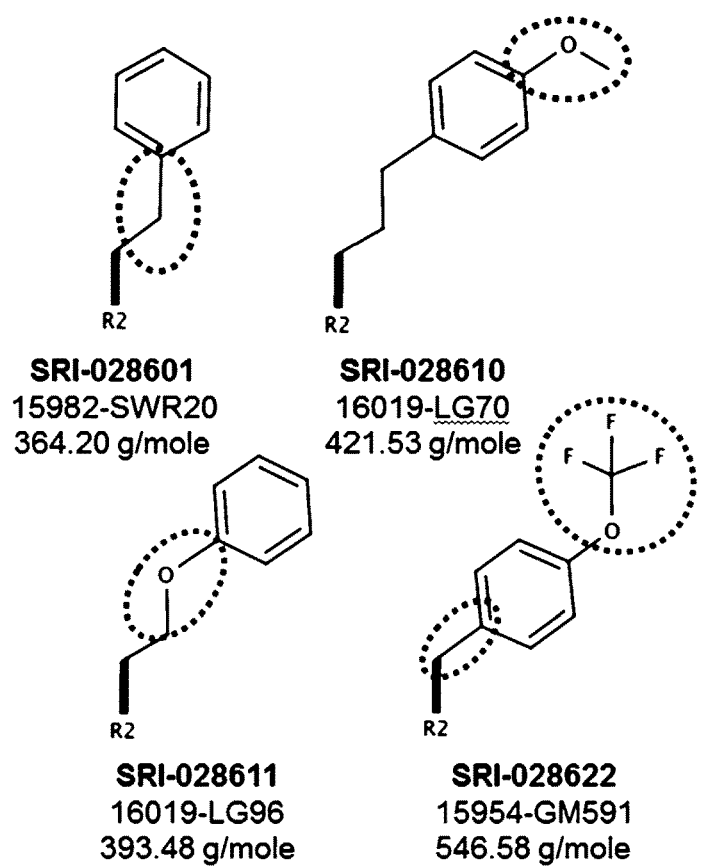
Figure 5A:
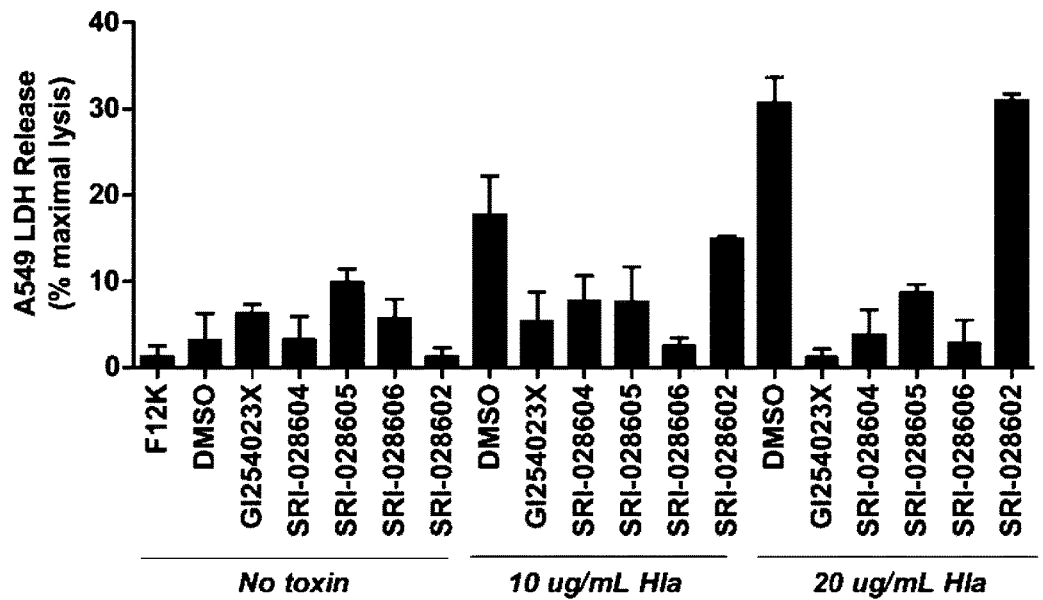
FIGS. 5A-D FIG. 5A is a graph depicting inhibition of Hla-induced (0, 10, and 20 µg/mL) eukaryotic cell death in response to four ADAM10 inhibitors.
Figure 5B:
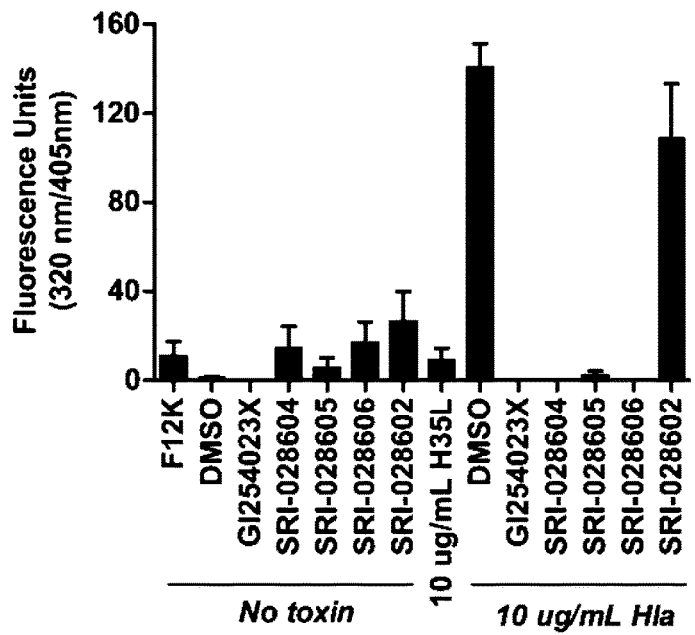
Figure 5C:
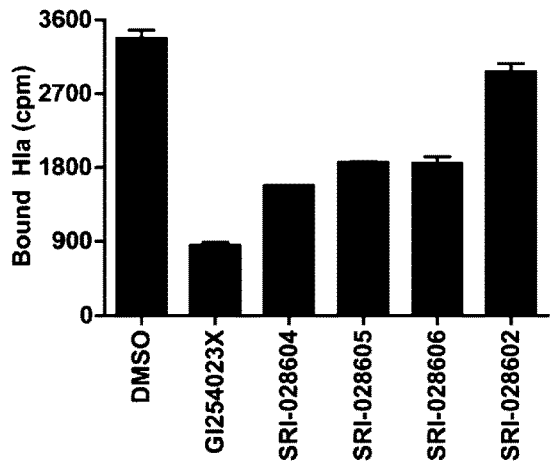
Figure 5D:
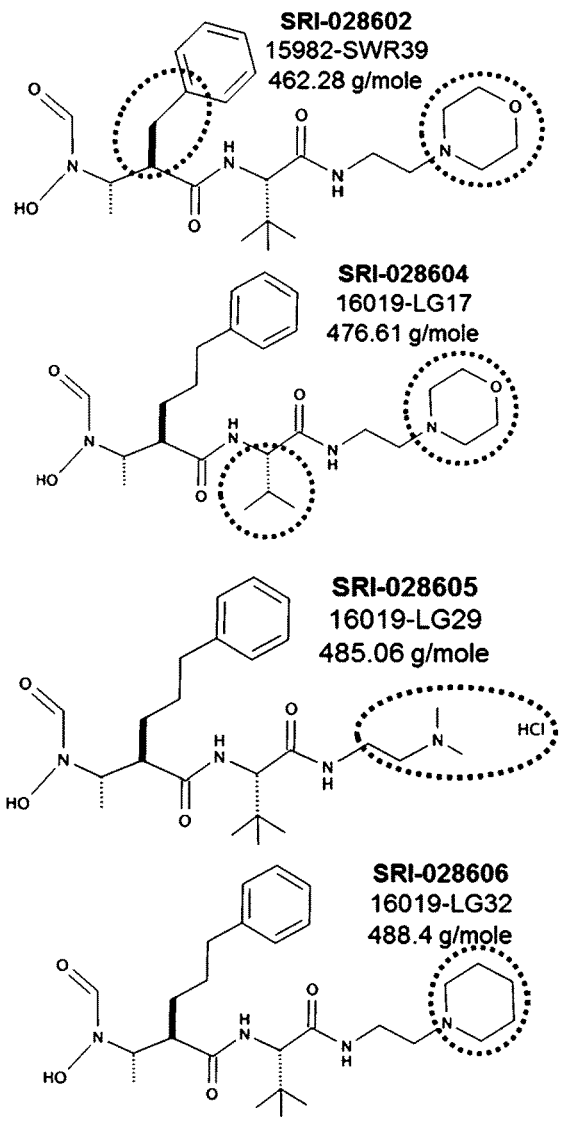
Figure 6A:
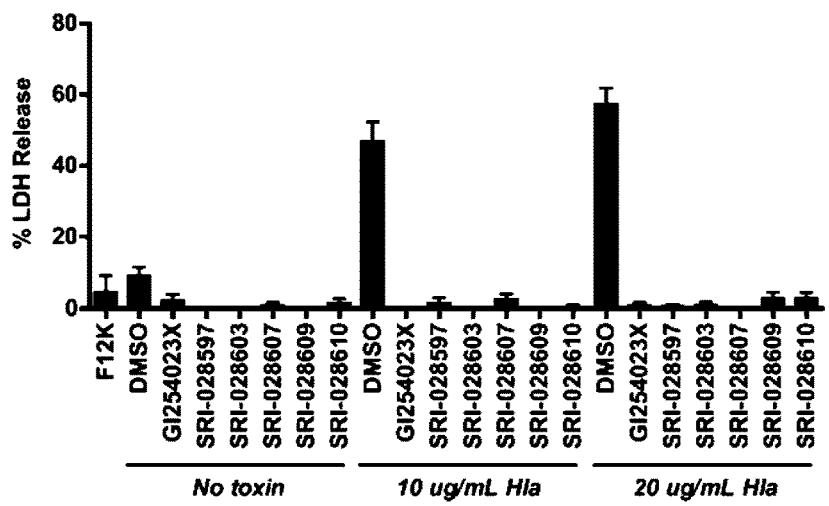
FIGS. 6A-E FIG. 6A is a graph depicting inhibition of Hla-induced (0, 10, and 20 µg/mL) eukaryotic cell death in response to five ADAM10 inhibitors.
Figure 6B:
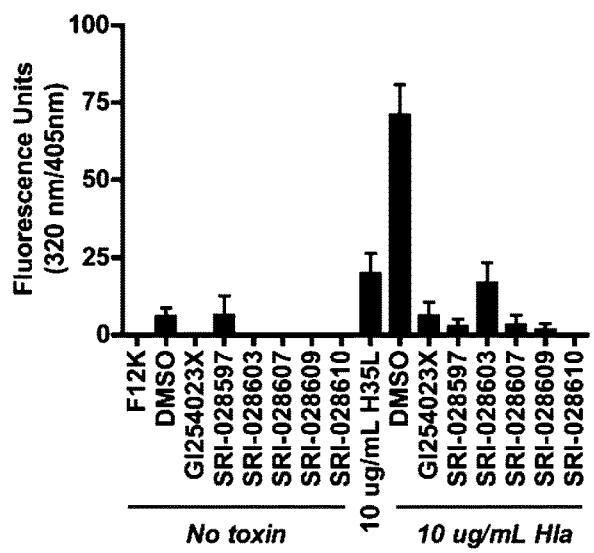
Figure 6C:
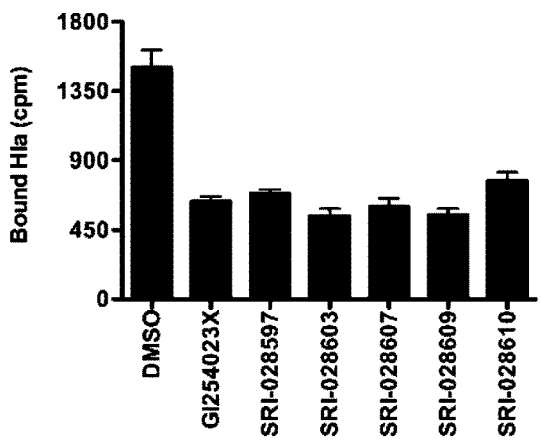
Figures 6D, 6E:
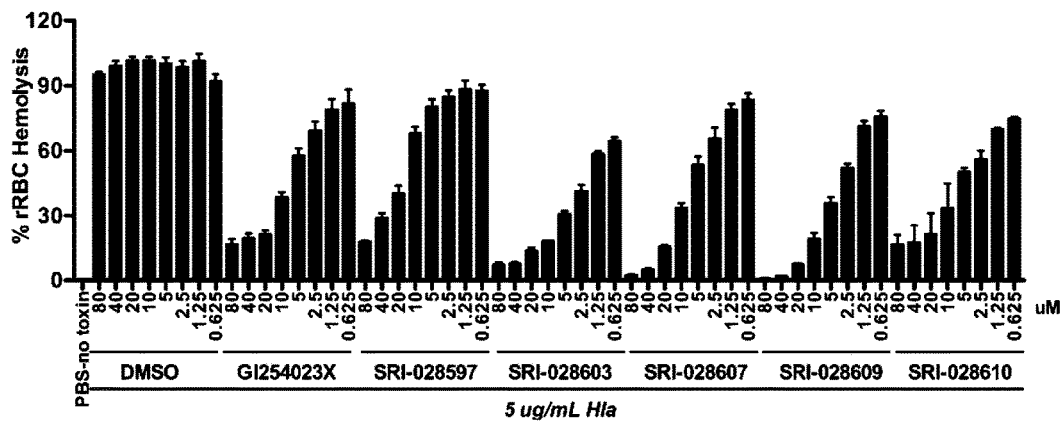
Figure 7A:
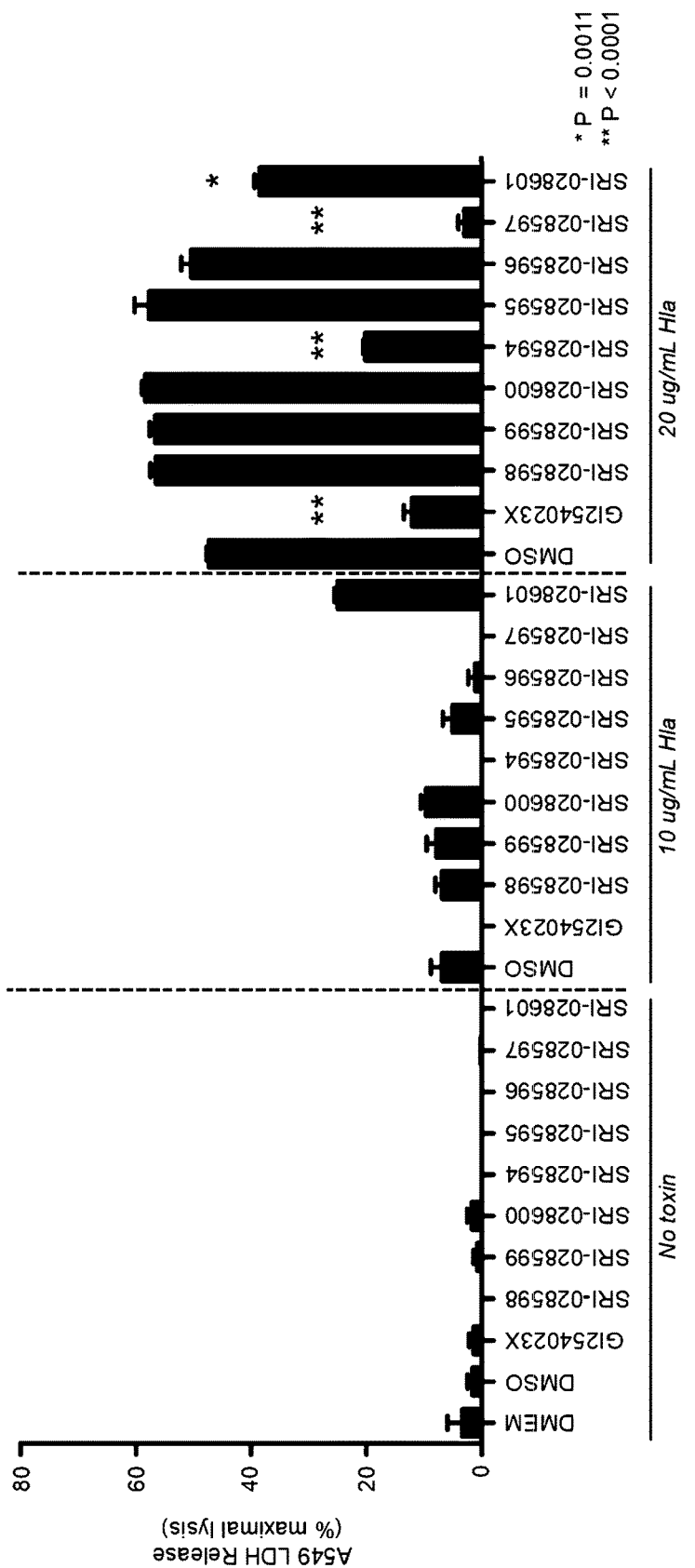
Figure 7D:
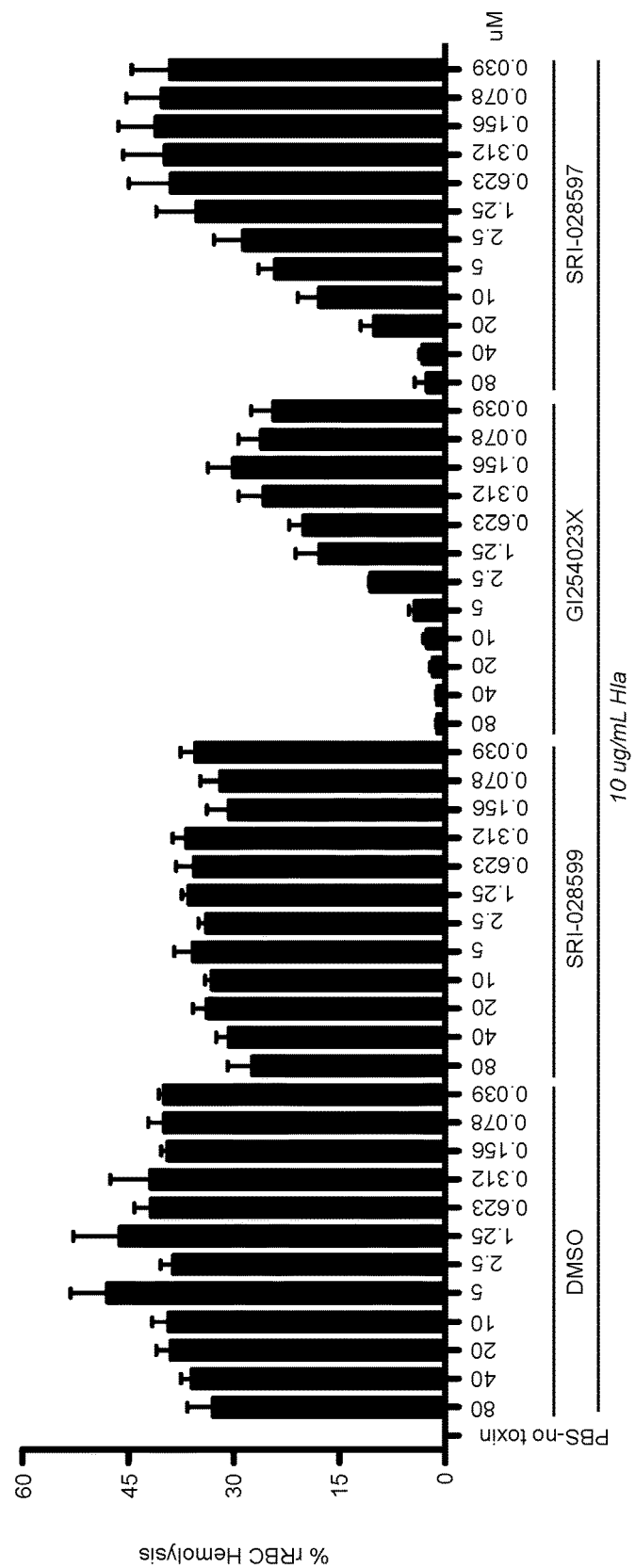
Figure 8A:
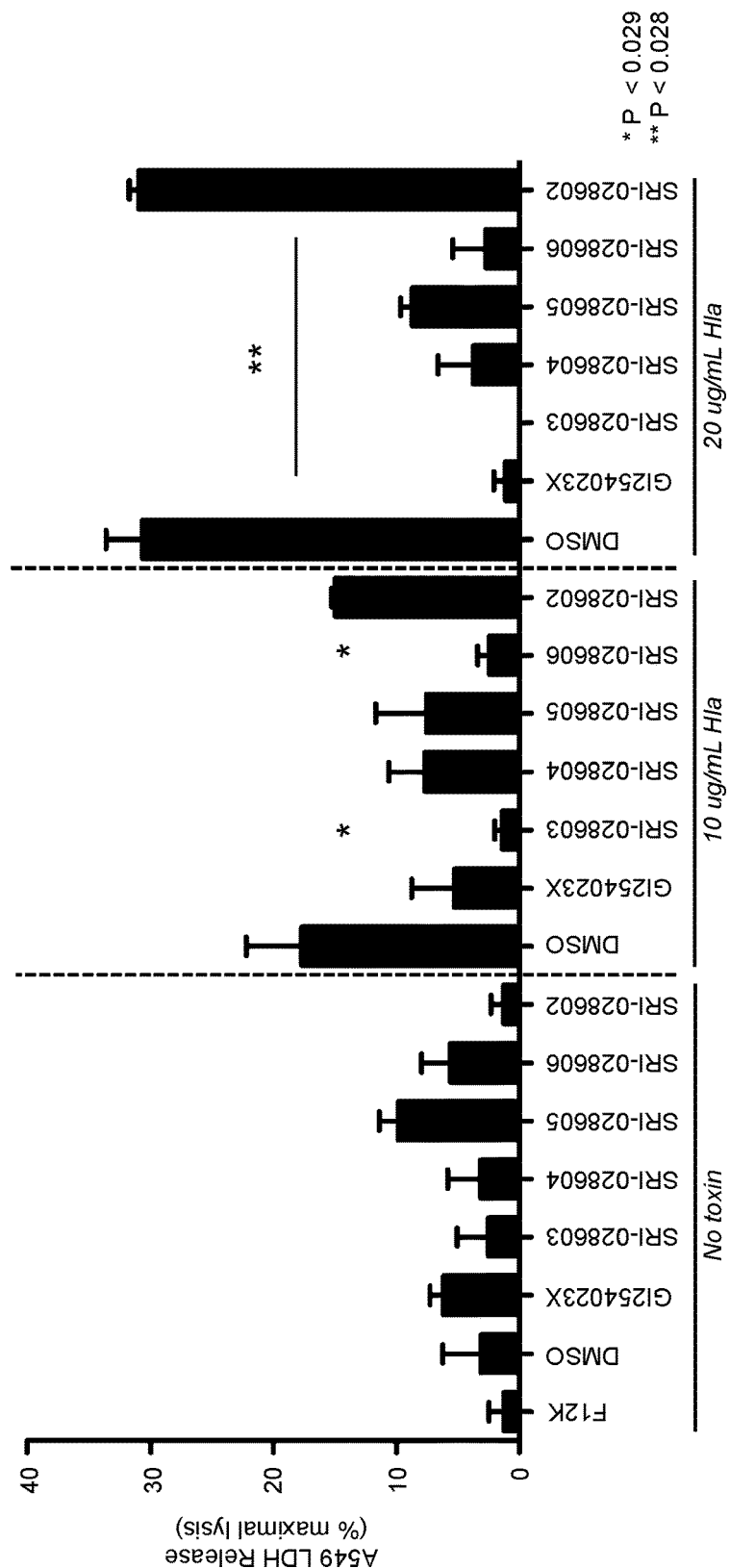
Figure 8D:
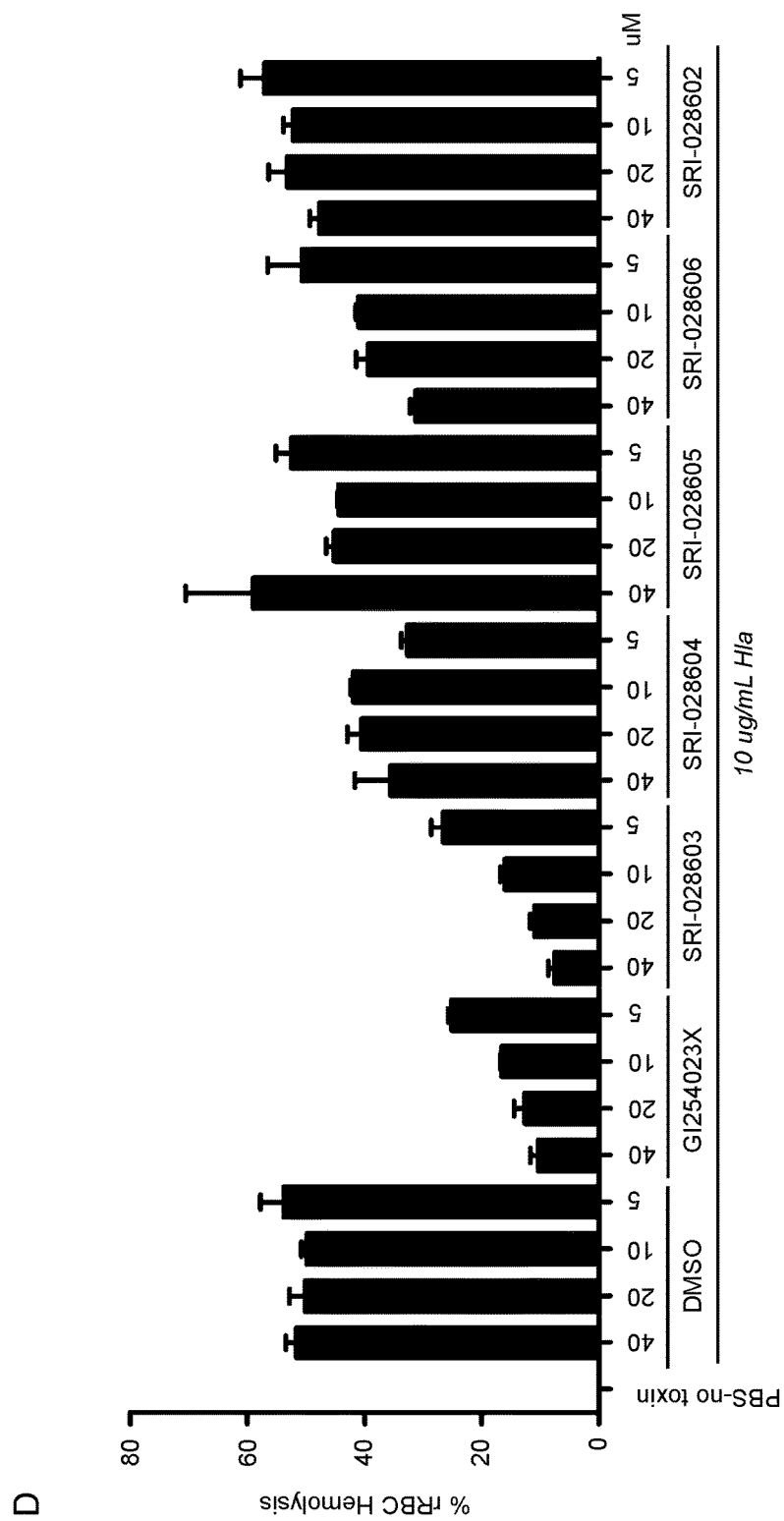
Figure 9A:
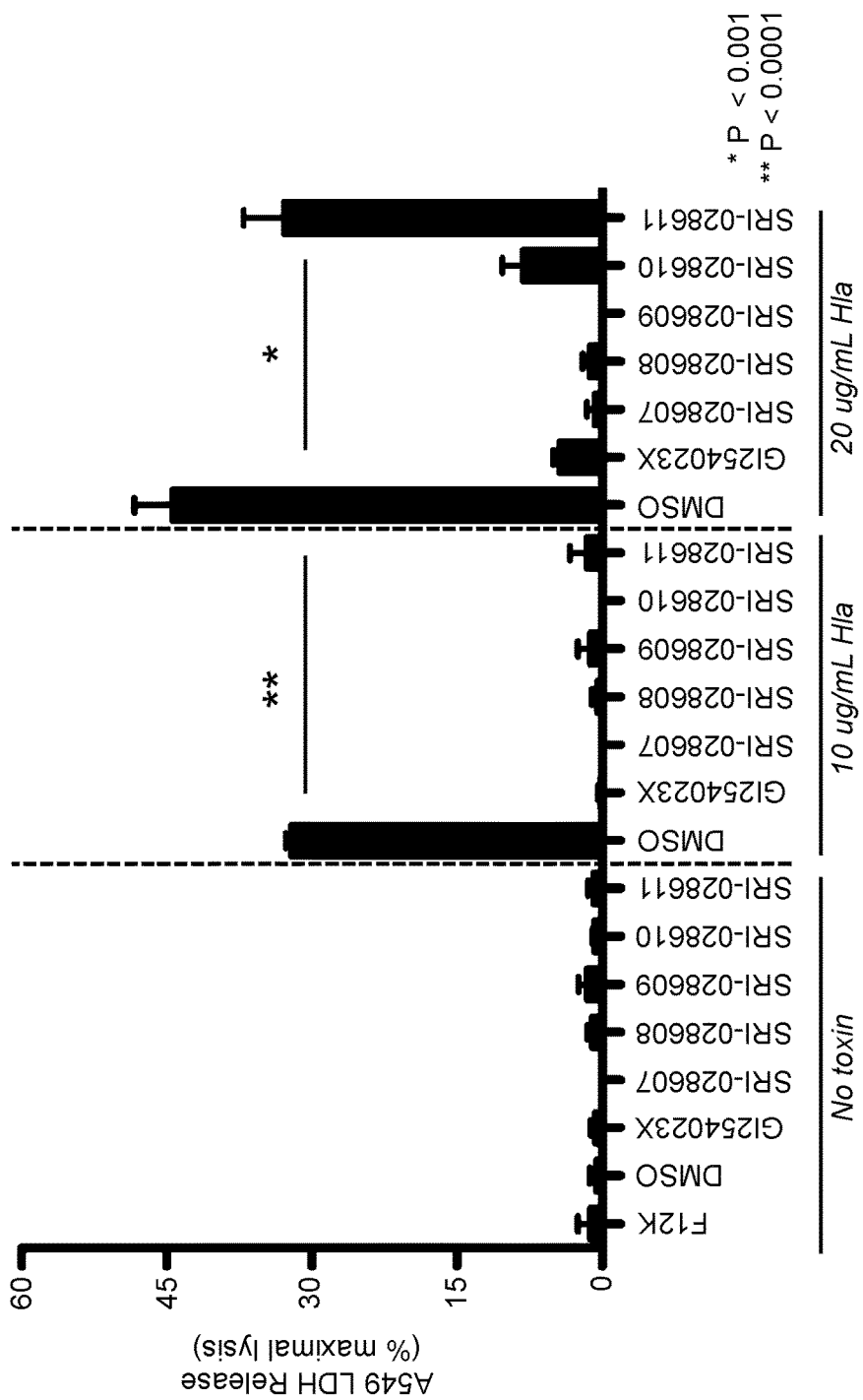
Figure 9D:
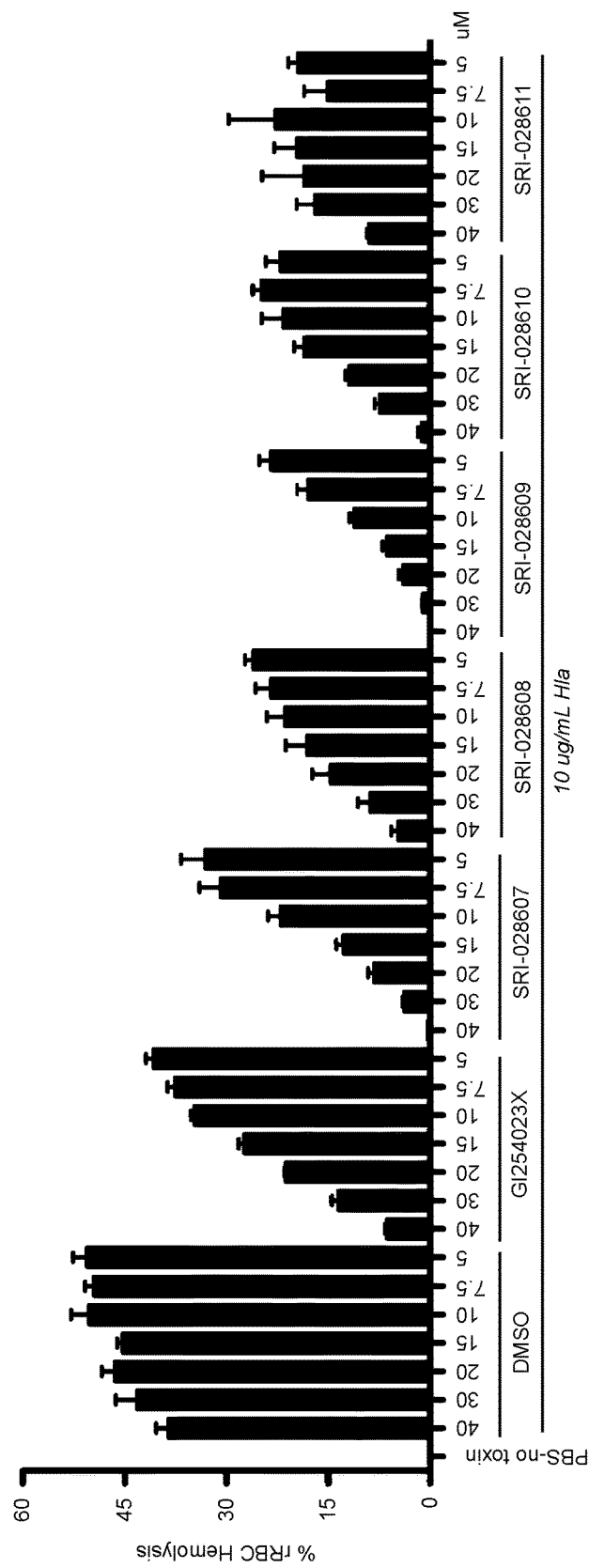
Figure 10A:
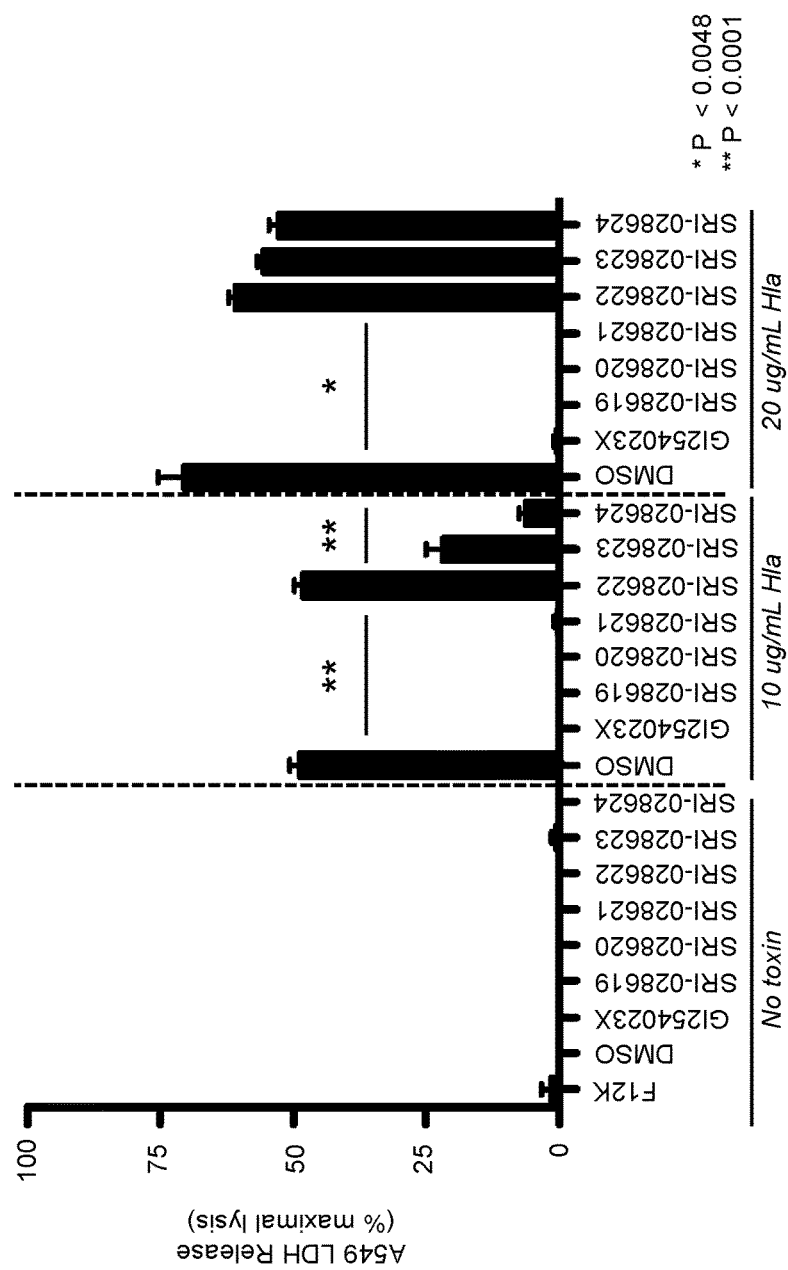
Figure 10D:
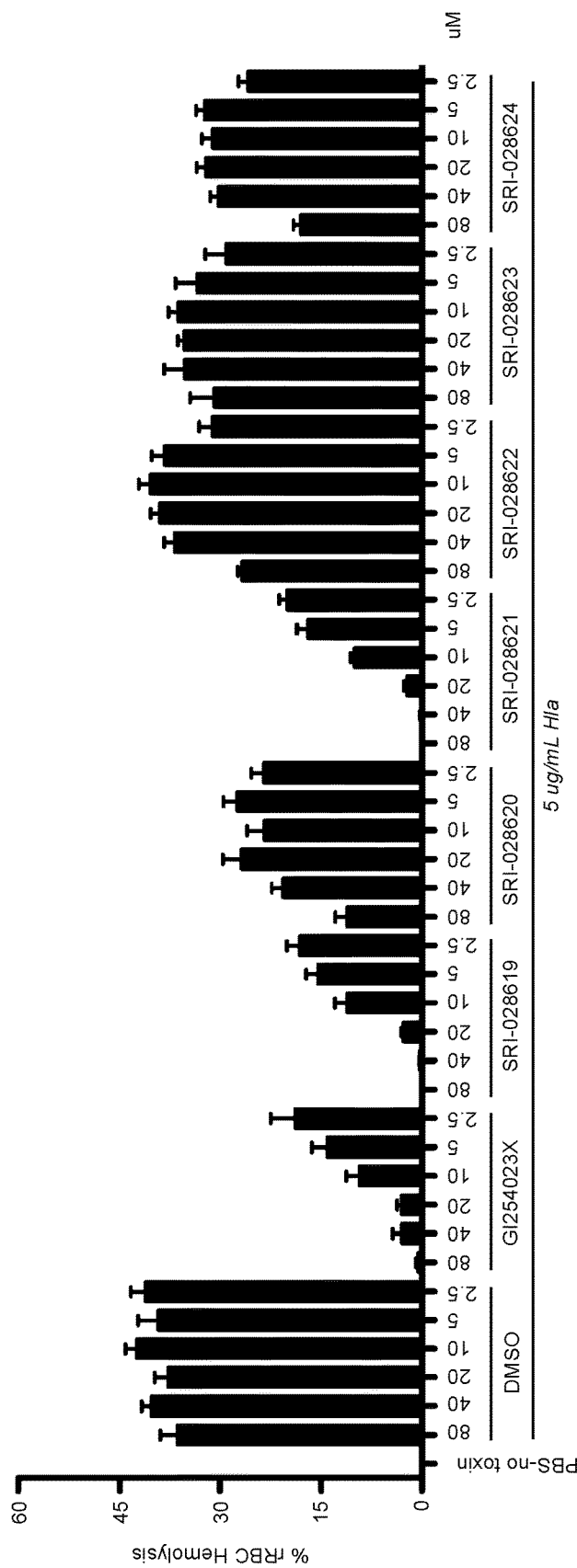
Figure 12:
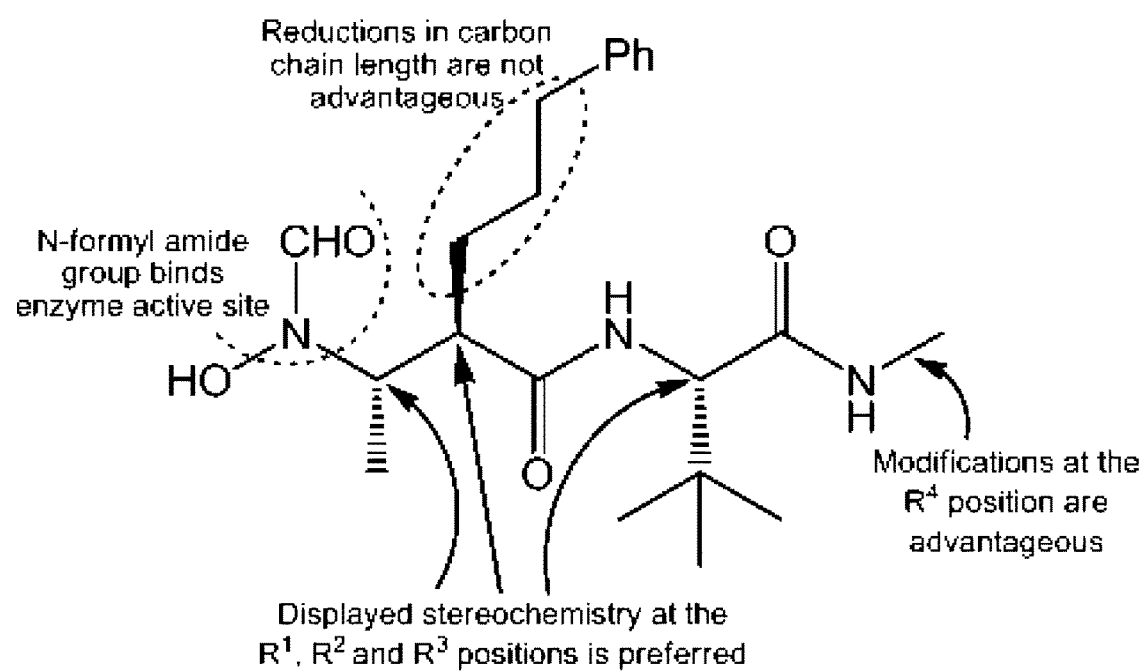
FIG. 12 is a summary of the structure-activity relationships gathered from the analyses of the presently claimed compounds.
Figure 14A:
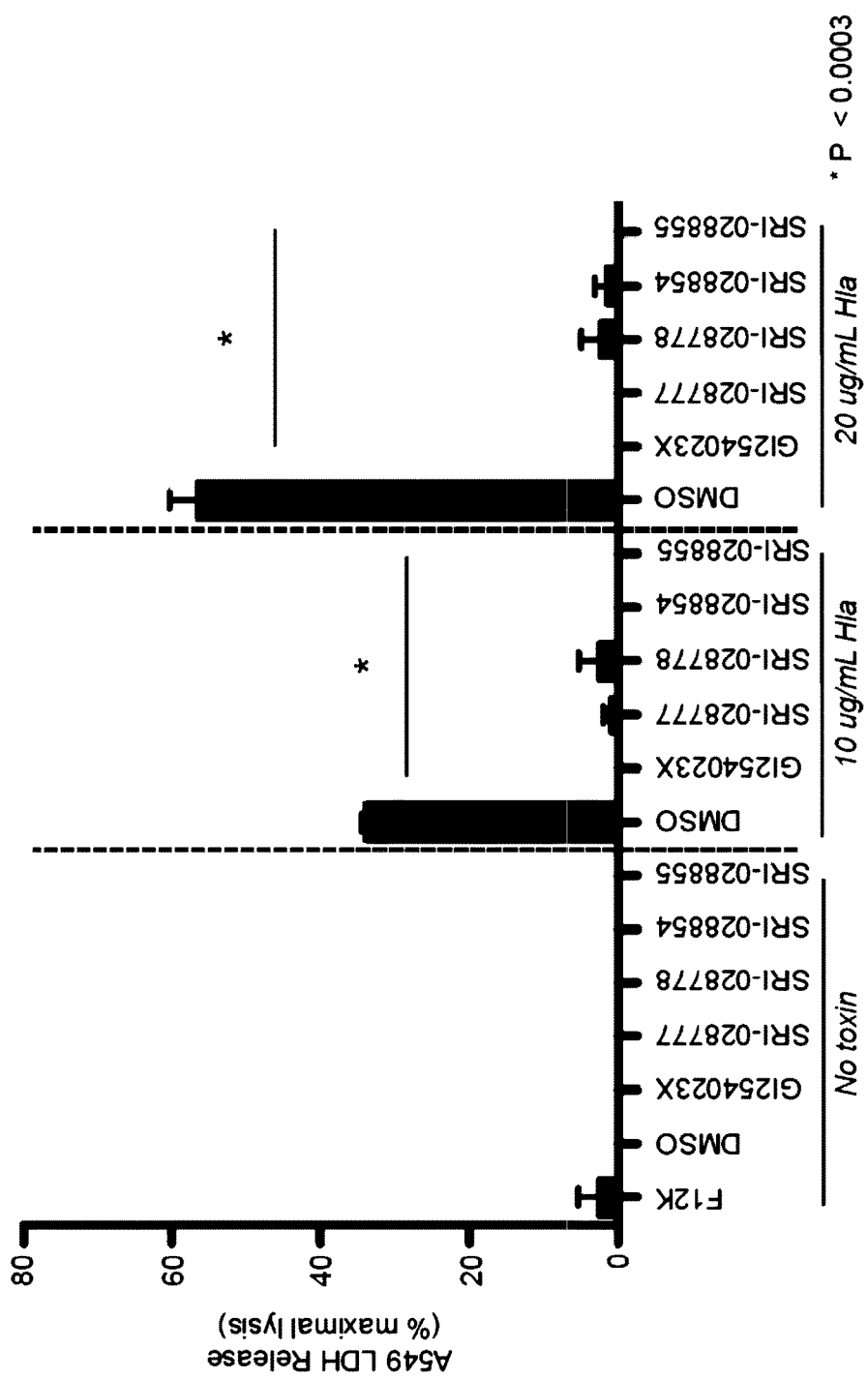
Figure 14D:
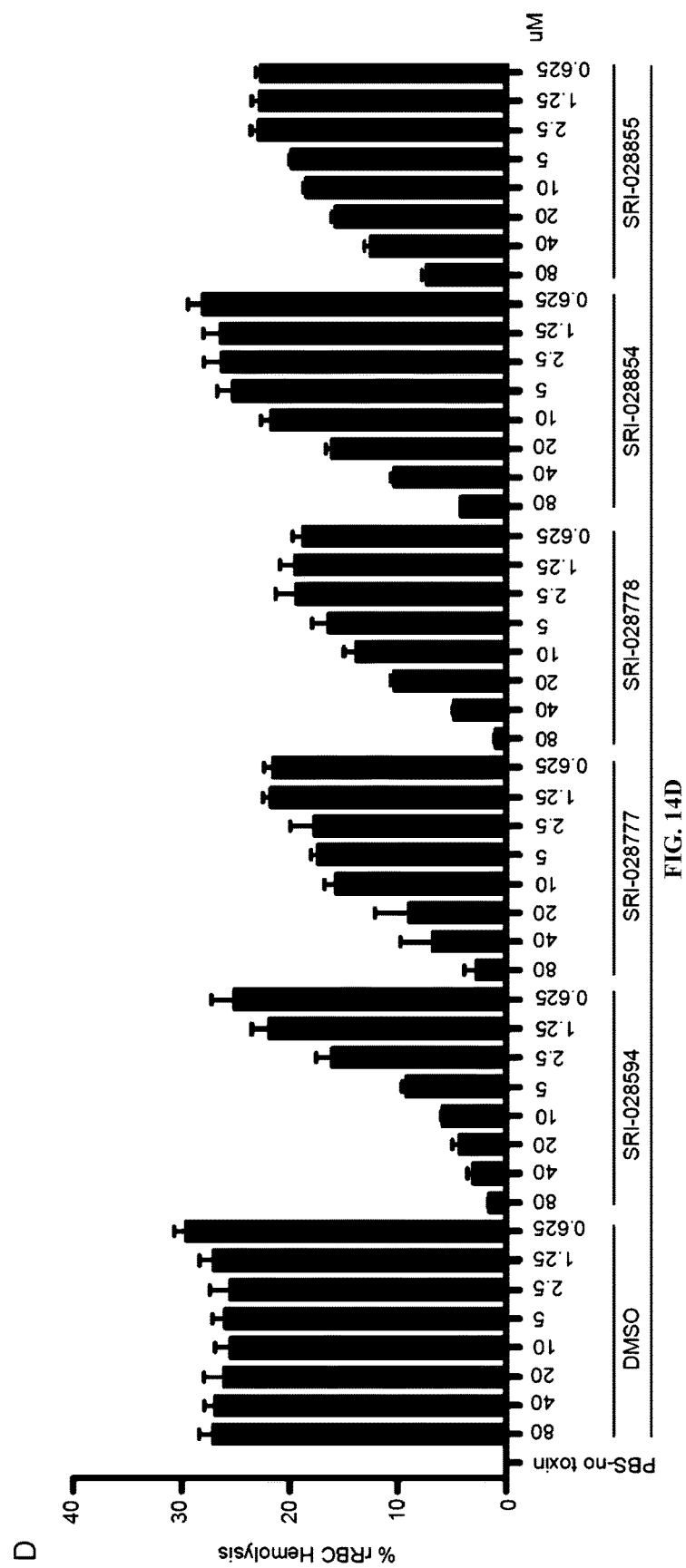
Figure 15A:
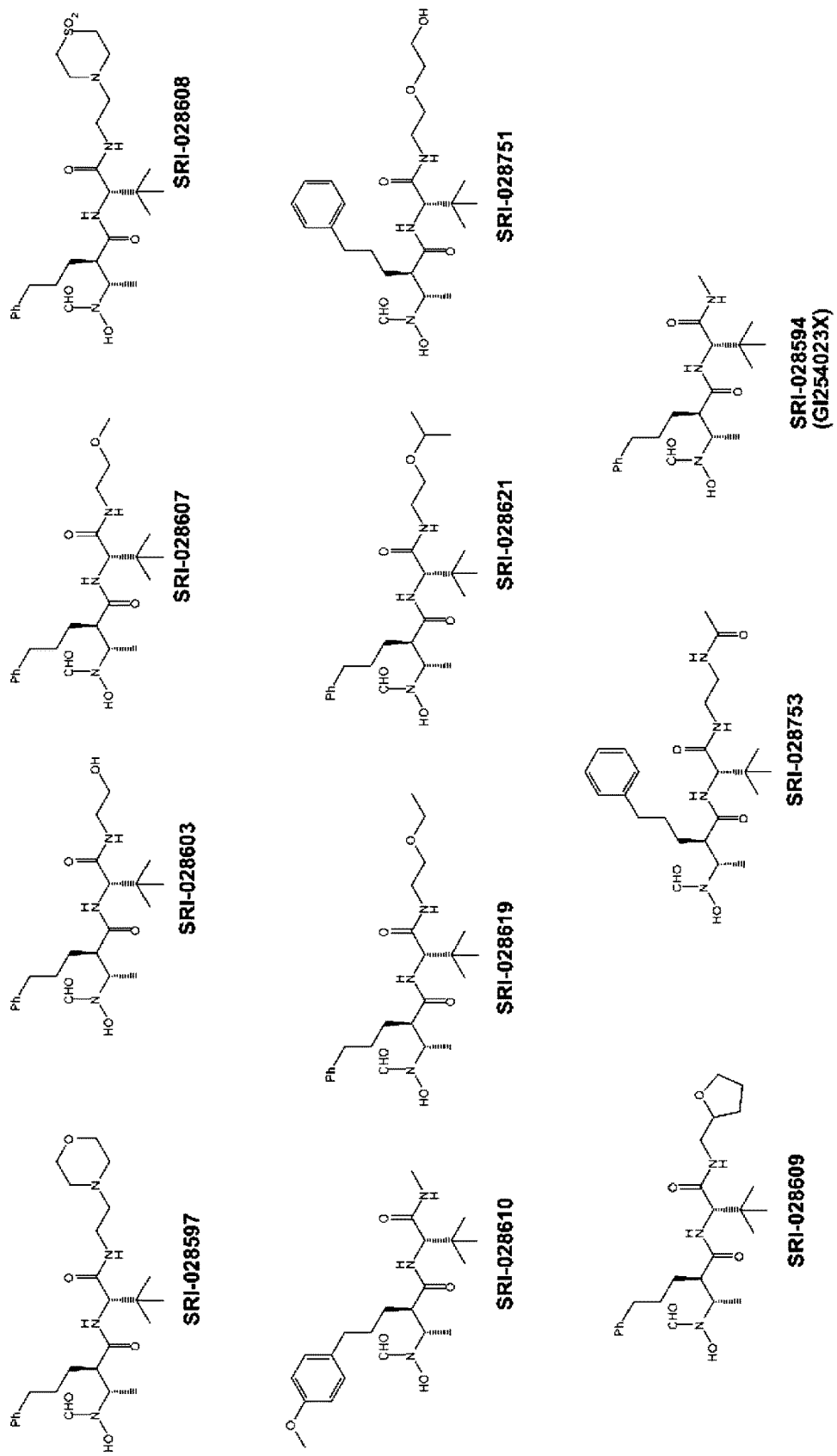
Figure 15B:
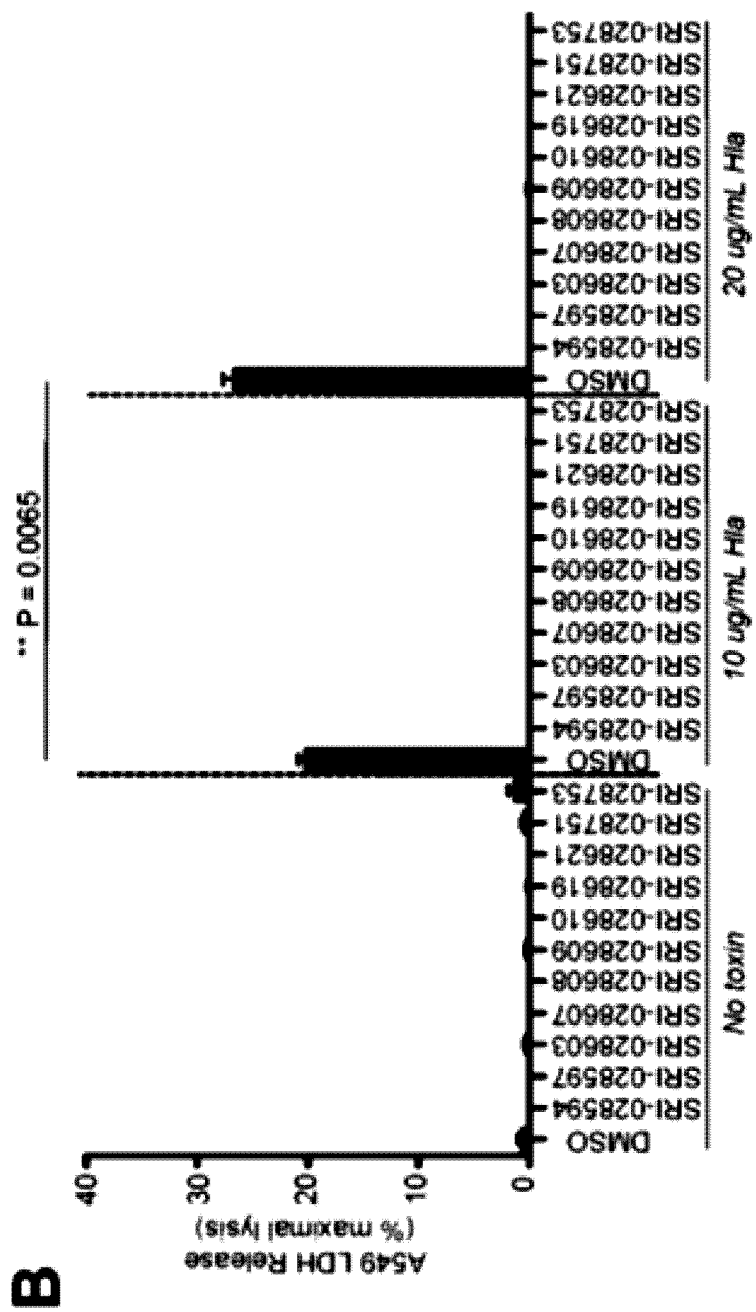
Figure 16A:
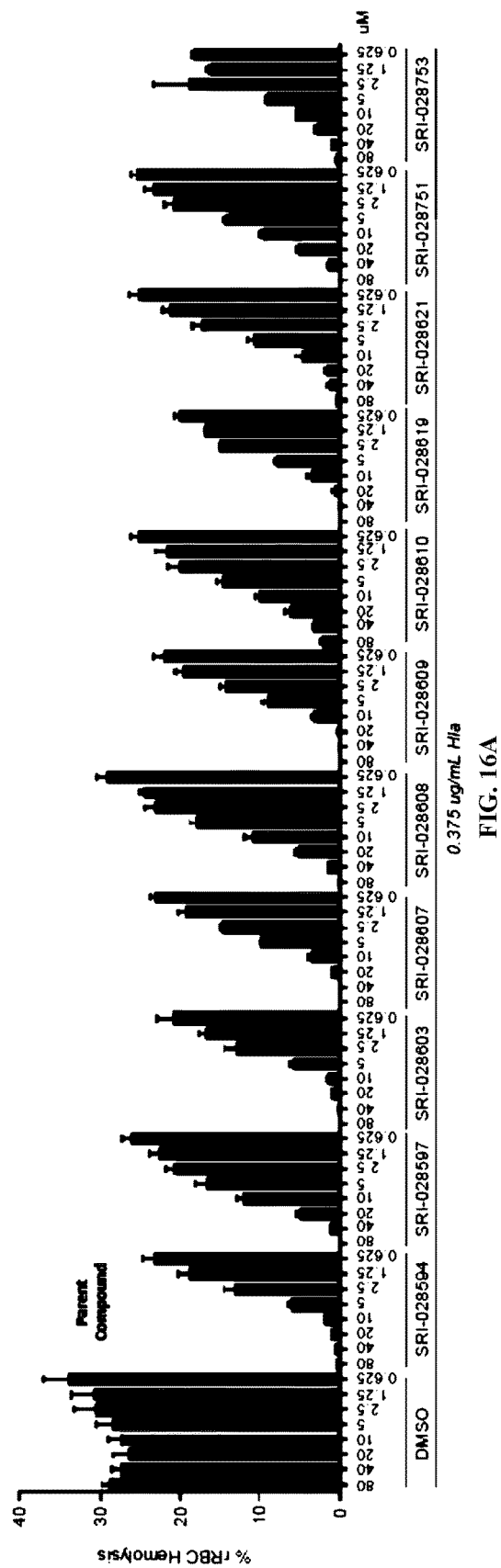
FIGS. 16A-B FIG. 16A is a table exhibiting hemolysis of rabbit erythrocytes by Hla in the presence of ADAM10 inhibitors. Titrations of each inhibitor were used to calculate IC50 values listed in the Tables. Data are presented as mean±SEM.
Figure 16B:
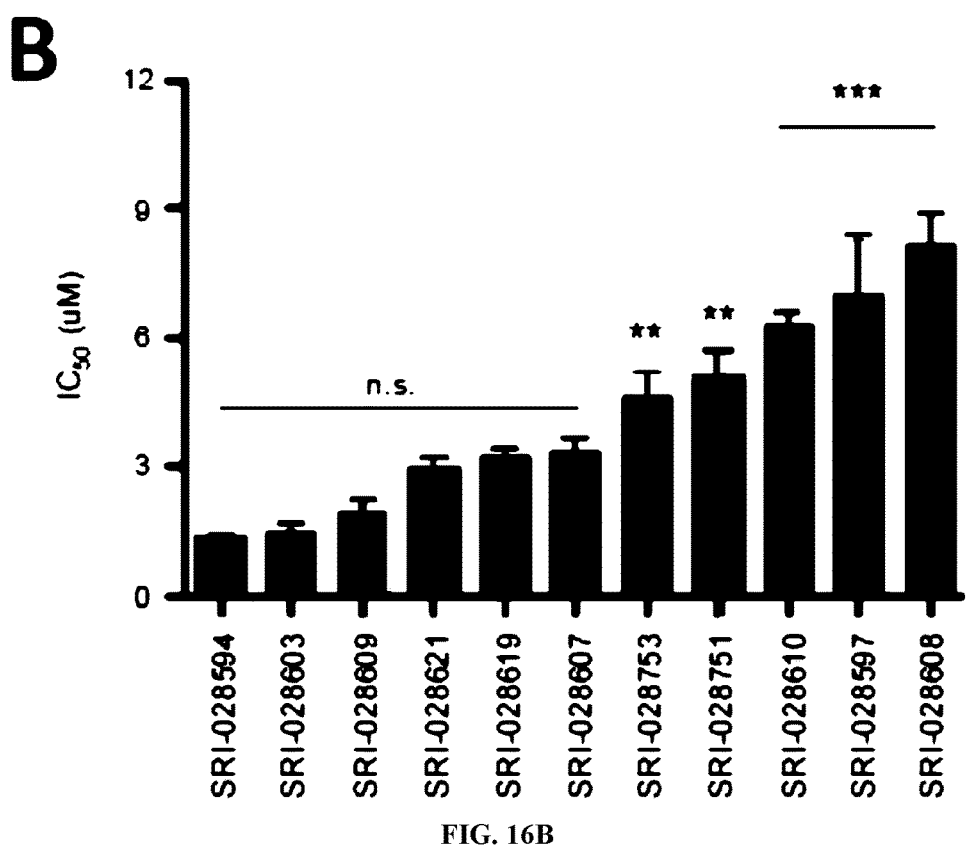
Figure 17A:
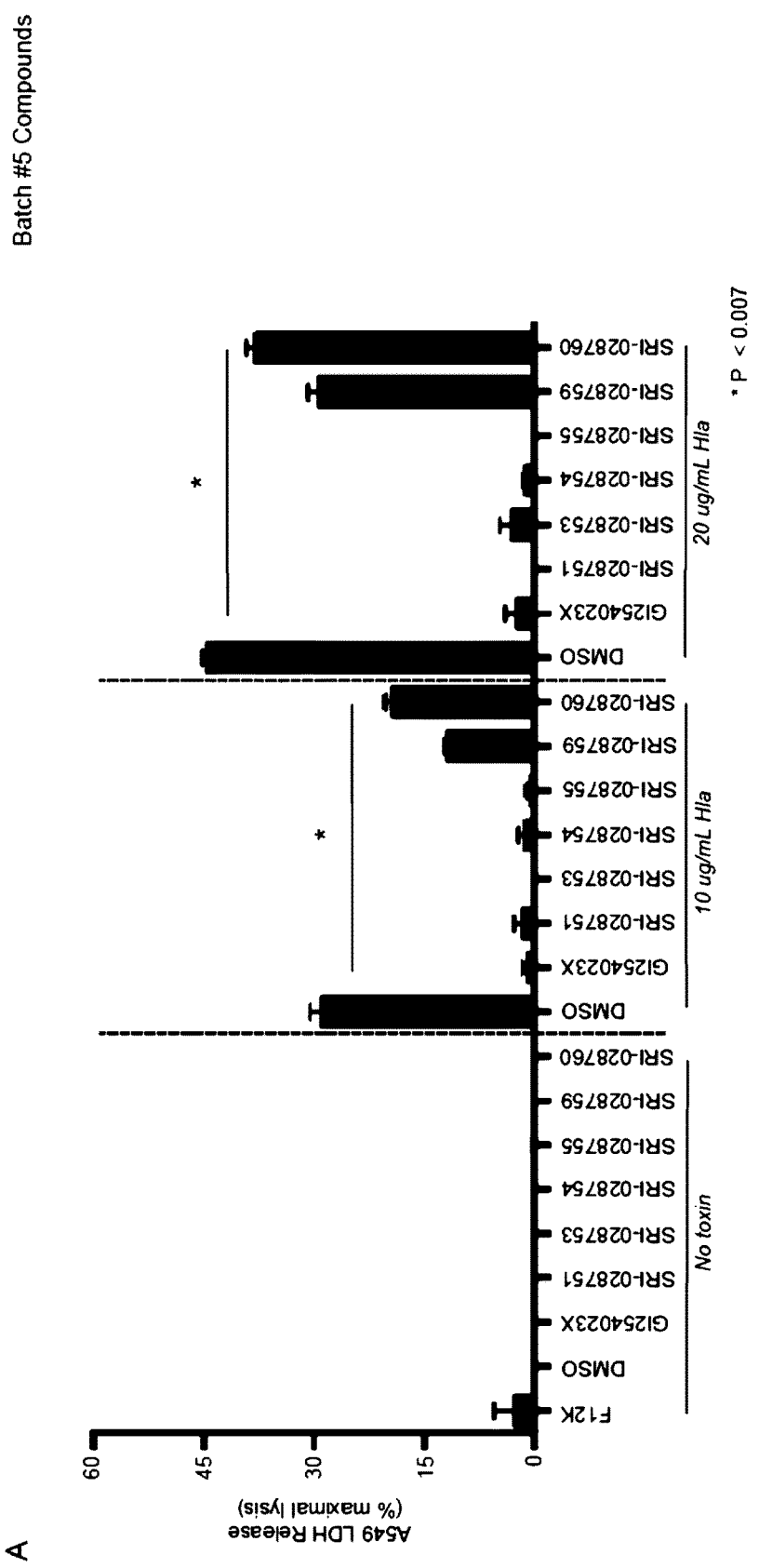
Figure 17D:
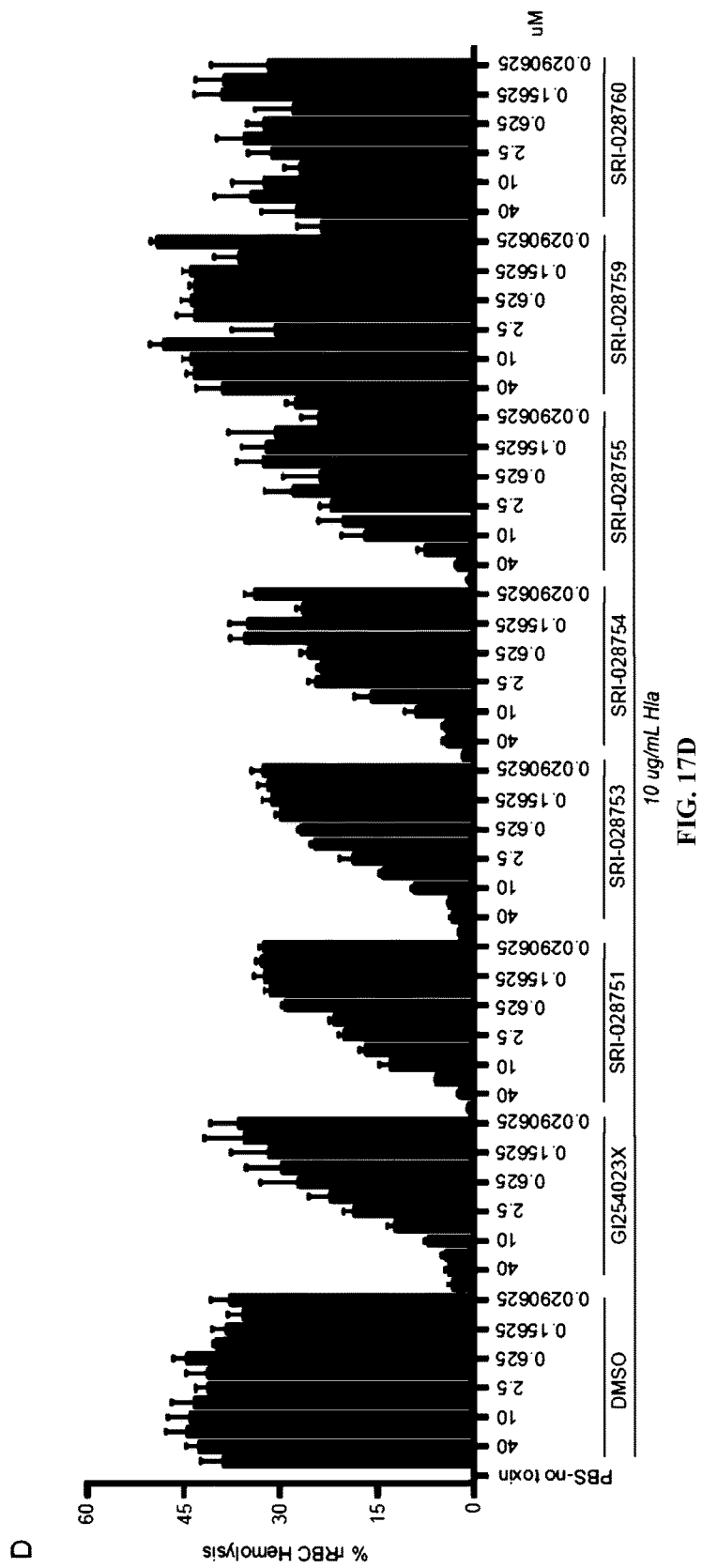

*Staphylococcus aureus* is a leading cause of hospital-acquired and community-associated infections in the U.S. and worldwide. This pathogen has developed multiple antibiotic resistance traits, jeopardizing our ability to treat these infections now and into the future. Host-targeted therapies represent a novel strategy by which to manage infections caused by drug-resistant bacterial strains. *S. aureus* secretes an arsenal of proteins and toxins that aid in disease pathogenesis. Included in this arsenal is α-toxin (Hla), a heptameric pore-forming toxin that binds to the surface of eukaryotic cells and generates a membrane-perforating pore approximately 1-2 nm wide.

A Disintegrin and Metalloprotease 10 (ADAM10) was recently discovered to be the cellular receptor for Hla. Formation of the toxic pore upon ADAM10 binding leads to the rapid upregulation of receptor metalloprotease activity; this in turn causes the pathophysiologic cleavage of native ADAM10 substrates including cadherin proteins (Inoshima, 2011; Inoshima 2013; Powers 2013). Previous data from indicated that inhibition of ADAM10 metalloprotease activity by the small molecule inhibitor GI254023X prevents Hla-mediated cytotoxicity. In murine model systems that recapitulate infection of the lung, skin, or sepsis, GI254023X blunted *S. aureus* disease. GI254023X has an $IC_{50}$ of ~5 μM and is poorly soluble in aqueous solution, rendering it less desirable for a product development program. See also U.S. Provisional Application No. 61/411,765, which is incorporated herein by reference in its entirety.

Novel ADAM10 inhibitors were designed and synthesized based on the structure of GI254023X. These inhibitors were tested in a variety of assays including those that measure Hla binding, toxin-induced cell death, induction of ADAM10 metalloprotease activity and the downstream consequences of Hla-ADAM10 complex formation. These structure-activity relationship studies have identified favorable chemical modifications that are anticipated to improve the activity of the inhibitor as a therapeutic agent.

Epithelial and endothelial barriers are a potent host defense against invasive bacterial infection. Pathogens circumvent this barrier through virulence factors that target specific structural elements of the epithelium, impairing its integrity (Kim et al., 2010). Critical bacterial targets within the epithelium include focal adhesion complexes, apical tight junction proteins, and the cadherin:catenin protein complex that comprises the adherens junction. *Staphylococcus aureus* is a leading cause of bacteremia, pneumonia, skin and soft tissue infection and lethal toxin-mediated syndromes (Lowy et al., 1998). This organism exhibits a dual interaction with its human host, existing as a harmless skin commensal and deadly invasive pathogen armed with multiple virulence factors. *S. aureus* alpha-hemolysin (Hla) is a pore-forming cytotoxin that contributes to the pathogenesis of pneumonia, skin infection, and corneal infection (O'Callaghan et al., 1997; Kennedy et al., 2010; Bubeck Wardenburg et al., 2007a, 2007b). Further, Hla potentiates the penetration of *S. aureus* toxic shock syndrome toxin across the vaginal epithelium (Brosnahan et al., 2009). Pore-forming cytotoxins (PFTs) are a large family of secreted bacterial virulence factors characterized by their ability to assemble into multimeric, membrane-perforating complexes that cause eukaryotic cell injury and death (Gonzalez et al., 2008, which is hereby incorporated by reference). Other than bacteria, many organisms, such as cnidarians, mushrooms, plants, sea anemones and earthworms, also produce PFTs (Gonzalez et al., 2008, Iacovache et al., 2008). PFTs are secreted by the pathogens in a water-soluble form. Once secreted, PFTs diffuse towards their target cell and bind to the target cell via a specific receptor, usually with high affinity. After binding, PFTs often multimerizes into an amphipathic structure that finally inserts in the target cell membrane and forms a pore (Gonzalez et al., 2008).

There are two major types of PFTs, α-PFTs and β-PFTs. α-PFTs insert into the lipid bilayer of the target cell as α-helices. α-PFTs family includes, but not limited to, pore-forming colilcins secreted by *Escherichia coli*, the translocation domain of Diphtheria toxin, mammalian anti-apoptotic protein Bcl2, Cry toxins from *Bacillus thuringiensis*. β-PFTs contain a high percentage of β-structure, and cross the membrane as β-barrels. β-PFTs family includes, for example, aerolysin from *Aeromonas hydrophila*, α-toxin from *Staphylococcus aureus*, cholesterol-dependant cytolysins (CDCs) (Gonzalez et al., 2008).

Among these PFTs, aerolysin is a representative toxin that forms small pores. Aerolysin is secreted by various species of the genus *Aeromonas*. A homologue of aerolysin, α-toxin, is produced by *Clostridium septicum*. Both aerolysin and α-toxin homologue are secreted as inactive protoxins, which are activated by proteolytic cleavage and bind to GPI anchored membrane proteins at the target cell surface. α-toxin from *S. aureus* is another small pore forming PFT (Gonzalez et al., 2008). CDCs are a large family of pore-forming toxins that are produced by more than 20 members from 24 different Gram-positive bactgerial species, such as *Clostridium, Streptococcus, Listeria, Bacillus*, and *Arcanobacterium* (Gonzalez et al., 2008, Tweten, 2005). For example, CDC family members include Streptolysin O (SLO) from *Streptococcus pyogenes*, Listeriolysin O (LLO) from *Listeria monocytogenes*, Pneumolysin O (PLY) from *Streptococcus pneumoniae*, and Perferingolysin O (PFO) from *Clostridium perfringens* (Gonzalez et al., 2008). CDCs are characterized by absolute dependence on the presence of membrane cholesterol and the formation of large pores (Tweten, 2005).

*Staphylococcus aureus* encodes multiple PFTs, the most prominent and well-studied of which is α-hemolysin (Hla) (Tomita and Kamio, 1997). Hla is essential for the pathogenesis of diseases involving epithelial cell-lined interfaces, including pneumonia, dermonecrotic skin infection, corneal infection, and toxic shock syndrome (O'Callaghan et al., 1997; Kennedy et al., 2010; Bubeck Wardenburg et al., 2007a; Bubeck Wardenburg et al., 2007b; Brosnahan et al., 2009). Cellular injury induced by Hla has been attributed to its ability to form a heptameric structure, creating a central 1-2 nm pore structure that penetrates the eukaryotic lipid bilayer (Song et al., 1996). Mutant forms of the toxin that fail to form a stable oligomeric pore are non-toxigenic (Walker and Bayley, 1995; Jursch et al., 1994; Menzies and Kernodle, 1994). Treatment of cells or animals with β-cyclodextrin compounds that structurally interfere with pore function also abrogate toxicity (Karginov et al., 2007; Ragle, 2010). The identification of ADAM10 as a cellular receptor for Hla provides an opportunity to elucidate the role of the receptor in disease and define the mechanisms by which the toxin causes cell injury.

Hla utilizes A Disintegrin and Metalloprotease 10 (ADAM10) as a cellular receptor (Wilke and Bubeck Wardenburg, 2010). Zinc-dependent catalysis by ADAM10 mediates proteolytic cleavage of a number of ectodomain-containing proteins including E-cadherin (Reiss and Saftig, 2009; Maretzky et al., 2005). The homotypic interaction of E-cadherin molecules between neighboring cells provides tensile strength to the epithelium at the adherens junction (Shapiro and Weis, 2009). Surprisingly, Hla induces or stimulates the enzymatic activity of ADAM10 that leads to the direct proteolytic cleavage of the extracellular domain of E-cadherin, releasing the N-terminal ectodomain and thereby destroying the E-cadherin-dependent linkage between adjacent cells. Thus, ADAM10 is more than just a receptor for Hla, it also contributes to Hla related pathology. The profile of Hla-dependent *S. aureus* diseases strongly suggests that this toxin is a principal mediator of staphylococcal injury to the epithelium. It is contemplated that Hla upregulates ADAM10 metalloprotease activity upon binding, leading to enhanced E-cadherin cleavage.

A. THERAPEUTIC COMPOUNDS

An ADAM10 inhibitor is a compound that acts in conjunction with ADAM10 protein to inhibit, attenuate or decrease the activity of the ADAM10 protein. In certain embodiments the ADAM10 inhibitor is a small molecular weight compound. In specific embodiments, the ADAM10 inhibitor is a compound of the formula:

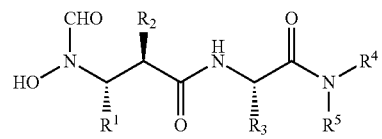

wherein $R^1$ may be hydrogen, alkyl, halogen, haloalkyl, alkenyl, or alkynyl, $R^2$ may be hydrogen, alkyl, benzyl, aryl, aralkyl, functionalized aralkyl, alkenyl, or alkynyl, $R^3$ may be hydrogen, alkyl, benzyl, aryl, alkenyl, or alkynyl, and $R^4$ may be hydrogen, alkyl, substituted alkyl, cycloalkyl, substituted cycloalkyl, 2-ethoxyethyl, 2-isopropoxyethyl, 1-methoxybutan-2-yl, (tetrahydrofuran-2-yl)methyl, 2-(piperidin-1-yl)ethyl, 2-(N-sulfonylmorpholine)ethyl, 2-(N,N-dimethyl)ethyl, 2-hydroxyethyl, 2-(N-morphonline)ethyl, or a heterocycle, and $R^5$ may be hydrogen or methyl. An ADAM10 inhibitor may be, in certain embodiments, a salt, enantiomer, or diastereomer of a molecule of the formula above.

In one embodiment, the ADAM10 inhibitor is a compound of the formula:

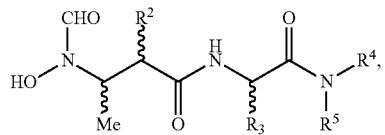

wherein $R^2$, $R^3$, $R^4$ and $R^5$ are as defined above. In some embodiments $R^2$ is benzyl, aralkyl, or a functionalized aralkyl; $R^3$ is alkyl, such as isopropyl or t-butyl; $R^4$ is hydrogen, alkyl, substituted alkyl, cycloalkyl, substituted cycloalkyl, 2-ethoxyethyl, 2-isopropoxyethyl, 1-methoxybutan-2-yl, (tetrahydrofuran-2-yl)methyl, 2-(piperidin-1-yl)ethyl, 2-(N-sulfonylmorpholine)ethyl, 2-(N,N-dimethyl)ethyl, 2-hydroxyethyl, 2-(N-morphonline)ethyl, or a heterocycle; and $R^5$ is hydrogen or methyl; or a salt, prodrug, enantiomer, or diastereomer thereof.

In some embodiments, the inhibitor compound is a compound of the formula:

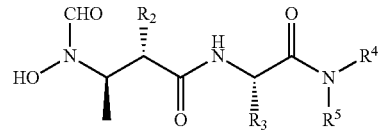

wherein $R^2$, $R^3$, $R^4$ and $R^5$ are as defined above. In some embodiments, $R^2$ is an aralkyl, or a functionalized aralkyl;

$R^3$ is alkyl, such as isopropyl or t-butyl; $R^4$ is hydrogen, alkyl, substituted alkyl, 2-(N-morphonline)ethyl, or a heterocycle; and $R^5$ is hydrogen or methyl; or a salt, prodrug, enantiomer, or diastereomer thereof.

In still other embodiments, the inhibitor compound is a compound of the formula:

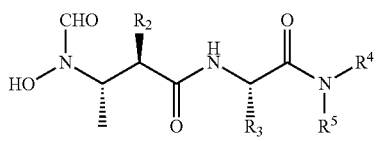

wherein $R^2$, $R^3$, $R^4$ and $R^5$ are as defined above. In some embodiments, $R^2$ is an aralkyl, or a functionalized aralkyl; $R^3$ is alkyl, such as isopropyl or t-butyl; $R^4$ is hydrogen, alkyl, substituted alkyl, cycloalkyl, substituted cycloalkyl, 2-ethoxyethyl, 2-isopropoxyethyl, 1-methoxybutan-2-yl, (tetrahydrofuran-2-yl)methyl, 2-(piperidin-1-yl)ethyl, 2-(N-sulfonylmorpholine)ethyl, 2-(N,N-dimethyl)ethyl, 2-hydroxyethyl, 2-(N-morphonline)ethyl, or a heterocycle; and $R^5$ is hydrogen or methyl; or a salt, prodrug, enantiomer, or diastereomer thereof.

In some embodiments, the ADAM10 inhibitor is further defined as:

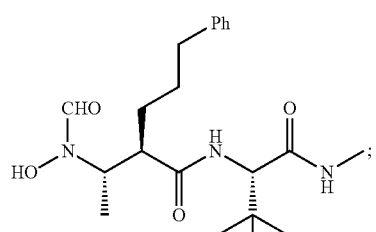

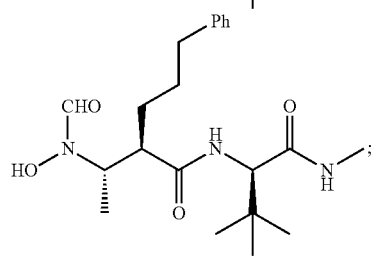

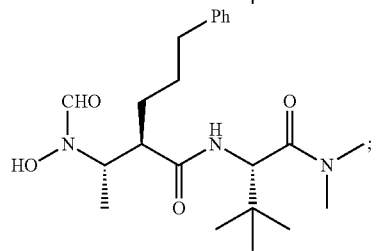

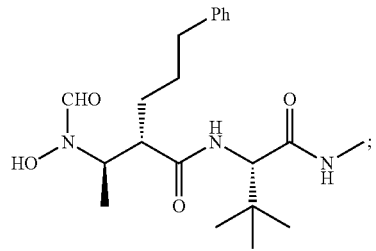

-continued

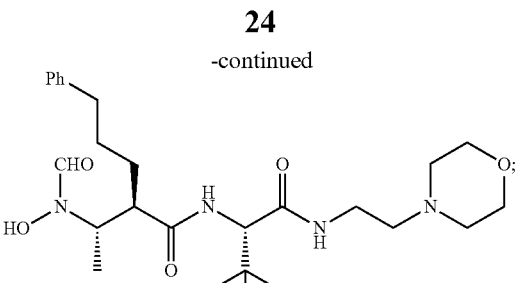

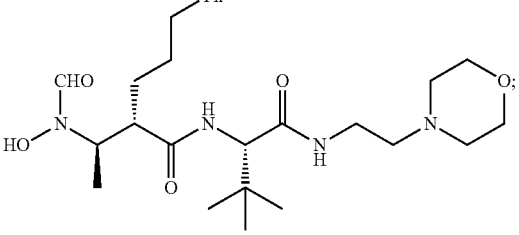

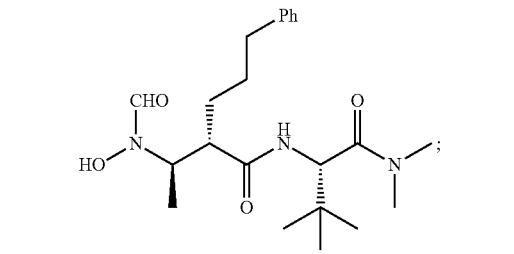

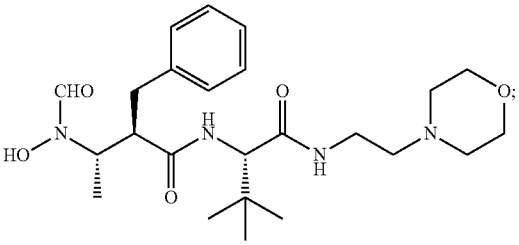

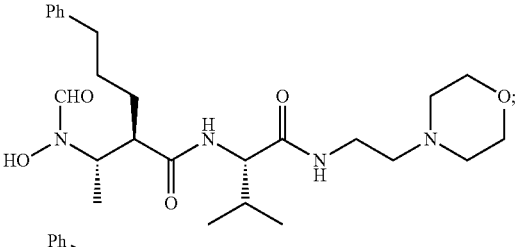

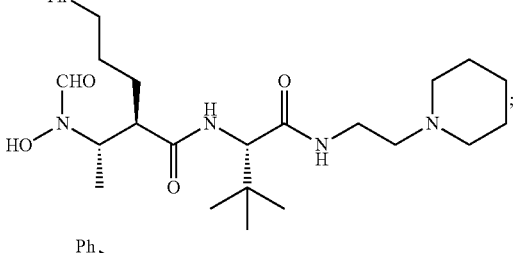

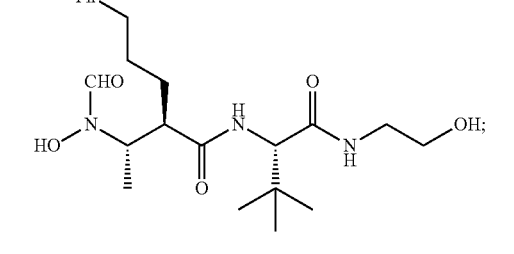

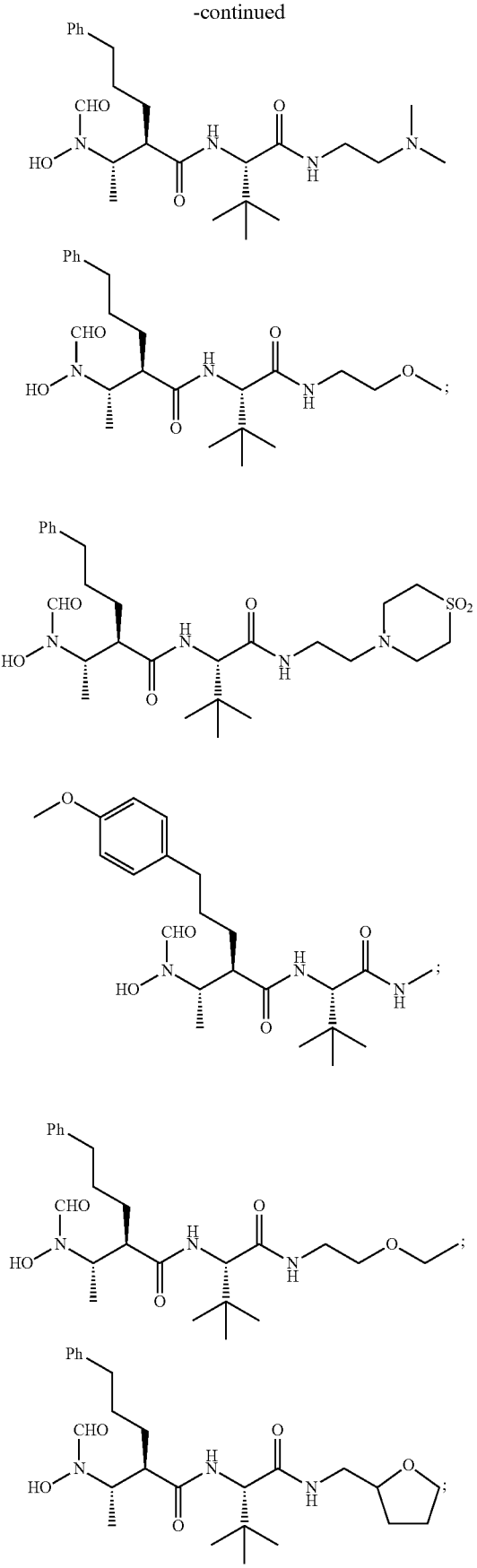
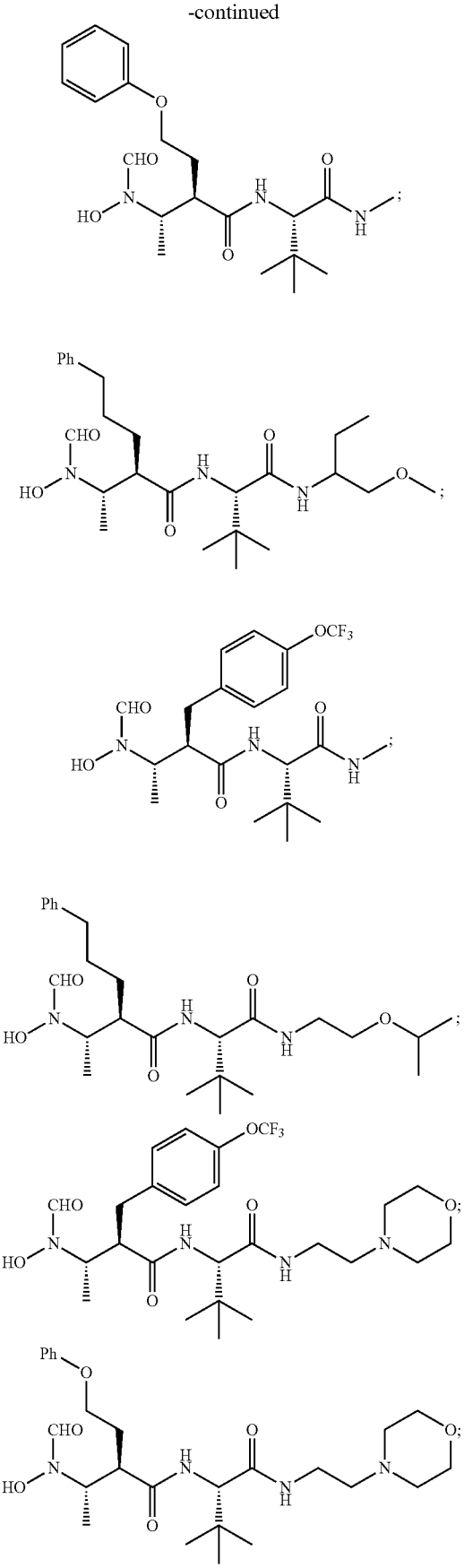

-continued
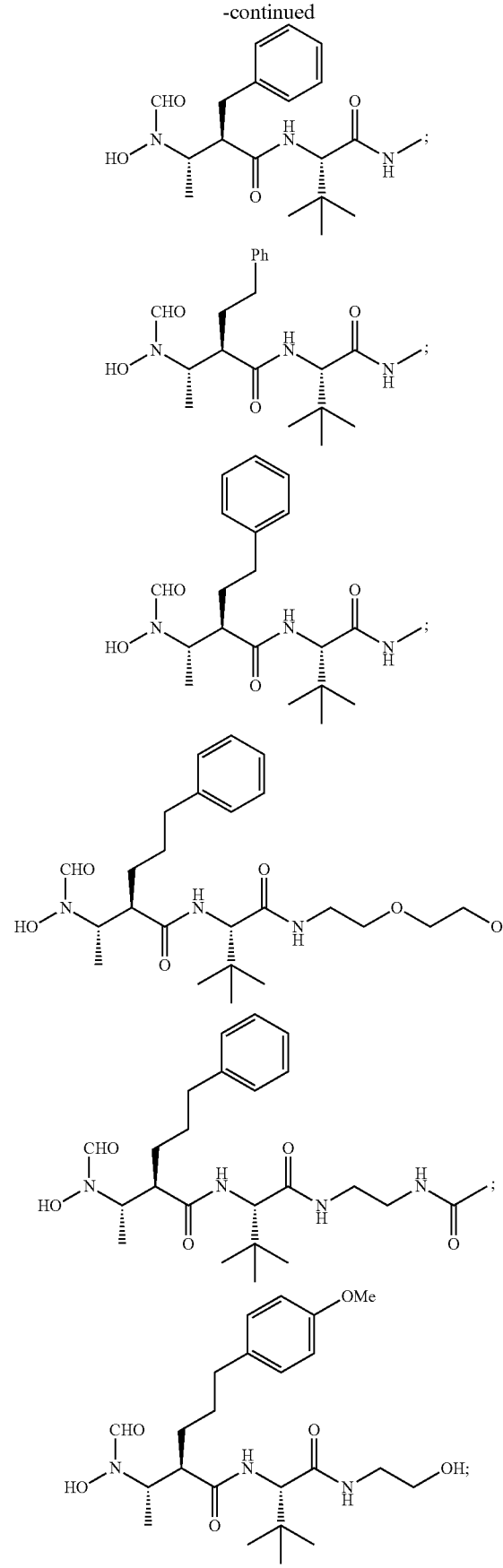
-continued
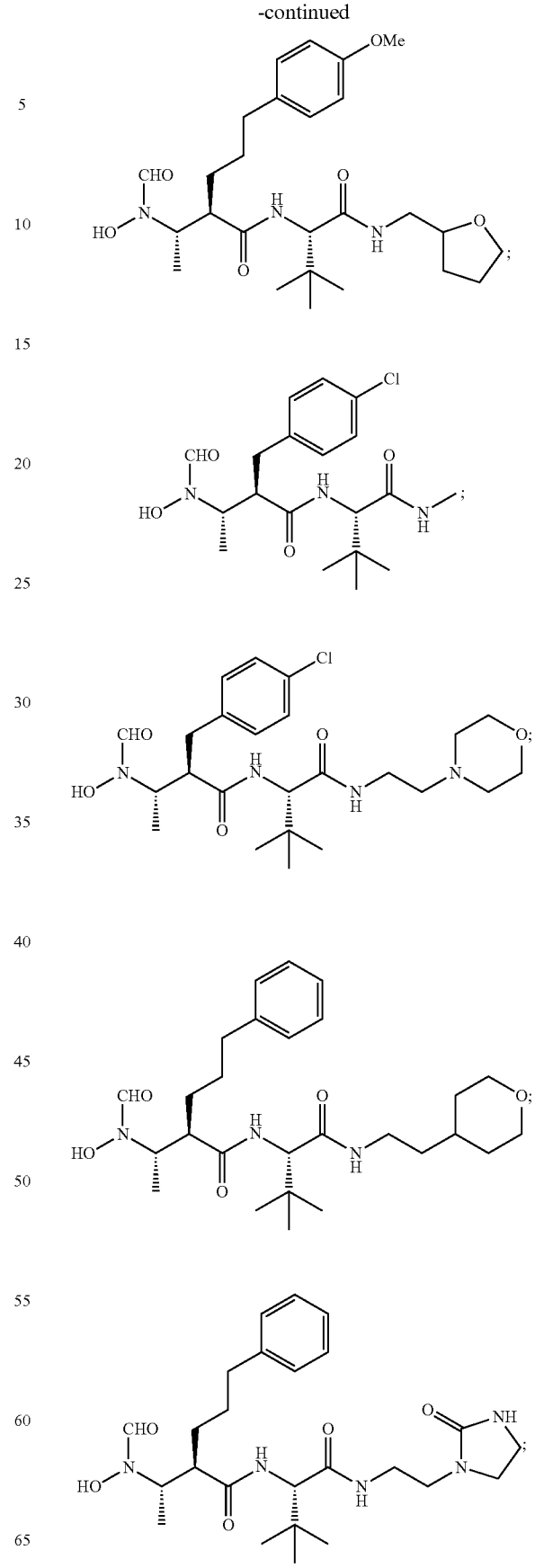

-continued

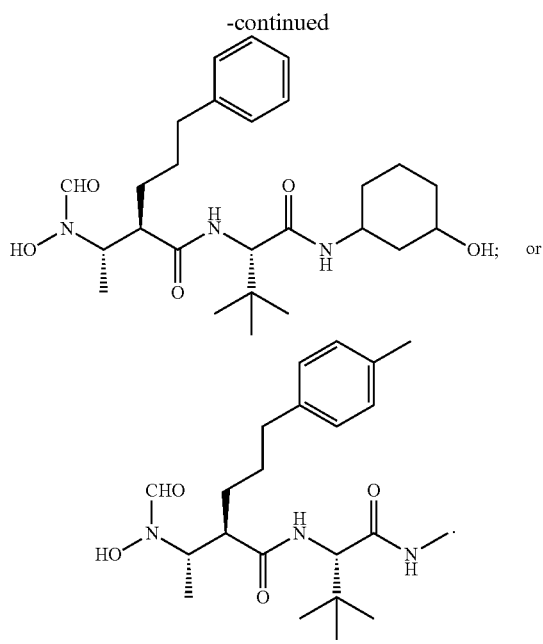

It is contemplated that derivatives, metabolites, and prodrugs of these compounds may also be used as ADAM10 inhibitors in some embodiments of the invention.

B. DEFINITIONS

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "sulfonyl" means —S(O)$_2$—; and "sulfinyl" means —S(O)—.

In the context of chemical formulas, the symbol "—" means a single bond, "=" means a double bond; and "≡" means triple bond. The symbol "- - - -" represents an optional bond, which if present is either single or double. The symbol "⚌" represents a single bond or a double bond. Thus, for example, the structure

includes the structures

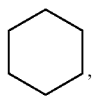, , 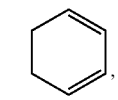,  and

.

As will be understood by a person of skill in the art, no one such ring atom forms part of more than one double bond. The symbol "〜", when drawn perpendicularly across a bond indicates a point of attachment of the group. It is noted that the point of attachment is typically only identified in this manner for larger groups in order to assist the reader in rapidly and unambiguously identifying a point of attachment. The symbol "◂" means a single bond where the group attached to the thick end of the wedge is "out of the page." The symbol "◁" means a single bond where the group attached to the thick end of the wedge is "into the page". The symbol "〜" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

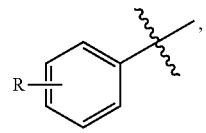

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

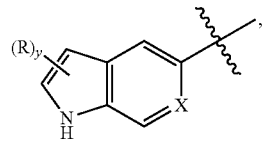

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. For example, "alkoxy$_{(C\leq 10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —OCH$_2$CH$_2$OH, —C(O)CH$_3$, —NC(O)CH$_3$, —N(CH$_3$)$_2$, —C(O)NH$_2$, —OC(O)CH$_3$, —S(O)$_2$NH$_2$, or imidazolidinone. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. When alkynyl is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethyl-phenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

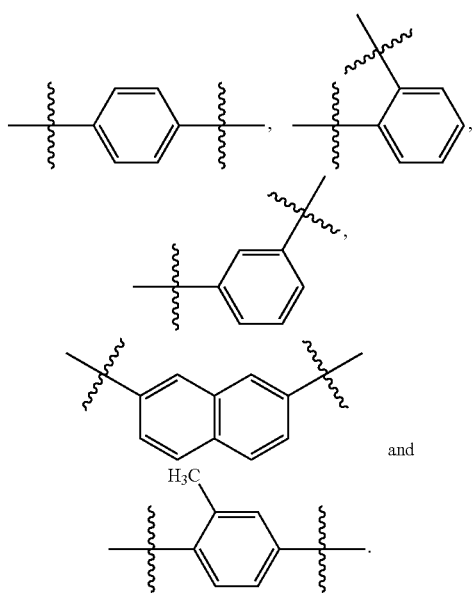

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

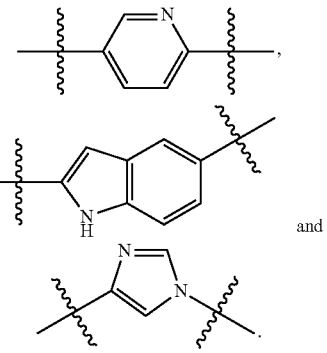

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treatment of a patient afflicted with one of the pathological conditions described herein comprises administering to such a patient an amount of compound described herein which is therapeutically effective in controlling the condition or in prolonging the survivability of the patient beyond that expected in the absence of such treatment. As used herein, the term "inhibition" of the condition also refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

Other abbreviations used herein are as follows: $^1$H-NMR is proton nuclear magnetic resonance, AcOH is acetic acid, Ar is argon, $CH_3CN$ is acetonitrile, CHN analysis is carbon/hydrogen/nitrogen elemental analysis, CHNCl analysis is carbon/hydrogen/nitrogen/chlorine elemental analysis, CHNS analysis is carbon/hydrogen/nitrogen/sulfur elemental analysis, DI water is deionized water, DIC is diisopropyl carbodiimide, DMA is N,N-dimethylacetamide, DMAP is 4-(N,N-dimethylamino)pyridine, DMF is N,N-dimethylformamide, EDCl is 1-(3-dimethylaminopropyl)-3-ethylcarbodiimide hydrochloride, EtOAc is ethyl acetate, EtOH is ethanol, FAB MS is fast atom bombardment mass spectroscopy, g is gram(s), HOBT is 1-hydroxybenzotriazole hydrate, HPLC is high performance liquid chromatography, IBCF is isobutylchloroformate, KSCN is potassium thiocyanate, L is liter, LiOH is lithium hydroxide, MEM is methoxyethoxymethyl, MEMCl is methoxyethoxymethyl chloride, MeOH is methanol, mg is milligram, $MgSO_4$ is magnesium sulfate, ml is milliliter, mL is milliliter, MS is mass spectroscopy, MTBE is methyl tert-butyl ether, $N_2$ is nitrogen, $NaHCO_3$ is sodium bicarbonate, NaOH is sodium hydroxide, $Na_2SO_4$ is sodium sulfate, NMM is N-methylmorpholine, NMP is N-methyl pyrrolidinone, NMR is nuclear magnetic resonance, $P_2O_5$ is phosphorous pentoxide, PTSA is para-toluenesulfonic acid, RPHPLC is reverse phase high performance liquid chromatography, RT is room temperature, TFA is trifluoroacetic acid, THF is tetrahydrofuran, TMS is trimethylsilyl, and $\Delta$ is heating the reaction mixture.

C. PHARMACEUTICAL FORMULATIONS AND ROUTES OF ADMINISTRATION

For administration to a mammal in need of such treatment, the compounds in a therapeutically effective amount are ordinarily combined with one or more excipients appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The pharmaceutical compositions useful in the present invention may be subjected to conventional pharmaceutical operations such as sterilization and/or may contain conventional pharmaceutical carriers and excipients such as preservatives, stabilizers, wetting agents, emulsifiers, buffers, etc.

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject.

In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

D. METHODS OF TREATMENT

Methods of the present invention include treatments for a disease or condition caused by a pathogen, for example, a *staphylococcus* or *streptococcus* pathogen, that stimulates or induces metalloprotease activity, in particular ADAM10 activity. An ADAM10 inhibitor can be given to treat a person infected with or exposed to *staphylococcus* or suspected of having been exposed to *staphylococcus* or at risk of developing a *Staphylococcus* infection. An ADAM10 inhibitor can also be given to treat a person infected with or exposed to *streptococcus* or suspected of having been exposed to *streptococcus* or at risk of developing a *Streptococcus* infection. Methods may be employed with respect to individuals who have tested positive for exposure to *staphylococcus* or *streptococcus* or who are deemed to be at risk for infection based on possible exposure.

In particular, embodiments concern methods of treatment for staphylococcal infection, particularly infections associated with the loss of endothelial or epithelial barrier function. These infections include, but are not limited to pneumonia, sepsis, corneal infections, respiratory infections, skin infections, sinus infections, infections of the central nervous system, or toxic shock syndrome. *Staphylococcus* infections of the skin that can be treated using the methods and compositions of the invention include, but are not limited to, dermonecrotic skin infections, eczema, secondary infections associated with eczema (including atopic dermatitis), impetigo, ecthyma, cellulitis, folliculitis, psoriasis, boils (furuncles and carbuncles) and sycosis.

In some embodiments, the treatment is administered in conjunction with *Staphylococcus* antigens or antibodies that bind *Staphylococcus* bacteria and/or their proteins and/or carbohydrates. Furthermore, in some examples, treatment comprises administration of other agents commonly used against bacterial infection, such as one or more antibiotics.

E. COMBINATION THERAPY

The compositions and related methods of the present invention, particularly administration of an ADAM10 inhibitor, may also be used in combination with the administration of traditional therapies. These include, but are not limited to, the administration of vaccines; anti-bacterial antibodies; or antibiotics such as streptomycin, ciprofloxacin, doxycycline, gentamycin, chloramphenicol, trimethoprim, sulfamethoxazole, ampicillin, tetracycline or various combinations of antibiotics.

In one aspect, it is contemplated that an ADAM10 inhibitor therapy is used in conjunction with other antibacterial treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other or within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines.

F. EXAMPLES

The following examples are included to demonstrate certain non-limiting aspects of the invention. It should be appreciated by those of skill in the art that the techniques disclosed in the examples that follow represent techniques discovered by the applicants to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1—Materials and Methods

LDH Release from Epithelial Cells—

Approximately $1.5 \times 10^4$ A549 cells were seeded in a 96-well plate in the presence of DMSO or ADAM10 inhibitor at a final concentration of 20 µM. Cells were incubated in the presence of DMSO or ADAM10 inhibitor for 16-20 h prior to addition of toxin. Medium containing DMSO or ADAM10 inhibitor was removed after pretreatment and replaced with incomplete F12K medium with DMSO, ADAM10 inhibitor and/or 10-20 µg/mL Hla. Cells were treated with toxin for 3 h and LDH released was measured using the Roche cytotoxicity detection kit per the manufacturer's instructions. All values were compared a detergent treated well and reported as % maximal lysis. Samples were performed in triplicate with data shown as the mean±standard error.

ADAM10 Metalloprotease Activity Assay—

A549 cells were seeded and pretreated in a 96-well plate as described above. After pretreatment for 16-20 h, cells were washed once with incomplete F12K medium. Cells were treated with 20 µg/mL Hla in the presence of DMSO or ADAM10 inhibitor for 1.5 h. The treatment was removed and cells were washed once with 25 mM Tris, pH 8.0. Approximately 10 µM of the fluorogenic peptide substrate (Mca-PLAQAV-Dpa-R—S—S—S—R—NH2; R&D Systems) was added in 25 mM Tris, pH 8.0 and incubated at 37° C. for 30 minutes. The contents of each well were transferred to a black-clear bottom 96-well plate and fluorescence was measured at an excitation wavelength at 320 nm and an emission wavelength at 405 nm. The average signal for F12K medium treated cells was subtracted from all values and reported as fluorescence units. There were five wells for each sample and the data are shown as mean±standard error.

Toxin-Epithelial Cell Binding Assay—

A549 cells were grown to 90% confluency in T75 flasks in complete F12K medium. One day prior to the experiment, the medium was replaced with complete medium containing DMSO or ADAM10 inhibitor at a final concentration of 20 µM. After 16-20 h of pretreatment, cells were harvested and counted. Approximately 5×10$^5$ cells in 0.5 mL of complete medium were incubated in the presence of 10 µL of diluted radiolabeled Hla. Radiolabeled toxin was generated using in vitro transcription and translation in the presence of an *Escherichia coli* extract and S$^{35}$-labelled methionine (Promega). Cells and radiolabeled toxin were incubated for a total of 5 min and the reaction was stopped with the addition of cold PBS. Unbound toxin was removed after centrifugation at 13,000×g for 2 min. Cells were washed twice with cold PBS and then added to scintillation liquid. Radioactivity was measured using a scintillation counter with a standard for $^{35}$S-methionine and values are reported as counts per minute (cpm). All samples were performed in triplicate with data shown as the mean±standard error.

Hemolysis Assay Using Rabbit Erythrocytes—

Approximately 2.5×10$^8$ rabbit erythrocytes in 180 µL of PBS with DMSO or ADAM10 inhibitor were incubated at room temperature for 1 h. DMSO or ADAM10 inhibitor 2-fold dilutions were made serially starting at 80 µM down 40 nM. Rabbit erythrocytes were transferred to a 96-well plate containing 20 µL of 10 µg/mL of Hla and incubated for an additional hour with rocking One set of wells were treated with 25% Triton-X100 in 20 µL for a maximal lysis reading. After treatment, 100 µL of supernatant was harvested by centrifugation at 100×g for 10 min and transferred to a fresh 96-well plate. Hemolysis was measured at an absorbance at 450 nm and the data are reported as % hemolysis after comparison to the detergent treated sample. All samples were performed in triplicate with data shown as the mean±standard error. The IC$_{50}$ calculations were determined using the one-site binding model in Prism 5.0.

EXAMPLE 2-SYNTHESIS SCHEMES

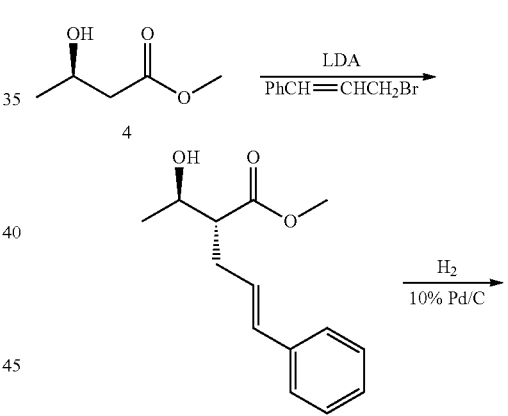

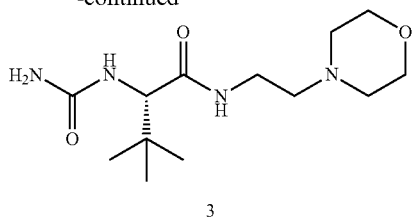

(R)-2-((tert-butoxycarbonyl)amino)-3,3-dimethylbutanoic acid 1 (2 g, 8.7 mmol) was dissolved in dichloromethane (16 mL). To it, was added carbonyldiimidazole (CDI, 1.47 g, 1.05 eq.) and stirred for 1 h at rt. Morpholinylethylamine (1.65 g, 1.5 eq.) and triethylamine (2 ml, 3 eq.) were added. The resulting mixture was stirred at rt. overnight. It was diluted with CH$_2$Cl$_2$ and was washed with 1N HCl, NaCl (sat.) and dried (Na$_2$SO$_4$). Concentration gave 2.96 g of amide 2.

The amide 2 (2.96 g, 8.6 mmol) in 3.5 ml of dichloromethane was cooled to 0° C. and was added trifluoroacetic acid (3.5 ml). It was stirred at 0° C. and was allowed to warm to rt overnight. Volatiles were removed and the residue was basified to pH >10. The product was extracted with 2×50 ml of 4:1 of CH$_2$Cl$_2$/iPrOH. The organic layer was washed with NaCl (sat.) and was dried (MgSO$_4$), it was filtered and concentrated. 1.88 g of the product ((R)-2-amino-3,3-dimethyl-N-(2-morpholinoethyl)butanamide) 3 was obtained.

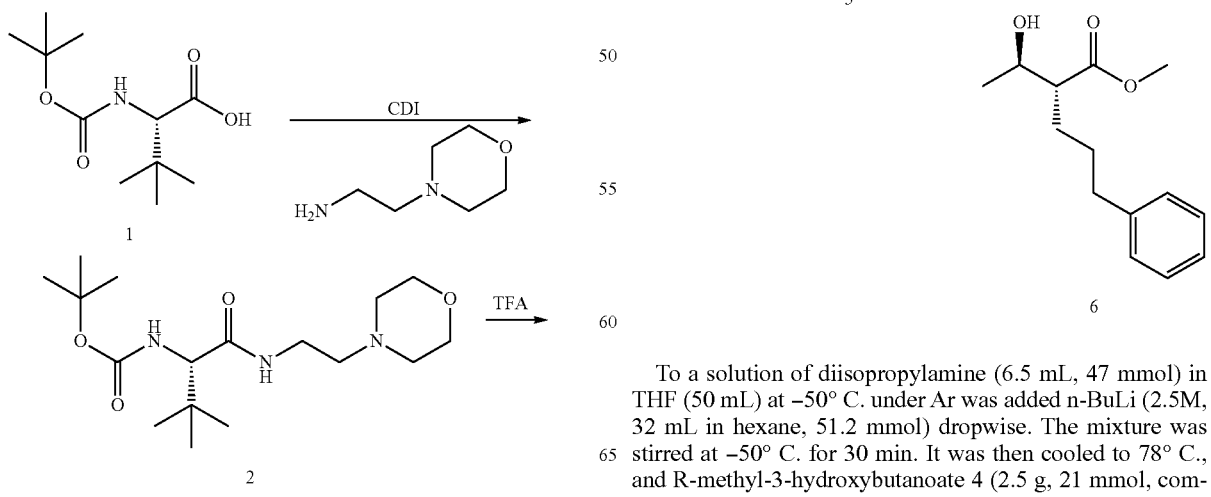

To a solution of diisopropylamine (6.5 mL, 47 mmol) in THF (50 mL) at −50° C. under Ar was added n-BuLi (2.5M, 32 mL in hexane, 51.2 mmol) dropwise. The mixture was stirred at −50° C. for 30 min. It was then cooled to 78° C., and R-methyl-3-hydroxybutanoate 4 (2.5 g, 21 mmol, compound) was added. The resulting mixture was stirred for another 30 min before 3-bromo-prop-2-enylbenzene (4.59 g, 23 mmol) in 1 ml of HMPA was added. The mixture was stirred at 0° C. and was allowed to warm to room temperature overnight. It was quenched with 3 ml of NH₄Cl (sat.) and was then poured into 1N HCl ice solution. The mixture was diluted with EtOAc. The organic layer was separated, washed with H₂O, NaCL (sat.) and dried over Na₂SO₄. Concentration under vacuum afforded 5.1 g of crude product, which was purified by Biotage with 5-35% EtOAc in Hexane. The desired product 5 ((R,E)-methyl 2-((R)-1-hydroxyethyl)-5-phenylpent-4-enoate) was obtained in 3.2 g (65%).

To a solution of 3.2 g of (R,E)-methyl 2-((R)-1-hydroxyethyl)-5-phenylpent-4-enoate 5 (13.7 mmol) was dissolved in 40 mL of MeOH was added 35 mg of 10% Pd/C and the mixture was degassed. It was then stirred under H₂ balloon at room temperature for 2 h. It was then filtered through celite and concentrated. The product 6 ((R)-methyl 2-((R)-1-hydroxyethyl)-5-phenylpentanoate) was obtained in 3.11 g (96%).

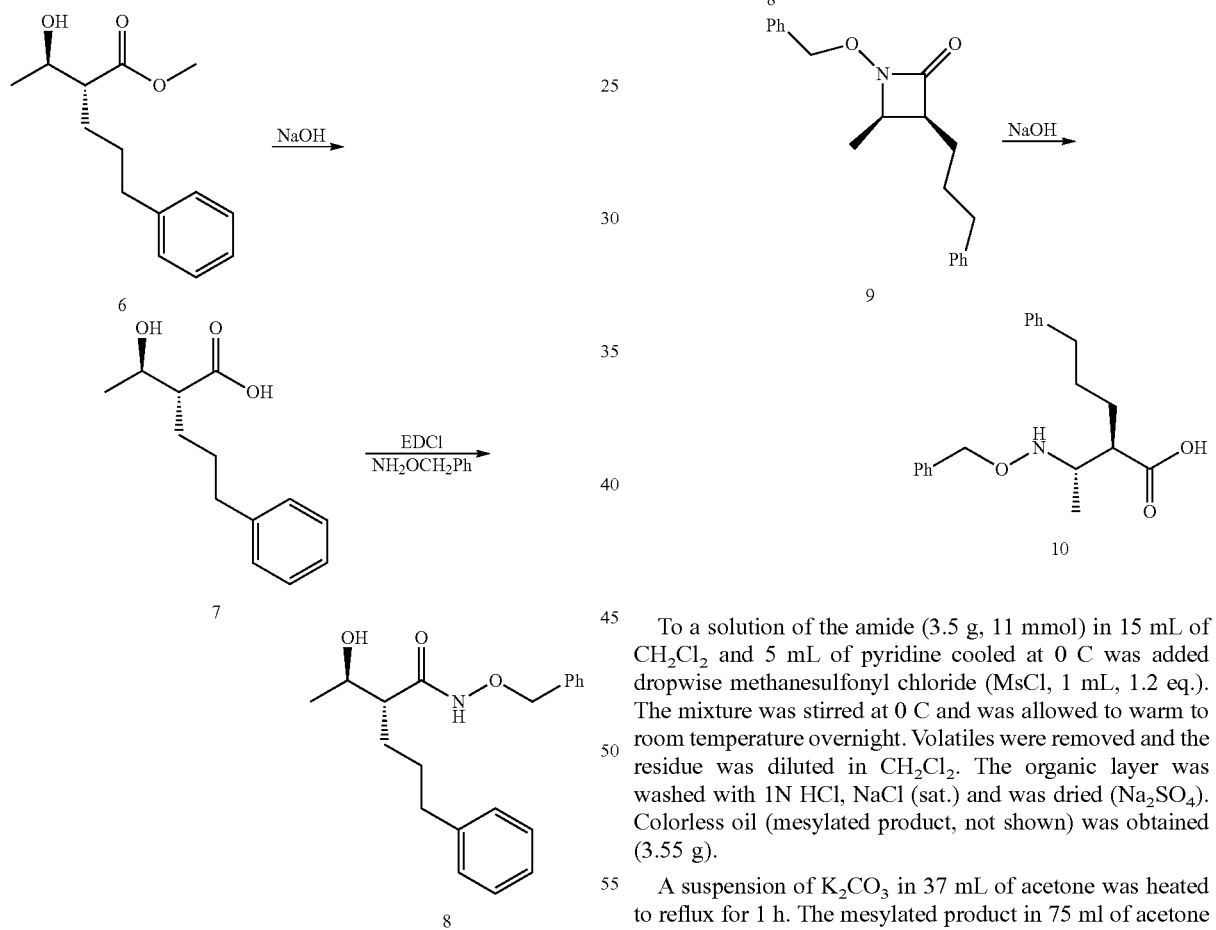

To a solution of (R)-methyl 2-((R)-1-hydroxyethyl)-5-phenylpentanoate 6 (3.11 g, 13.2 mmol) in 30 ml of THF and 10 ml of MeOH was added 2M of NaOH (9.88 mL, 1.5 eq.). The mixture was stirred at room temperature overnight. The volatiles were removed. The residue was acidified with 1N HCl to PH=3. It was extracted with EtOAc (2X). The organic layer was washed with H2O, NaCl (sat.) and dried over Na₂SO₄. It was concentrated to give 2.9 g of (R)-2-((R)-1-hydroxyethyl)-5-phenylpentanoic acid 7.

To a solution of the acid 7 (2.9 g, 13.1 mmol) in dichloromethane (25 ml) were added EDCI (2.75 g, 1.1 eq.) and benzyloxyamine (1.69 g, 1.05 eq.). The resulting mixture was stirred at room temperature overnight. It was then diluted with dichloromethane, washed with 1N HCl, NaHCO₃ (sat) and NaCl (sat.). The mixture was dried over Na₂SO₄, and concentrated. Silica-gel column purification gave 3.5 g of product 8 (82%).

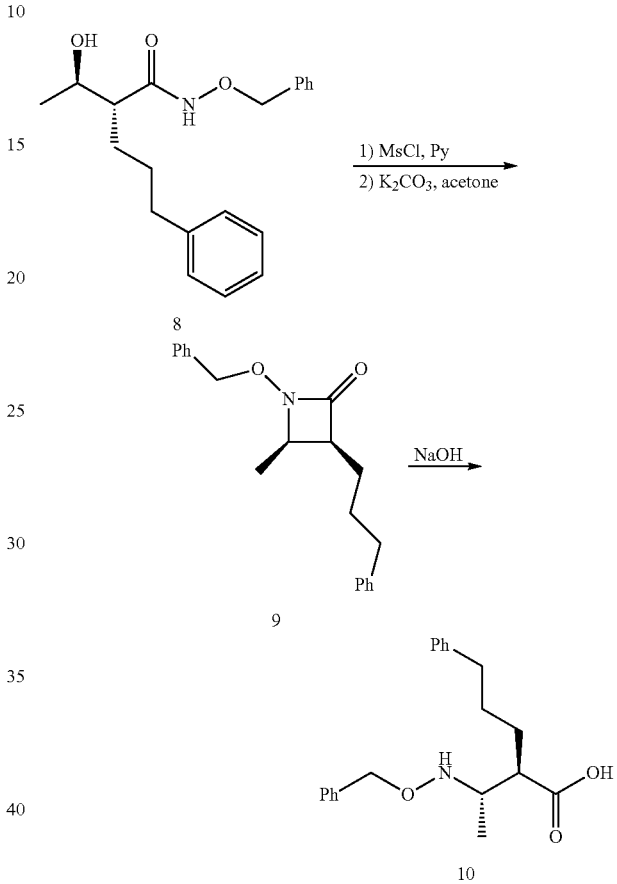

To a solution of the amide (3.5 g, 11 mmol) in 15 mL of CH₂Cl₂ and 5 mL of pyridine cooled at 0 C was added dropwise methanesulfonyl chloride (MsCl, 1 mL, 1.2 eq.). The mixture was stirred at 0 C and was allowed to warm to room temperature overnight. Volatiles were removed and the residue was diluted in CH₂Cl₂. The organic layer was washed with 1N HCl, NaCl (sat.) and was dried (Na₂SO₄). Colorless oil (mesylated product, not shown) was obtained (3.55 g).

A suspension of K₂CO₃ in 37 mL of acetone was heated to reflux for 1 h. The mesylated product in 75 ml of acetone was added and the resulting mixture was heated for 28 h. It was cooled, filtered and concentrated. It was purified using biotage and 2.6 g of lactam 9 (79%).

Lactam 9 (2.6 g, 8.5 mmol) was dissolved in 30 mL of dioxane was mixed with 1M NaOH (12.7 ml, 1.5 eq.). It was stirred at rt overnight. Volatiles were removed and the residue was acidified with 1N HCl to pH<4. The product was extracted twice with EtOAc. The organic layer was washed with H₂O, NaCl (sat.) and dried (Na₂SO₄). Concentration gave 2.8 g of the acid 10.

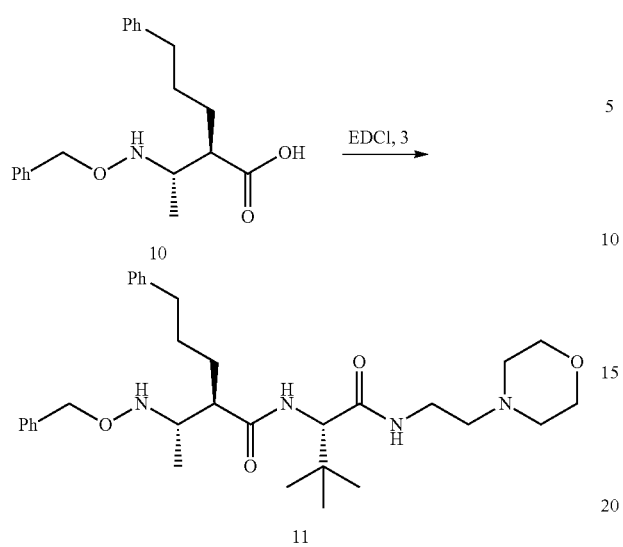

The acid 10 ((R)-2-((S)-1-((benzyloxy)amino)ethyl)-5-phenylpentanoic acid, 0.327 g, 1 mmol) and 3 ((R)-2-amino-3,3-dimethyl-N-(2-morpholinoethyl)butanamide, 0.22 g, 1 mmol) were dissolved in 10 ml of DMF. To the above solution were added HOBT (0.148 g, 1.1 eq.), DMAP (0.134 g, 1.1 eq.) and EDCI (0.23 g, 1.2 eq.). The resulting mixture was stirred at rt for 48 h. It was then diluted with citric acid (1N solution) and extracted twice with EtOAc. The organic layer was washed with NaHCO₃ (sat.), water (3X), NaCl (sat.) and dried (Na₂SO₄). Concentration gave 0.6 g of the crude product, which was purified on Biotage to give 25-50% of the desired product 11 (100 mg, (R)-2-((S)-1-((benzyloxy)amino)ethyl)-N—((S)-3,3-dimethyl-1-((2-morpholinoethyl)amino)-1-oxobutan-2-yl)-5-phenylpentanamide).

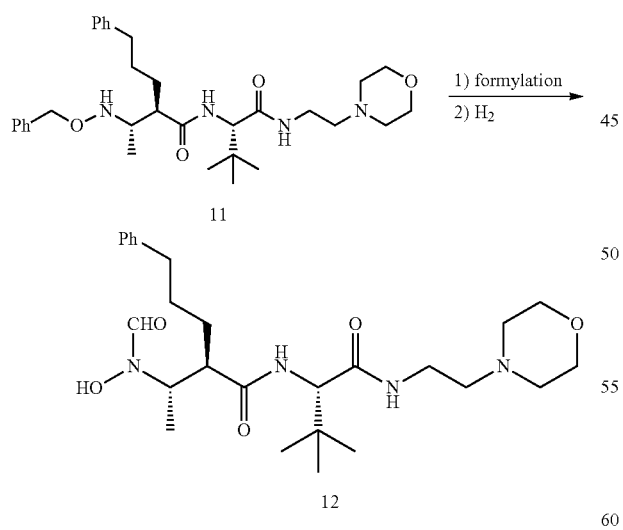

To a solution of CDI (0.18 g, 5 eq) in 5 ml of THF at 0 C was added formic acid (95%, 0.044 ml, 5 eq.). After the mixture was stirred at 0° C. for 1 h, (R)-2-((S)-1-((benzyloxy)amino)ethyl)-N—((S)-3,3-dimethyl-1-((2-morpholinoethyl)amino)-1-oxobutan-2-yl)-5-phenylpentanamide 11 (100 mg, 0.22 mmol) in 5 ml of THF was added and the resulting solution was stirred at 0° C. overnight. It was then diluted with EtOAc and was washed with NaHCO₃ (sat.), H₂O, NaCl (sat.). It was dried (Na₂SO₄), concentrated (W=0.11 g), and used directly for the next step.

(R)-2-((S)-1-(N-(benzyloxy)formamido)ethyl)-N—((S)-3,3-dimethyl-1-(2-morpholinoethyl)amino)-1-oxobutan-2-yl)-5-phenylpentanamide 11 (0.10 g, 0.21 mmol) was dissolved in 5 ml of methanol. It was then mixed with 10 mg of 10% Pd/C and degassed. The mixture was stirred under hydrogen balloon at rt for 2.5 hr. It was then filtered through celite and concentrated. The product 12 was purified on preparative TLC with 8% MeOH in CH₂Cl₂ and recrystallized by CH₂Cl₂/Hex (78 mg, 91%).

SRI-028597

(R)—N—((S)-3,3-dimethyl-1-((2-morpholinoethyl)amino)-1-oxobutan-2-yl)-2-((S)-1-(N-hydroxyformamido)ethyl)-5-phenylpentanamide

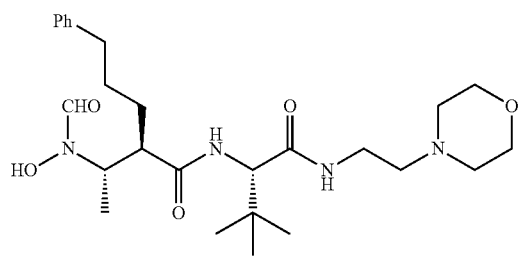

¹H NMR (400 MHz, DMSO-d₆): δ (ppm) 9.77 &9.37 (s, 1H), 7.8-8.2 (m, 3H), 7.1-7.2 (m, 5H), 4.23 (d, J=9.6, 1H), 4.3 & 3.7 (m, 1H), 3.3 (m, 4H), 3.0-3.2 (m, 2H), 2.8 (m, 1H), 2.48 (m, 4H), 2.2 (m, 8H), 1.3 (d, J=9.3, 3H), 0.91 (s, 9H). MS (ESI, m/e): 491.26 (M+H)⁺. UV: λ$_{max}$=206 nM. HPLC: Water XBridge C18, 5 u, 4.6×250 mm; flow 1.0 ml/min; Waters 996 PDA detection at 215 nm; solvent 10-95% Acetonitrile (0.1% TFA) in H₂O (0.1% TFA) over 20 min; retention time 9.17 min; 100%.

SRI-028595

(R)—N—((R)-3,3-dimethyl-1-(methylamino)-1-oxobutan-2-yl)-2-((S)-1-(N-hydroxyformamido)ethyl)-5-phenylpentanamide

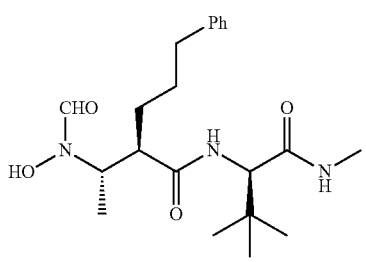 [SMILES: CNC(=O)[C@H](NC(=O)[C@H](CCCc1ccccc1)[C@H](C)N(O)C=O)C(C)(C)C]

¹H NMR (400 MHz, DMSO-d₆): δ (ppm) 9.77 &9.37 (s, 1H), 7.8-8.2 (m, 3H), 7.1-7.2 (m, 5H), 4.23 (d, J=9.6, 1H), 4.3 & 3.7 (m, 1H), 2.8 (m, 2H), 2.55 (d, J=4.5, 3H), 2.4 (m, 1H), 1.4 (m, 4H), 1.1 (d, J=9.3, 3H), 0.91 (s, 9H).

MS (ESI, m/e): 391.99 (M+H)⁺. UV: λ_max=207 nM. HPLC: Water XBridge C18, 5 u, 4.6×250 mm; flow 1.0 ml/min; Waters 996 PDA detection at 215 nm; solvent 10-95% Acetonitrile (0.1% TFA) in H$_2$O (0.1% TFA) over 20 min; retention time 11.2 min; 100%.

SRI-028596

(R)—N—((S)-1-(dimethylamino)-3,3-dimethyl-1-oxobutan-2-yl)-2-((S)-1-(N-hydroxyformamido)ethyl)-5-phenylpentanamide

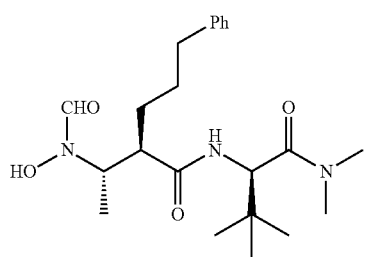 [SMILES: C[C@@H]([C@@H](CCCc1ccccc1)C(=O)N[C@@H](C(=O)N(C)C)C(C)(C)C)N(O)C=O]

$^1$H NMR (400 MHz, DMSO-d$_6$): δ (ppm) 9.77 &9.37 (s, 1H), 7.8-8.2 (m, 3H), 7.1-7.2 (m, 5H), 4.75 (d, J=9.2, 1H), 4.3 & 3.7 (m, 1H), 2.8 (m, 1H), 2.4 (s, 6H), 2.3 (m, 1H), 1.4 (m, 6H), 1.08 (d, J=9.3, 3H), 0.92 (s, 9H).

MS (ESI, m/e): 405.95 (M+H)⁺. UV: λ_max=207 nM. HPLC: Water XBridge C18, 5 u, 4.6×250 mm; flow 1.0 ml/min; Waters 996 PDA detection at 215 nm; solvent 10-95% Acetonitrile (0.1% TFA) in H$_2$O (0.1% TFA) over 20 min; retention time 12.3 min; 100%.

SRI-028598

(S)—N—((S)-3,3-dimethyl-1-(methylamino)-1-oxobutan-2-yl)-2-(R)-1-(Nhydroxyformamido)ethyl)-5-phenylpentanamide

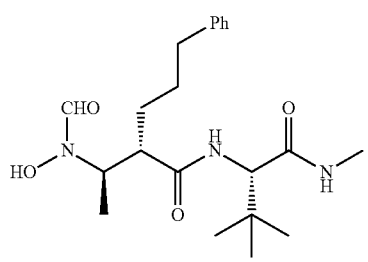 [SMILES: CNC(=O)[C@@H](NC(=O)[C@@H](CCCc1ccccc1)[C@@H](C)N(O)C=O)C(C)(C)C]

$^1$H NMR (400 MHz, CDCl$_3$): δ (ppm) 8.4 & 7.8 (s, 1H), 7.4-7.7 (m, 3H), 7.0-7.2 (m, 5H), 4.45 (m, 1H), 3.78 (m, 1H), 2.8 (m, 3H), 2.5 (m, 2H), 1.6 (m, 2H), 1.4 (m, 2H), 1.08 (d, J=9.3, 3H), 0.92 (s, 9H).

MS (ESI, m/e): 414 (M+H)⁺. UV: λ_max=207 nM. HPLC: Water XBridge C18, 5 u, 4.6×250 mm; flow 1.0 ml/min; Waters 996 PDA detection at 205 nm; solvent 10-90% Acetonitrile (0.1% TFA) in H$_2$O (0.1% TFA) over 20 min; retention time 12.4 min; 96.1%.

SRI-028599

(S)—N—((S)-3,3-dimethyl-1-((2-morpholinoethyl)amino)-1-oxobutan-2-yl)-2-((R)-1-(N-hydroxyformamido)ethyl)-5-phenylpentanamide

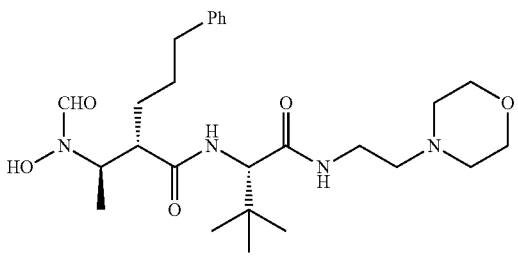 [SMILES: C[C@H]([C@H](CCCc1ccccc1)C(=O)N[C@H](C(=O)NCCN1CCOCC1)C(C)(C)C)N(O)C=O]

$^1$H NMR (400 MHz, CDCl$_3$): δ (ppm) 8.4 & 7.9 (s, 1H), 7.06-7.29 (m, 5H), 6.8 (m, 1H), 6.6 (m, 1H), 4.27 (d, J=9.2, 1H), 4.5 & 4.1 (m, 1H), 3.68 (m, 4H), 3.4 (m, 1H), 3.2 (m, 1H), 2.4-2.6 (m, 8H), 1.5 (m, 4H), 1.2 (d, J=9.3, 3H), 0.90 (s, 9H).

MS (ESI, m/e): 491 (M+H)⁺. UV: λ_max=207 nM. HPLC: Water XBridge C18, 5 u, 4.6×250 mm; flow 1.0 ml/min; Waters 996 PDA detection at 205 nm; solvent 10-90% Acetonitrile (0.1% TFA) in H$_2$O (0.1% TFA) over 20 min; retention time 10.9 min; 95.4%.

SRI-028600

(S)—N—((S)-1-(dimethylamino)-3,3-dimethyl-1-oxobutan-2-yl)-2-((R)-1-(N-hydroxyformamido)ethyl)-5-phenylpentanamide

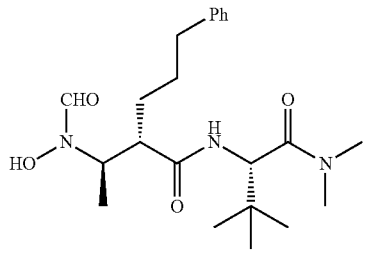 [SMILES: C[C@H]([C@H](CCCc1ccccc1)C(=O)N[C@H](C(=O)N(C)C)C(C)(C)C)N(O)C=O]

$^1$H NMR (400 MHz, CDCl$_3$): δ (ppm) 8.4 & 7.9 (s, 1H), 7.11-7.27 (m, 5H), 6.63 (d, J=9.6, 1H), 4.90 (d, J=9.5, 1H), 4.6 (m, 1H), 3.82 (m, 1H), 3.22 (m, 4H), 2.95 (m, 4H), 2.6 (m, 4H), 1.58 (m, 6H), 1.18 (d, J=9.3, 3H), 0.98 (m, 9H).

MS (ESI, m/e): 405 (M+H)⁺. UV: λ_max=207 nM. HPLC: Water XBridge C18, 5 u, 4.6×250 mm; flow 1.0 ml/min; Waters 996 PDA detection at 205 nm; solvent 10-90% Acetonitrile (0.1% TFA) in H$_2$O (0.1% TFA) over 20 min; retention time 13.4 min; 96.0%.

53

(S)-2-((2R,3S)-2-BENZYL-3-(N-HYDROXYFOR-MAMIDO)BUTANAMIDO)-N,3,3-TRIMETH-YLBUTANAMIDE

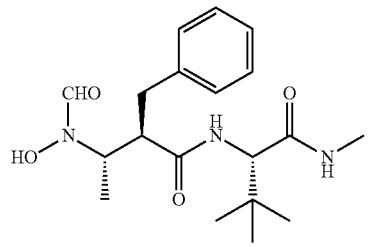 [SMILES: CNC(=O)[C@@H](NC(=O)[C@H](Cc1ccccc1)[C@H](C)N(O)C=O)C(C)(C)C]

¹H NMR (300 MHz, MeOH-d₄): δ (ppm) 8.38 & 8.11 (s, 1H), 7.13 (m, 5H), 4.82 (s, 2H), 4.6 & 3.9 (m, 1H), 4.03 (s, 1H), 3.30 (m, 2H), 3.12 (m, 1H), 2.6-2.8 (m, 2H), 2.53 (s, 3H), 1.33 (d, J=6.2, 3H), 0.89 (s, 9H).

MS (ESI, m/e): 362.54 (M+H)⁺. UV: $\lambda_{max}$=220 nM. HPLC: Water XBridge C18, 5 u, 4.6×250 mm; flow 1.0 ml/min; Waters 996 PDA detection at 205 nm; solvent 10-90% Acetonitrile (0.1% TFA) in H₂O (0.1% TFA) over 20 min; retention time 9.27 min; 98.3%.

SRI-028602

(S)-2-((2R,3S)-2-benzyl-3-(N-hydroxyformamido)butanamido)-3,3-dimethyl-N-(2-morpholinoethyl)butanamide

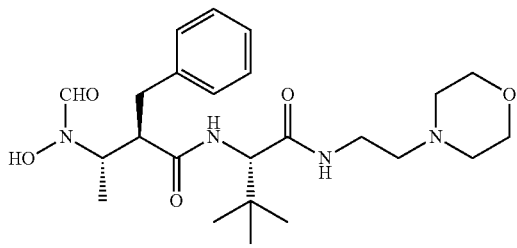 [SMILES: C[C@@H]([C@@H](Cc1ccccc1)C(=O)N[C@H](C(=O)NCCN1CCOCC1)C(C)(C)C)N(O)C=O]

¹H NMR (400 MHz, CDCl₃): δ (ppm) 8.00 (s, 1H), 7.23 (m, 5H), 5.99 (m, 1H), 4.0 (m, 1H), 3.71 (m, 2H), 2.6-3.3 (m, 4H), 2.45 (m, 4H), 0.9-1.3 (m, 4H), 0.84 (m, 9H).

MS (ESI, m/e): 463.37 (M+H)⁺. UV: $\lambda_{max}$=220 nM. HPLC: Water XBridge C18, 5 u, 4.6×250 mm; flow 1.0 ml/min; Waters 996 PDA detection at 205 nm; solvent 10-90% Acetonitrile (0.1% TFA) in H₂O (0.1% TFA) over 20 min; retention time 7.41 min; 93.3%.

54

SRI-028622

(S)-2-((2R,3S)-3-(N-hydroxyformamido)-2-(4-(trifluoromethoxy)benzyl)butanamido)-3,3-dimethyl-N-(2-morpholinoethyl)butanamide

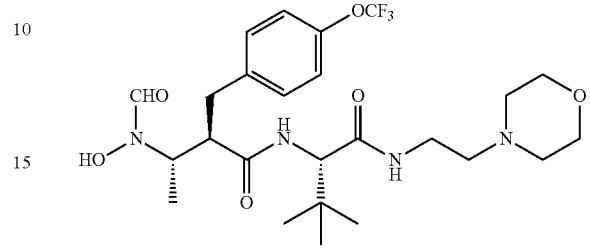

¹H NMR (400 MHz, MeOH-d₄): δ (ppm) 8.38 & 8.11 (s, 1H), 7.3 (m, 5H), 5.5 (s, 2H), 4.6 & 4.1 (m, 1H), 4.23 (m, 1H), 3.30 (m, 2H), 3.12 (m, 1H), 2.6-2.8 (m, 2H), 2.53 (s, 3H), 1.33 (d, J=6.2, 3H), 0.89 (s, 9H).

MS (ESI, m/e): 547.28 (M+H)⁺. UV: $\lambda_{max}$=207 nM. HPLC: Water XBridge C18, 5 u, 4.6×250 mm; flow 1.0 ml/min; Waters 996 PDA detection at 205 nm; solvent 10-90% Acetonitrile (0.1% TFA) in H₂O (0.1% TFA) over 20 min; retention time 8.6 min; 100%.

SRI-028623

(S)-2-((2R,3S)-3-(N-hydroxyformamido)-2-(4-(trifluoromethoxy)benzyl)butanamido)-N,3,3-trimethylbutanamide

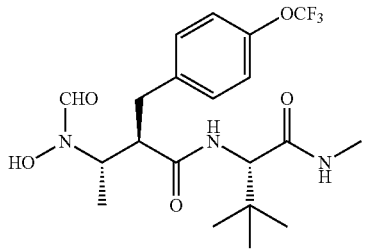 [SMILES: CNC(=O)[C@@H](NC(=O)[C@H](Cc1ccc(OC(F)(F)F)cc1)[C@H](C)N(O)C=O)C(C)(C)C]

¹H NMR (400 MHz, MeOH-d₄): δ (ppm) 8.38 & 8.11 (s, 1H), 7.2 (m, 5H), 5.0 (s, 2H), 4.6 & 4.1 (m, 1H), 4.2 (s, 1H), 3.40 (s, 3H), 3.2 (m, 1H), 2.6-2.8 (m, 2H), 1.33 (d, J=6.2, 3H), 0.99 (s, 9H).

MS (ESI, m/e): 447.97 (M+H)⁺. UV: $\lambda_{max}$=207 nM. HPLC: Water XBridge C18, 5 u, 4.6×250 mm; flow 1.0 ml/min; Waters 996 PDA detection at 205 nm; solvent 10-90% Acetonitrile (0.1% TFA) in H₂O (0.1% TFA) over 20 min; retention time 10.22 min; 100%.

SRI-028604

(R)-2-((S)-1-(N-hydroxyformamido)ethyl)-N—((S)-3-methyl-1-((2-morpholinoethyl)amino)-1-oxobutan-2-yl)-5-phenylpentanamide

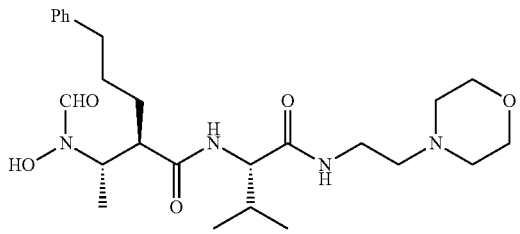 [SMILES: CC(C)[C@H](NC(=O)[C@H](CCCc1ccccc1)[C@H](C)N(O)C=O)C(=O)NCCN1CCOCC1]

¹H NMR (400 MHz, DMSO-d₆): δ (ppm) 9.75 &9.38 (s, 1H), 8.2 & 7.96 (s, 1H), 8.2 (m, 1H), 7.78 (m, 1), 7.1-7.2 (m, 5H), 4.3 & 3.75 (m, 1H), 4.07 (m, 1H), 3.5 (m, 4H), 3.13 (m, 2H), 2.5-2.7 (m, 2H), 2.48 (m, 1H), 2.2 (m, 4H), 1.4 (m, 4H), 1.09 (d, J=9.3, 3H), 0.84 (m, 6H).

MS (ESI, m/e): 477.38 (M+H)⁺. UV: $\lambda_{max}$=203.7 nM. HPLC: Water XBridge C18, 5 u, 4.6×250 mm; flow 1.0 ml/min; Waters 996 PDA detection at 215 nm; solvent 10-95% Acetonitrile (0.1% TFA) in H₂O (0.1% TFA) over 20 min; retention time 10.0 min; 98.1%.

SRI-028603

(R)—N—((S)-1-((2-hydroxyethyl)amino)-3,3-dimethyl-1-oxobutan-2-yl)-2-((S)-1-(N-hydroxyformamido)ethyl)-5-phenylpentanamide

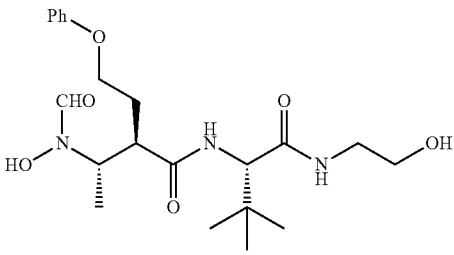

¹H NMR (400 MHz, DMSO-d₆): δ (ppm) 9.75 & 9.38 (s, 1H), 7.9-8.1 (m, 3H), 7.1-7.2 (m, 5H), 4.57 (t, J=5.4, 1H), 4.3-3.7 (m, 1H), 4.26 (d, J=9.5, 1H), 3.3 (m, 1H), 3.07 (m, 2H), 2.8 (m, 1H), 2.5 (m, 1H), 2.4 (m, 1H), 1.38 (m, 4H), 1.08 (d, J=9.3, 3H), 0.90 (s, 9H).

MS (ESI, m/e): 422.10 (M+H)⁺. UV: $\lambda_{max}$=208.6 nM. HPLC: Water XBridge C18, 5 u, 4.6×250 mm; flow 1.0 ml/min; Waters 996 PDA detection at 215 nm; solvent 10-95% Acetonitrile (0.1% TFA) in H₂O (0.1% TFA) over 20 min; retention time 9.3 min; 97.6%.

SRI-028624

(S)-2-((2R,3S)-3-(N-hydroxyformamido)-2-(2-phenoxyethyl)butanamido)-3,3-dimethyl-N-(2-morpholinoethyl)butanamide

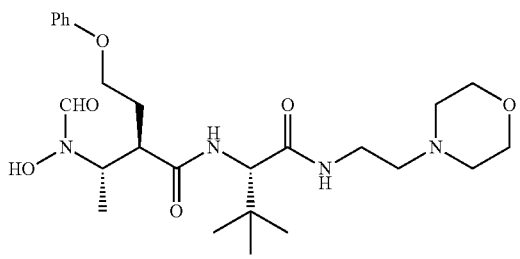 [SMILES: C[C@@H]([C@@H](CCOc1ccccc1)C(=O)N[C@H](C(=O)NCCN1CCOCC1)C(C)(C)C)N(O)C=O]

¹H NMR (400 MHz, MeOH-d₄): δ (ppm) 8.5 & 8.2 (s, 1H), 7.1-7.2 (m, 5H), 4.8 & 4.2 (m, 1H), 4.2 (s, 1), 3.45 (m, 8H), 3.2 (m, 2H), 2.6-2.8 (m, 2H), 2.55 (s, 3H), 1.49 (d, J=9.3, 3H), 0.94 (s, 9H).

MS (ESI, m/e): 493.29 (M+H)⁺. UV: $\lambda_{max}$=207 nM. HPLC: Water XBridge C18, 5 u, 4.6×250 mm; flow 1.0 ml/min; Waters 996 PDA detection at 215 nm; solvent 10-95% Acetonitrile (0.1% TFA) in H₂O (0.1% TFA) over 20 min; retention time 7.88 min; 100%.

SRI-028605

(R)—N—((S)-1-((2-(dimethylamino)ethyl)amino)-3,3-dimethyl-1-oxobutan-2-yl)-2-((S)-1-(N-hydroxyformamido)ethyl)-5-phenylpentanamide

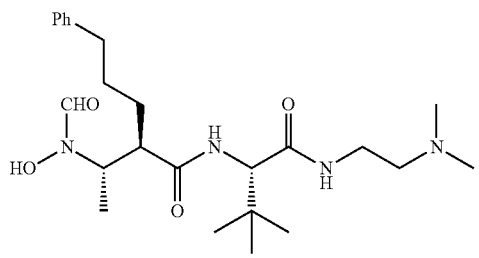 [SMILES: C[C@@H]([C@@H](CCCc1ccccc1)C(=O)N[C@H](C(=O)NCCN(C)C)C(C)(C)C)N(O)C=O]

¹H NMR (400 MHz, DMSO-d₆): δ (ppm) 9.8 & 9.2 (s, 1H), 8.2-8.4 (m, 3H), 7.6 (m, 5H), 4.24 & 3.75 (m, 1H), 4.18 (d, J=9.1, 1H), 3.2-2.8 (m, 3H), 2.6 (s, 3H), 2.4-2.5 (m, 2H), 2.35 (s, 3H), 1.4 (m, 4H), 1.08 (d, J=9.3, 3H), 0.90 (s, 9H).

MS (ESI, m/e): 449.10 (M+H)⁺. UV: $\lambda_{max}$=203.9 nM. HPLC: Water XBridge C18, 5 u, 4.6×250 mm; flow 1.0 ml/min; Waters 996 PDA detection at 215 nm; solvent 10-95% Acetonitrile (0.1% TFA) in H₂O (0.1% TFA) over 20 min; retention time 9.0 min; 93.8%.

SRI-028606

(R)—N—((S)-3,3-dimethyl-1-oxo-1-((2-(piperidin-1-yl)ethyl)amino)butan-2-yl)-2-((S)-1-(N-hydroxyformamido)ethyl)-5-phenylpentanamide

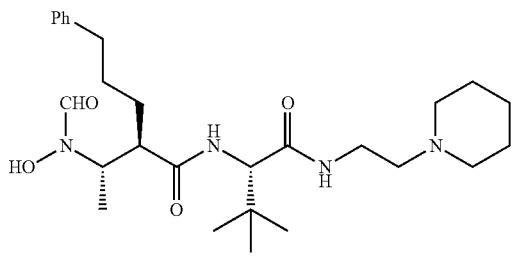 [SMILES: C[C@@H]([C@@H](CCCc1ccccc1)C(=O)N[C@H](C(=O)NCCN1CCCCC1)C(C)(C)C)N(O)C=O]

¹H NMR (400 MHz, DMSO-d₆): δ (ppm) 9.8 & 9.2 (s, 1H), 8.2-8.4 (m, 3H), 7.6 (m, 5H), 4.24 & 3.75 (m, 1H), 4.18 (d, J=9.1, 1H), 3.2-2.8 (m, 2H), 2.6 (m, 2H), 2.4-2.5 (m, 2H), 2.35 (m, 2H), 1.8 (m, 2H), 1.6 (m, 4H), 1.4 (m, 4H), 1.08 (d, J=9.3, 3H), 0.90 (s, 9H).

MS (ESI, m/e): 489.46 (M+H)⁺. UV: $\lambda_{max}$=202.7 nM. HPLC: Water XBridge C18, 5 u, 4.6×250 mm; flow 1.0 ml/min; Waters 996 PDA detection at 215 nm; solvent 10-95% Acetonitrile (0.1% TFA) in H₂O (0.1% TFA) over 20 min; retention time 10 min; 91.4%.

SRI-028607

(R)-2-((S)-1-(N-hydroxyformamido)ethyl)-N—((S)-1-((2-methoxyethyl)amino)-3,3-dimethyl-1-oxobutan-2-yl)-5-phenylpentanamide

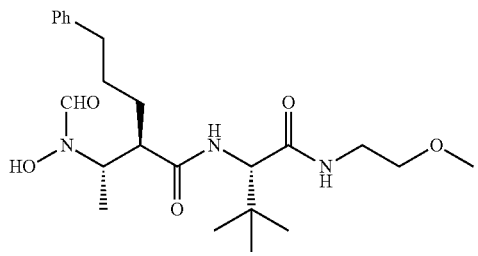 [SMILES: COCCNC(=O)[C@@H](NC(=O)[C@H](CCCc1ccccc1)[C@H](C)N(O)C=O)C(C)(C)C]

¹H NMR (400 MHz, DMSO-d₆): δ (ppm) 9.77 & 9.37 (s, 1H), 7.9-8.1 (m, 3H), 7.1-7.2 (m, 5H), 4.26 (d, J=9.6, 1H), 4.3 & 3.7 (m, 1H), 3.3 (s, 3H), 3.22 (m, 2H), 3.14 (s, 3H), 2.4-2.8 (m, 3H), 1.34 (m, 4H), 1.02 (d, J=9.3, 3H), 0.89 (s, 9H).

MS (ESI, m/e): 436.17 (M+H)⁺. UV: $\lambda_{max}$=207 nM. HPLC: Water XBridge C18, 5 u, 4.6×250 mm; flow 1.0 ml/min; Waters 996 PDA detection at 215 nm; solvent 10-90% Acetonitrile (0.1% TFA) in H₂O (0.1% TFA) over 20 min; retention time 11.97 min; 99.7%.

SRI-028608

(R)—N—((S)-1-((2-(1,1-dioxidothiomorpholino)ethyl)amino)-3,3-dimethyl-1-oxobutan-2-yl)-2-((S)-1-(N-hydroxyformamido)ethyl)-5-phenylpentanamide

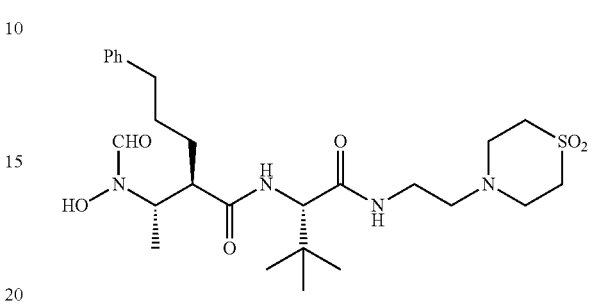

¹H NMR (400 MHz, DMSO-d₆): δ (ppm) 9.77 & 9.38 (s, 1H), 7.9-8.2 (m, 3H), 7.1-7.2 (m, 5H), 4.23 (d, J=9.2, 1H), 4.3 & 3.8 (m, 1H), 3.2 (m, 1H), 3.00 (m, 5H), 2.82 (m, 5H), 2.48 (m, 1H), 2.38 (m, 3H), 1.4 (m, 4H), 1.2 (m, 1H), 1.02 (d, J=9.3, 3H), 0.89 (s, 9H).

MS (ESI, m/e): 539.34 (M+H)⁺. UV: $\lambda_{max}$=210 nM. HPLC: Water XBridge C18, 5 u, 4.6×250 mm; flow 1.0 ml/min; Waters 996 PDA detection at 215 nm; solvent 10-90% Acetonitrile (0.1% TFA) in H₂O (0.1% TFA) over 20 min; retention time 10.1 min; 95.9%.

SRI-028609

(2R)—N-((2S)-3,3-dimethyl-1-oxo-1-(((tetrahydrofuran-2-yl)methyl)amino)butan-2-yl)-2-((S)-1-(N-hydroxyformamido)ethyl)-5-phenylpentanamide

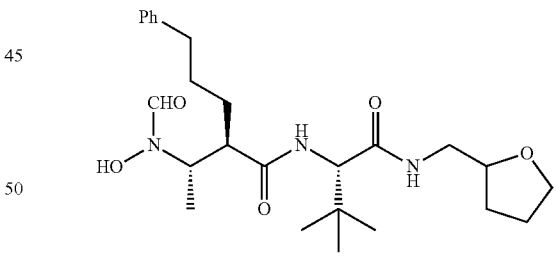

¹H NMR (400 MHz, DMSO-d₆): δ (ppm) 9.77 & 9.38 (s, 1H), 7.9-8.2 (m, 3H), 7.1-7.2 (m, 5H), 4.29 (m, 1H), 3.78 (m, 2H), 3.5 (m, 1H), 3.05 (m, 3H), 2.81 (m, 1H), 2.4-2.6 (m, 2H), 1.85 (m, 3H), 1.4 (m, 5H), 1.02 (d, J=9.3, 3H), 0.90 (s, 9H).

MS (ESI, m/e): 462.12 (M+H)⁺. UV: $\lambda_{max}$=205 nM. HPLC: Water XBridge C18, 5 u, 4.6×250 mm; flow 1.0 ml/min; Waters 996 PDA detection at 215 nm; solvent 10-90% Acetonitrile (0.1% TFA) in H₂O (0.1% TFA) over 20 min; retention time 11.3 min; 94.0%.

SRI-028610

(R)—N—((S)-3,3-dimethyl-1-(methylamino)-1-oxobutan-2-yl)-2-((S)-1-(N-hydroxyformamido)ethyl)-5-(4-methoxyphenyl)pentanamide

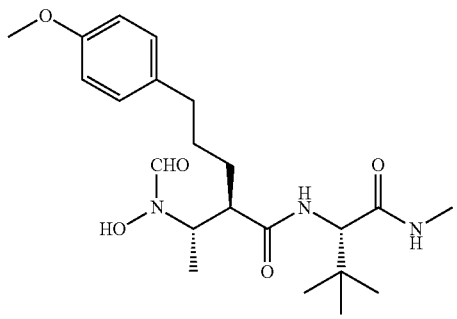

$^1$H NMR (400 MHz, DMSO-d$_6$): δ (ppm) 9.77 & 9.38 (s, 1H), 7.9-8.2 (m, 3H), 6.8-7.1 (m, 5H), 4.22 (d, J=9.5, 1H), 4.3 & 3.78 (m, 1H), 3.68 (s, 3H), 2.81 (m, 1H), 2.3 (m, 2H), 1.4 (m, 4H), 1.08 (d, J=9.3, 3H), 0.89 (s, 9H).

MS (ESI, m/e): 422.05 (M+H)$^+$. UV: λ$_{max}$=230 nM. HPLC: Water XBridge C18, 5 u, 4.6×250 mm; flow 1.0 ml/min; Waters 996 PDA detection at 215 nm; solvent 10-90% Acetonitrile (0.1% TFA) in H$_2$O (0.1% TFA) over 20 min; retention time 10.2 min; 98.3%.

SRI-028611

(S)-2-((2R,3S)-3-(N-hydroxyformamido)-2-(2-phenoxyethyl)butanamido)-N,3,3-trimethylbutanamide

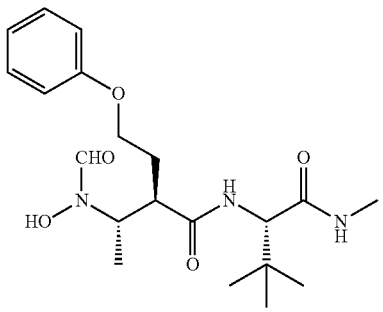 [SMILES: CNC(=O)[C@@H](NC(=O)[C@H](CCOc1ccccc1)[C@H](C)N(O)C=O)C(C)(C)C]

$^1$H NMR (400 MHz, DMSO-d$_6$): δ (ppm) 8.3 & 8.05 (s, 1H), 8.15 (m, 1H), 7.9 (m, 1H), 7.6 (s, 1H), 7.2 (m, 2H), 6.85 (m, 3H), 4.22 (d, J=9.5, 1H), 4.4 & 3.78 (m, 1H), 3.8 (m, 2H), 3.6 (m, 2H), 2.9 (m, 1H), 2.5 (s, 3H), 1.65 (m, 2H), 1.08 (d, J=9.3, 3H), 0.89 (s, 9H).

MS (ESI, m/e): 394.06 (M+H)$^+$. UV: λ$_{max}$=230 nM. HPLC: Water XBridge C18, 5 u, 4.6×250 mm; flow 1.0 ml/min; Waters 996 PDA detection at 230 nm; solvent 10-90% Acetonitrile (0.1% TFA) in H$_2$O (0.1% TFA) over 20 min; retention time 4.7 min; 96.03%.

SRI-028619

(R)—N—((S)-1-((2-ethoxyethyl)amino)-3,3-dimethyl-1-oxobutan-2-yl)-2-((S)-1-(N-hydroxyformamido)ethyl)-5-phenylpentanamide

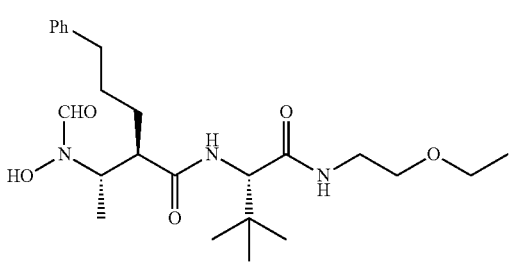 [SMILES: CCOCCNC(=O)[C@@H](NC(=O)[C@H](CCCc1ccccc1)[C@H](C)N(O)C=O)C(C)(C)C]

$^1$H NMR (400 MHz, DMSO-d$_6$): δ (ppm) 9.77 & 9.38 (s, 1H), 7.9-8.2 (m, 3H), 7.0-7.2 (m, 5H), 4.26 (d, J=9.6, 1H), 4.3 & 3.7 (m, 1H), 3.25 (m, 2H), 3.15 (m, 1H), 2.8 (m, 1H), 2.3-2.5 (m, 2H), 1.34 (m, 4H), 1.02 (m, 6H), 0.88 (s, 9H).

MS (ESI, m/e): 450.15 (M+H)$^+$. UV: λ$_{max}$=203.7 nM. HPLC: Water XBridge C18, 5 u, 4.6×250 mm; flow 1.0 ml/min; Waters 996 PDA detection at 215 nm; solvent 10-90% Acetonitrile (0.1% TFA) in H$_2$O (0.1% TFA) over 20 min; retention time 12.6 min; 96.8%.

SRI-028621

(R)-2-((S)-1-(N-hydroxyformamido)ethyl)-N—((S)-1-((2-isopropoxyethyl)amino)-3,3-dimethyl-1-oxobutan-2-yl)-5-phenylpentanamide

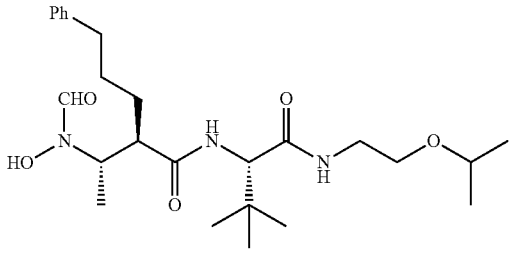 [SMILES: CC(C)OCCNC(=O)[C@@H](NC(=O)[C@H](CCCc1ccccc1)[C@H](C)N(O)C=O)C(C)(C)C]

$^1$H NMR (400 MHz, DMSO-d$_6$): δ (ppm) 9.77 & 9.38 (s, 1H), 7.9-8.2 (m, 3H), 7.0-7.2 (m, 5H), 4.26 (d, J=9.6, 1H), 4.3 & 3.7 (m, 1H), 3.42 (m, 1H), 3.25 (m, 2H), 3.05 (m, 2H), 2.8 (m, 1H), 2.3-2.5 (m, 2H), 1.34 (m, 4H), 1.02 (d, J=6.2, 6H), 0.89 (s, 9H).

MS (ESI, m/e): 464.18 (M+H)$^+$. UV: λ$_{max}$=203.9 nM. HPLC: Water XBridge C18, 5 u, 4.6×250 mm; flow 1.0 ml/min; Waters 996 PDA detection at 202 nm; solvent 10-90% Acetonitrile (0.1% TFA) in H$_2$O (0.1% TFA) over 20 min; retention time 13.5 min; 98.9%.

61
SRI-028620

(2R)-2-((S)-1-(N-hydroxyformamido)ethyl)-N-((2S)-1-((l-methoxybutan-2-yl)amino)-3,3-dimethyl-1-oxobutan-2-yl)-5-phenylpentanamide

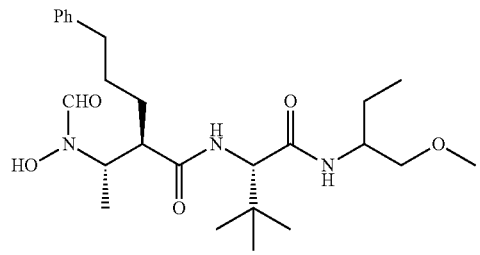 [SMILES: CCC(COC)NC(=O)[C@@H](NC(=O)[C@H](CCCc1ccccc1)[C@H](C)N(O)C=O)C(C)(C)C]

$^1$H NMR (400 MHz, DMSO-d$_6$): δ (ppm) 9.77 & 9.37 (s, 1H), 7.9-8.1 (m, 3H), 7.1-7.2 (m, 5H), 4.36 (m, 1H), 3.7 (m, 1H), 3.25 (s, 3H), 3.0-3.2 (m, 4H), 2.4-2.8 (m, 3H), 1.34 (m, 5H), 1.02 (d, J=9.3, 3H), 0.89 (s, 9H), 0.7 (t, J=6, 3H).

MS (ESI, m/e): 464.18 (M+H)$^+$. UV: λ$_{max}$=201.6 nM. HPLC: Water XBridge C18, 5 u, 4.6×250 mm; flow 1.0 ml/min; Waters 996 PDA detection at 205 nm; solvent 10-90% Acetonitrile (0.1% TFA) in H$_2$O (0.1% TFA) over 20 min; retention time 13.3 & 13.6 min (R/S mixture in 1:1); 99.1%.

SRI-028601

(S)-2-((2R,3S)-3-(N-hydroxyformamido)-2-phenethylbutanamido)-N,3,3-trimethylbutanamide

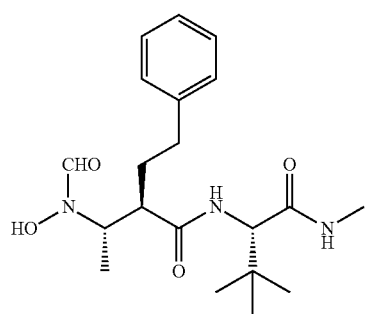 [SMILES: CNC(=O)[C@@H](NC(=O)[C@H](CCc1ccccc1)[C@H](C)N(O)C=O)C(C)(C)C]

62
SRI-028751

(R)—N—((S)-1-(2-(2-hydroxyethoxy)ethylamino)-3,3-dimethyl-1-oxobutan-2-yl)-2-((S)-1-(N-hydroxyformamido)ethyl)-5-phenylpentanamide

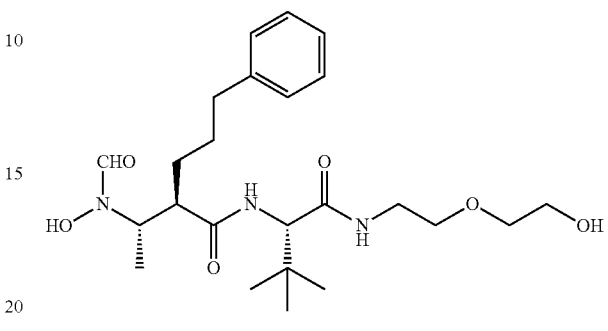

SRI-028753

(R)—N—((S)-1-(2-acetamidoethylamino)-3,3-dimethyl-1-oxobutan-2-yl)-2-((S)-1-(N-hydroxyformamido)ethyl)-5-phenylpentanamide

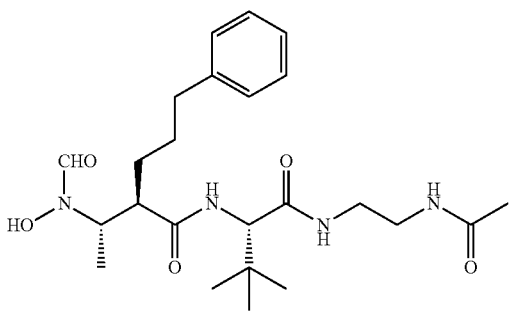 [SMILES: CC(=O)NCCNC(=O)[C@@H](NC(=O)[C@H](CCCc1ccccc1)[C@H](C)N(O)C=O)C(C)(C)C]

SRI-028754

(R)—N—((S)-1-(2-hydroxyethylamino)-3,3-dimethyl-1-oxobutan-2-yl)-2-((S)-1-(N-hydroxyformamido)ethyl)-5-(4-methoxyphenyl)pentanamide

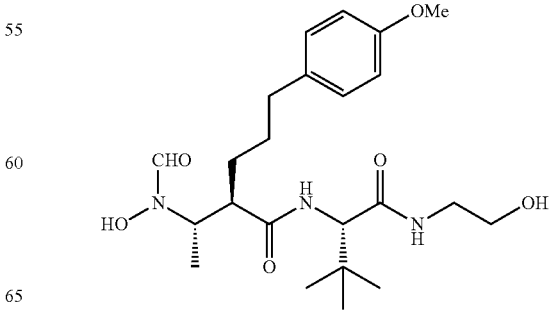

63
SRI-028755

(2R)—N-((2S)-3,3-dimethyl-1-oxo-1-((tetrahydrofuran-2-yl)methylamino)butan-2-yl)-2-((S)-1-(N-hydroxyformamido)ethyl)-5-(4-methoxyphenyl)pentanamide

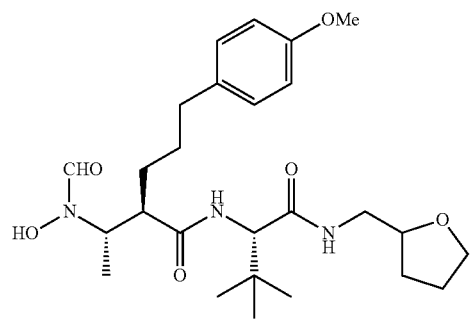 [SMILES: COc1ccc(CCC[C@@H](C(=O)N[C@H](C(=O)NCC2CCCO2)C(C)(C)C)[C@H](C)N(O)C=O)cc1]

SRI-028759

(S)-2-((2R,3S)-2-(4-chlorobenzyl)-3-(N-hydroxyformamido)butanamido)-N,3,3-trimethylbutanamide

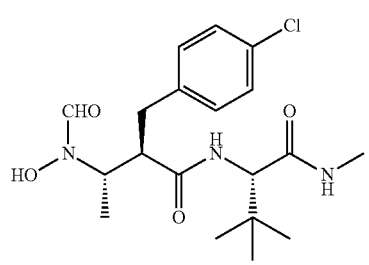 [SMILES: CNC(=O)[C@@H](NC(=O)[C@H](Cc1ccc(Cl)cc1)[C@H](C)N(O)C=O)C(C)(C)C]

SRI-028760

(S)-2-((2R,3S)-2-(4-chlorobenzyl)-3-(N-hydroxyformamido)butanamido)-3,3-dimethyl-N-(2-morpholinoethyl)butanamide

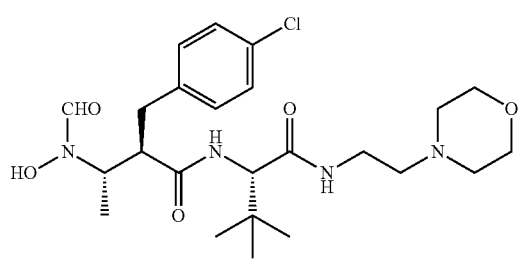 [SMILES: C[C@@H]([C@@H](Cc1ccc(Cl)cc1)C(=O)N[C@H](C(=O)NCCN1CCOCC1)C(C)(C)C)N(O)C=O]

64
SRI-028777

(R)—N—((S)-3,3-dimethyl-1-oxo-1-(tetrahydro-2H-pyran-4-ylamino)butan-2-yl)-2-((S)-1-(N-hydroxyformamido)ethyl)-5-phenylpentanamide

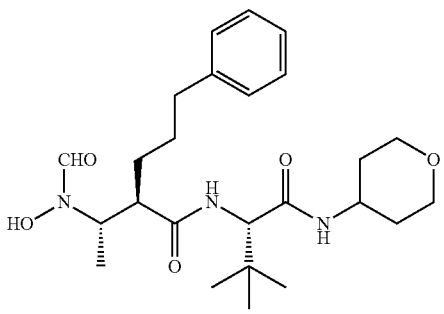 [SMILES: C[C@@H]([C@@H](CCCc1ccccc1)C(=O)N[C@H](C(=O)NC1CCOCC1)C(C)(C)C)N(O)C=O]

SRI-028778

(R)—N—((S)-3,3-dimethyl-1-oxo-1-(2-(2-oxoimidazolidin-1-yl)ethylamino)butan-2-yl)-2-((S)-1-(N-hydroxyformamido)ethyl)-5-phenylpentanamide

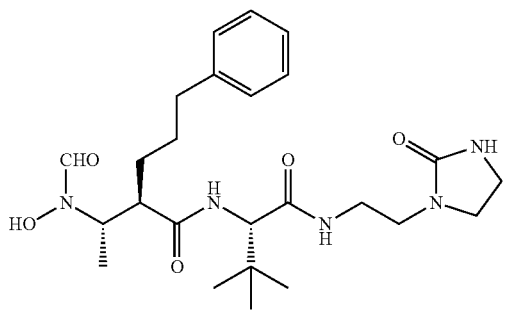 [SMILES: C[C@@H]([C@@H](CCCc1ccccc1)C(=O)N[C@H](C(=O)NCCN1CCNC1=O)C(C)(C)C)N(O)C=O]

SRI-028854

(2R)—N-((2S)-1-(3-hydroxycyclohexylamino)-3,3-dimethyl-1-oxobutan-2-yl)-2-((S)-1-(N-hydroxyformamido)ethyl)-5-phenylpentanamide

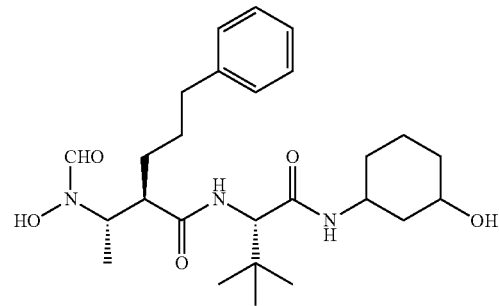 [SMILES: C[C@@H]([C@@H](CCCc1ccccc1)C(=O)N[C@H](C(=O)NC1CCCC(O)C1)C(C)(C)C)N(O)C=O]

SRI-028855

(R)—N—((S)-3,3-dimethyl-1-(methylamino)-1-oxobutan-2-yl)-2-((S)-1-(N-hydroxyformamido)ethyl)-5-p-tolylpentanamide

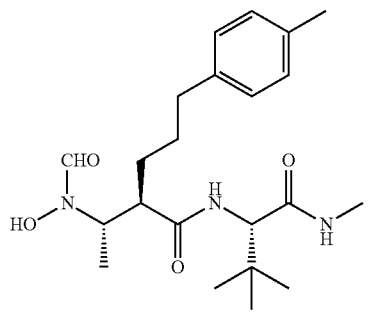 [SMILES: CNC(=O)[C@@H](NC(=O)[C@H](CCCc1ccc(C)cc1)[C@H](C)N(O)C=O)C(C)(C)C]

SRI-028594 (GI254023X)

(R)—N—((S)-3,3-dimethyl-1-(methylamino)-1-oxobutan-2-yl)-2-((S)-1-(N-hydroxyformamido)ethyl)-5-phenylpentanamide

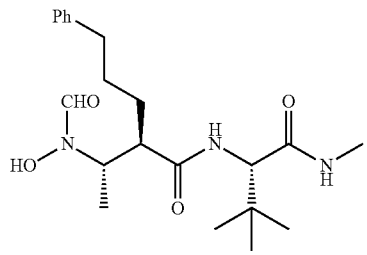 [SMILES: CNC(=O)[C@@H](NC(=O)[C@H](CCCc1ccccc1)[C@H](C)N(O)C=O)C(C)(C)C]

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

U.S. Pat. No. 6,172,064
U.S. Pat. No. 6,191,150
U.S. Pat. No. 6,329,400
U.S. Pat. No. 7,723,349
U.S. patent application Ser. No. 10/518,110
U.S. patent application Ser. No. 12/160,862
U.S. patent application Ser. No. 12/327,313
U.S. patent application Ser. No. 12/605,118
U.S. Patent Ser. 60/534,501
U.S. Patent Ser. 60/512,016
U.S. Patent Ser. 60/515,352
U.S. Patent Ser. 61/453,648
U.S. Patent Ser. 61/411,765
U.S. Patent Ser. 61/511,032
Bhakdi and Tranum-Jensen, *Microbiol. Rev.*, 55:733-751, 1991.
Brosnahan et al., *Immunol.*, 182:2364-2373, 2009.
Bubeck Wardenburg and Schneewind, *J. Exp. Med.*, 205:287-294, 2008.
Bubeck Wardenburg et al., *Infect. Immun.*, 75:1040-1044, 2007.
Bubeck Wardenburg et al., *Nature Med.*, 13:1405-1407, 2007.
Callegan et al., *Infect. Immun.*, 62:2478-2482, 1994.
Dijkstra et al., *Virchows Arch.*, 454:441-449, 2009.
Dudek et al., *Mol. Biol. Cell*, 21(22):4042-4056, 2010.
Emorl and Gaynes, *Clin. Microbiol. Rev.*, 6(4):428-42, 1993.
Gomez et al., *EMBO J.*, 26:701-709, 2007.
Gonzalez et al., *Cell Mol. Life Sci.*, 65:493-507, 2008.
Gumbiner, *Cell*, 84:345, 1996.
Harlow and Lane, In: *Antibodies: A Laboratory Manual*, Cold Spring Harbor Laboratory, 1988.
Hartmann et al., *Hum. Mol. Genet.*, 11:2615-2624, 2002.
Hoettecke et al., *Neurodegener. Dis.*, 7(4):232-238, 2010.
Hooper et al., *Biochem. J.*, 321:265-279, 1997.
Hooper, *FEBS Letters*, 354:1-6, 1994.
Hoy et al., *EMBO*, 11:798, 2010.
Iacovache et al., *Biochim Biophys Acta.*, 1778 (7-8): 1611-23, 2008.
Illek et al., *Cell Physiol. Biochem.*, 22:57-68, 2008.
Inoshima et al., *Nature Medicine*, 2011 (IN PRESS)
Jursch et al., *Infect. Immun.*, 62:2249, 1994.
Karginov et al., *Bioorg, Med, Chem.*, 15:5424, 2007.
Kennedy et al., *J. Infect. Dis.*, 202(7):1050-1058, 2010.
Kim et al., *Cell Host Microbe.*, 8(1):20-35, 2010a.
Kim et al., *Vaccine*, 28(38):6382-6392, 2010b.
Lemichez et al., *Nat. Rev. Microbiol.*, 8(2):93-104, 2010.
Lowy, *N. Engl. J. Med.*, 339:520, 1998.
Ludwig et al., *Comb. Chem. High Throughput Screen*, 8:161-171, 2005.
Maretzky et al., *Proc. Natl. Acad. Sci. USA*, 102:9182-9187, 2005.
Maretzky et al., *J. Invest. Dermatol.*, 128:1737-1746, 2008.
Marriott and Dockrell, *Int. J. Biochem. Cell Biol.*, 38:1848-1854, 2006.
Martin et al., *Infect. Immun.*, 79:1898-1904, 2011.
Matthay and Zemans, *Annu. Rev. Pathol.*, 6:147, 2010.
Matthay and Zemans, *Annu. Rev. Pathol.*, 28:147-163, 2011.
Menzies and Kernodle, *Infect. Immun.*, 62:1843-1847, 1994.
Menzies and Kernodle, *Infect. Immun*, 64:1839-1841, 1996.
Murphy, *Semin. Cell Dev. Biol.*, 20:138-145, 2009.
O'Callaghan et al., *Infect. Immun.*, 65:1571-1578, 1997.
Ong and Leung, *Immun. Allergy Clincis of NA*, 30:309-321, 2010.
Patel et al., *Infect. Immun.*, 55:3103-3110, 1987.
PCT Appin. WO 03/051825
PCT Appin. WO 03/106381
Perl et al., *Proc. Natl. Acad. Sci. USA*, 99:10482-10487, 2002a.
Perl et al., *Transgenic Res.*, 11:21-29, 2002b.
Pochetuhen et al., *Am. J. Pathol.*, 171(2):428-437, 2007.
Powers et al., *J. Infect. Diseases*, 2011 (IN PRESS)
Ragle and Bubeck Wardenburg, *Infect. Immun.*, 77:2712-2718, 2009.

Ragle et al., *Antimicrob. Agents Chemother.*, 54:298, 2010.
Reiss and Saftig, *Semin. Cell Dev. Biol.*, 20:126-137, 2009.
Rice et al., *Am. J. Physiol. Lung Cell Mol. Physiol.*, 283: L256-264, 2002.
Rubins et al., *J. Clin. Invest.*, 95:142-150, 1995.
Schulte et al., *Cell Death and Differentiation*, 14:1040-1049, 2007.
Schulz et al., *Circ. Res.*, 102(10):1192-1201, 2008.
Seals and Courtneidge, *Genes Dev.*, 17:7-30, 2003.
Shapiro and Weis, *Cold Spring Harb. Perspect. Biol.*, 1:a003053, 2009.
Song et al., *Science*, 274:1859-1866, 1996.
Steinhusen et al., *J. Biol. Chem.*, 276:4972-4980, 2001.
Tian et al., *Int. Immunol.*, 20:1181-1187, 2008.
Tomita and Kamio, *Biosci. Biotechnol. Biochem.*, 61:565-572, 1997.
Tweten, *Infection and Immunity*, 73 (10): 6199-6209, 2005.
Walker and Bayley, *J. Biol. Chem.*, 270:23065, 1995.
Wilke and Bubeck Wardenburg, *Proc. Natl. Acad. Sci. USA*, 107(30):13473-13478, 2010.
Wu et al., *Proc. Natl. Acad. Sci. USA*, 95:14979, 1998.
Vasioukhin et al., *Proc. Natl. Acad. Sci. USA*, 96:8551-8556, 1999.

The invention claimed is:

1. A compound of the formula:

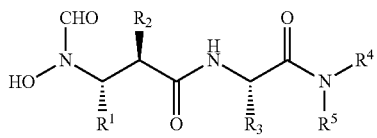

wherein:
$R^1$ is hydrogen, alkyl, halogen, haloalkyl, alkenyl, or alkynyl;
$R^2$ is hydrogen, alkyl, benzyl, aryl, aralkyl, functionalized aralkyl, alkenyl, or alkynyl;
$R^3$ is hydrogen, alkyl, benzyl, aryl, alkenyl, or alkynyl;
$R^4$ is (tetrahydrofuran-2-yl)methyl; and
$R^5$ is hydrogen or methyl,
or a salt, prodrug, enantiomer, or diastereomer thereof.

2. The compound of claim 1, wherein $R^1$ is methyl.

3. The compound of claim 1, wherein $R^2$ is aralkyl or functionalized aralkyl.

4. The compound of claim 1, wherein $R^3$ is tert-butyl.

5. The compound of claim 1, further defined as:

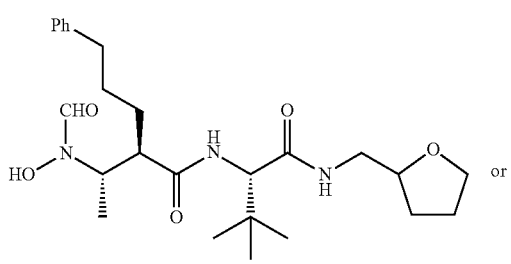

or

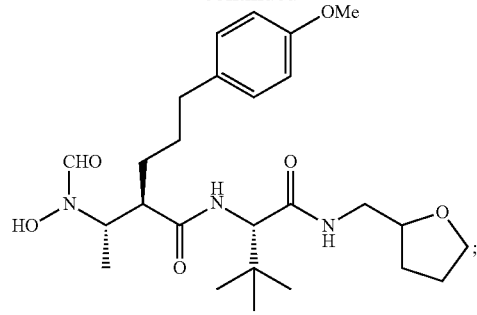

or a salt, enantiomer or prodrug thereof.

6. A compound of the formula:

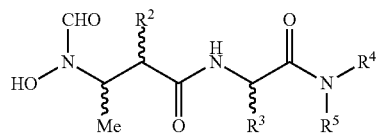

wherein:
$R^2$ is hydrogen, alkyl, benzyl, aryl, aralkyl, functionalized aralkyl, alkenyl, or alkynyl;
$R^3$ is hydrogen, alkyl, benzyl, aryl, alkenyl, or alkynyl;
$R^4$ is (tetrahydrofuran-2-yl)methyl; and
$R^5$ is hydrogen or methyl,
or a salt, prodrug, enantiomer, or diastereomer thereof.

7. A compound of the formula:

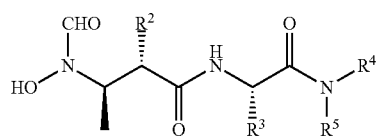

wherein:
$R^2$ is hydrogen, alkyl, benzyl, aryl, aralkyl, functionalized aralkyl, alkenyl, or alkynyl;
$R^3$ is hydrogen, alkyl, benzyl, aryl, alkenyl, or alkynyl;
$R^4$ is (tetrahydrofuran-2-yl)methyl; and
$R^5$ is hydrogen or methyl,
or a salt, prodrug, enantiomer, or diastereomer thereof.

8. A compound of the formula:

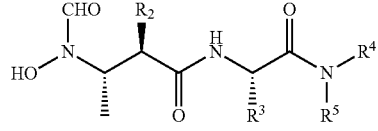

wherein:
$R^2$ is hydrogen, alkyl, benzyl, aryl, aralkyl, functionalized aralkyl, alkenyl, or alkynyl;
$R^3$ is hydrogen, alkyl, benzyl, aryl, alkenyl, or alkynyl;
$R^4$ is (tetrahydrofuran-2-yl)methyl; and
$R^5$ is hydrogen or methyl,
or a salt, prodrug, enantiomer, or diastereomer thereof.

9. A pharmaceutical composition comprising:
(a) the compound of claim 1 or a pharmaceutically acceptable salt, prodrug, enantiomer, or diastereomer thereof; and
(b) an excipient.

10. An ADAM10 inhibitor of the formula:
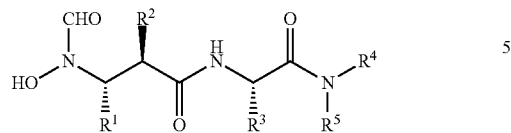
wherein:
 $R^1$ is hydrogen, alkyl, halogen, haloalkyl, alkenyl, or alkynyl;
 $R^2$ is hydrogen, alkyl, benzyl, aryl, aralkyl, functionalized aralkyl, alkenyl, or alkynyl;
 $R^3$ is hydrogen, alkyl, benzyl, aryl, alkenyl, or alkynyl;
 $R^4$ is (tetrahydrofuran-2-yl)methyl; and
 $R^5$ is hydrogen or methyl,
or a salt, prodrug thereof.
* * * * *